US008710000B2

(12) United States Patent
Garibay et al.

(10) Patent No.: US 8,710,000 B2
(45) Date of Patent: Apr. 29, 2014

(54) INSULIN DERIVATIVE

(75) Inventors: Patrick William Garibay, Holte (DK); Thomas Høeg-Jensen, Klampenborg (DK)

(73) Assignee: Novo Nordisk A/S, Bagsvaerd (DK)

( * ) Notice: Subject to any disclaimer, the term of this patent is extended or adjusted under 35 U.S.C. 154(b) by 289 days.

(21) Appl. No.: 12/741,964

(22) PCT Filed: Nov. 7, 2008

(86) PCT No.: PCT/EP2008/065141
§ 371 (c)(1),
(2), (4) Date: May 26, 2010

(87) PCT Pub. No.: WO2009/060071
PCT Pub. Date: May 14, 2009

(65) Prior Publication Data
US 2010/0279931 A1 Nov. 4, 2010

Related U.S. Application Data

(60) Provisional application No. 60/986,311, filed on Nov. 8, 2007.

(30) Foreign Application Priority Data

Nov. 8, 2007 (EP) .................... 07120251
Jul. 31, 2008 (EP) .................... 08161557

(51) Int. Cl.
*A61K 38/28* (2006.01)
*A61K 33/30* (2006.01)
*A61K 38/00* (2006.01)
*A61P 3/10* (2006.01)
*A61P 7/12* (2006.01)

(52) U.S. Cl.
CPC ............. *A61K 38/00* (2013.01); *A61K 38/28* (2013.01)
USPC ............... 514/5.9; 514/6.4; 514/6.9

(58) Field of Classification Search
None
See application file for complete search history.

(56) References Cited

U.S. PATENT DOCUMENTS

| 5,750,497 A | 5/1998 | Havelund et al. |
| 5,898,067 A | 4/1999 | Balschmidt et al. |
| 5,905,140 A | 5/1999 | Hansen |
| 6,011,007 A | 1/2000 | Havelund et al. |
| 6,174,856 B1 | 1/2001 | Langballe et al. |
| 6,869,930 B1 | 3/2005 | Havelund et al. |
| 7,615,532 B2 * | 11/2009 | Jonassen et al. ............... 514/1.1 |
| 8,003,605 B2 | 8/2011 | Bayer et al. |
| 8,067,362 B2 * | 11/2011 | Kodra et al. ................... 514/6.3 |
| 2008/0076705 A1 * | 3/2008 | Kodra et al. ...................... 514/3 |
| 2008/0171695 A1 * | 7/2008 | Garibay et al. .................... 514/3 |
| 2009/0074882 A1 * | 3/2009 | Havelund et al. ............. 424/641 |
| 2009/0137454 A1 * | 5/2009 | Fynbo et al. ...................... 514/3 |
| 2009/0239785 A1 * | 9/2009 | Hubalek et al. .................... 514/4 |
| 2010/0227796 A1 * | 9/2010 | Garibay et al. .................... 514/3 |

FOREIGN PATENT DOCUMENTS

| EP | 0894095 | 5/2003 |
| GB | 894095 A | 4/1962 |
| GB | 1492997 | 11/1977 |
| JP | 1254699 | 5/1979 |
| WO | WO 95/07931 | 3/1995 |
| WO | WO 96/29344 | 9/1996 |
| WO | WO 97/31022 | 8/1997 |
| WO | 98/02460 A1 | 1/1998 |
| WO | WO 03/013573 | 2/2003 |
| WO | 2005/005477 A2 | 1/2005 |
| WO | 2005/012347 A2 | 2/2005 |
| WO | 2005/047508 A1 | 5/2005 |
| WO | 2006/008238 A1 | 1/2006 |
| WO | WO 2006/082204 | 8/2006 |
| WO | WO 2006/082205 | 8/2006 |
| WO | 2007/074133 A2 | 7/2007 |
| WO | 2007/096431 A1 | 8/2007 |
| WO | 2007/128815 A1 | 11/2007 |
| WO | WO 2007/128817 | 11/2007 |
| WO | 2008/152106 A1 | 12/2008 |
| WO | 2009/060071 A1 | 5/2009 |
| WO | 2010/049488 A1 | 5/2010 |
| WO | 2011/141407 A1 | 11/2011 |

OTHER PUBLICATIONS

Havelund, S. et al., "The Mechanism of Protraction of Insulin Detemir, a Long-acting, Acylated Analog of Human Insulin", Pharmaceutical Research, 2004, vol. 21, No. 8, pp. 1498-1504.

* cited by examiner

*Primary Examiner* — Marcela M Cordero Garcia
(74) *Attorney, Agent, or Firm* — Michael J. Brignati

(57) ABSTRACT

The present invention relates to novel human insulin derivatives which are soluble at physiological pH values and have a prolonged profile of action. The invention also relates to pharmaceutical compositions containing such derivatives and to methods of treating diabetes and hyperglycaemia using the insulin derivatives of the invention.

17 Claims, No Drawings

INSULIN DERIVATIVE

CROSS-REFERENCE TO RELATED APPLICATIONS

This application is a 35 U.S.C. §371 national stage application of International Patent Application PCT/EP2008/065141 (published as WO 2009/060071 A1), filed Nov. 7, 2008, which claimed priority of European Patent Application 07120251.9, filed Nov. 8, 2007 and European Patent Application 08161557.7, filed Jul. 31, 2008; this application further claims priority under 35 U.S.C. §119 of U.S. Provisional Application 60/986,311, filed Nov. 8, 2007.

FIELD OF THE INVENTION

The present invention relates to novel human insulin derivatives which are soluble at physiological pH values and have a prolonged profile of action. The invention also relates to pharmaceutical compositions containing insulin derivatives of the invention, to methods of treating diabetes and hyperglycaemia using the insulin derivatives of the invention.

BACKGROUND OF THE INVENTION

Currently, the treatment of diabetes, both type 1 diabetes and type 2 diabetes, relies to an increasing extent on the so-called intensive insulin treatment. According to this regimen, the patients are treated with multiple daily insulin injections comprising one or two daily injections of a long acting insulin to cover the basal insulin requirement supplemented by bolus injections of a rapid acting insulin to cover the insulin requirement related to meals.

Long acting insulin compositions are well known in the art. Thus, one main type of long acting insulin compositions comprises injectable aqueous suspensions of insulin crystals or amorphous insulin. In these compositions, the insulin compounds utilized typically are protamine insulin, zinc insulin or protamine zinc insulin.

Certain drawbacks are associated with the use of insulin suspensions. Thus, in order to secure an accurate dosing, the insulin particles must be suspended homogeneously by gentle shaking before a defined volume of the suspension is withdrawn from a vial or expelled from a cartridge. Also, for the storage of insulin suspensions, the temperature must be kept within more narrow limits than for insulin solutions in order to avoid lump formation or coagulation.

International patent application WO 2006/082204 (Novo Nordisk A/S) discloses insulin derivatives having an aromatic group in the side chain.

Patent application WO 2006/082205 (Novo Nordisk A/S), disclose insulin derivatives having a PEG in the side chain.

Insulin derivatives with a charged terminal group in the substituent are disclosed in international patent application no. EP2007/054444 (Novo Nordisk A/S).

However, there is still a need for insulin having a more prolonged profile of action than the insulin derivatives known up till now.

SUMMARY OF THE INVENTION

In one aspect the invention concerns an insulin derivative having a formula

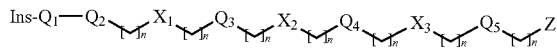

wherein Ins is a parent insulin moiety and $Q_1$-$Q_2$-[CH$_2$]$_n$—$X_1$—[CH$_2$]$_n$-$Q_3$-[CH$_2$]$_n$—$X_2$—[CH$_2$]$_n$-$Q_4$-[CH$_2$]$_n$—$X_3$—[CH$_2$]$_n$-$Q_5$-[CH$_2$]$_n$—Z is a substituent and where the Ins is attached to the substituent via an amide bond between the α-amino group of the N-terminal amino acid residue of the B chain of Ins or an ε-amino group of a Lys residue present in the A or B chain of Ins and a CO group in $Q_1$ or $Q_2$ of the substituent;

each n is independently 0, 1, 2, 3, 4, 5 or 6;

$Q_1$, $Q_2$, $Q_3$, $Q_4$ and $Q_5$, independently of each other can be:
an amino acid residue, which residue forms, with its carboxylic acid group, an amide group together with the α-amino group of the N-terminal amino acid residue of the B chain of Ins or together with the ε-amino group of a Lys residue present in the A or B chain of Ins, or a chain composed of two, three or four α-amino acid residues as specified above linked together via amide bonds, which chain—via an amide bond—is linked to the α-amino group of the N-terminal amino acid residue of the B chain of Ins or to the ε-amino group of a Lys residue present in the A or B chain of Ins, or —CO—(CH$_2$)$_p$—NR$^1$—(CH$_2$)$_p$—, where each p is independently 1, 2, 3, 4, 5, or 6; and where R$^1$ can be H, —CH$_3$ or —(CH$_2$)$_{1-6}$—CH$_3$;

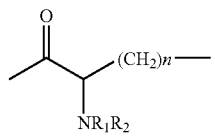

where n=1-6, and where R$^1$ and R$^2$, independently of each other can be H, —CH$_3$ or —(CH$_2$)$_{1-6}$—CH$_3$

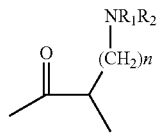

where n=1-6, and where R$^1$ and R$^2$, independently of each other can be H, —CH$_3$ or —(CH$_2$)$_{1-6}$—CH$_3$ —CO—(CH$_2$)$_p$—Ar—(CH$_2$)$_p$—, where Ar can be arylene or heteroarylene, which is substituted with at least one of the following groups consisting of —NR$^1$R$^2$, —(CH$_2$)$_p$—NR$^1$R$^2$— and Ar may also be substituted with one or two groups selected from the group consisting of —CH$_3$, —(CH$_2$)$_{1-6}$—CH$_3$, where each p is independently 1, 2, 3, 4, 5, or 6, and where R$^1$ and R$^2$, independently of each other can be H, —CH$_3$ or —(CH$_2$)$_{1-6}$—CH$_3$;

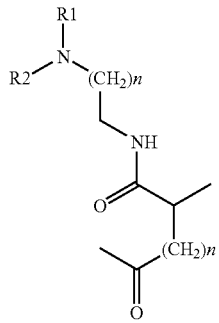

where n=1-6 and where R$^1$ and R$^2$, independently of each other can be H, —CH$_3$ or —(CH$_2$)$_{1-6}$—CH$_3$ —$(CH_2)_m$— where m is an integer in the range of 6 to 32;
a divalent hydrocarbon chain comprising 1, 2 or 3 —CH═CH— groups and a number of —$CH_2$— groups sufficient to give a total number of carbon atoms in the chain in the range of 4 to 32;
—CO—$((CR^5R^6)_{1-6}$—NH—CO)—;
—(CO—$(CR^5R^6)_{1-6}$—CO—NH$)_{1-4}$—, where $R^5$ independently can be H, $CH_3$,—$(CH_2)_{1-6}CH_3$ or —$CONH_2$ and $R^6$ independently can be H, —$CH_3$,—$(CH_2)_{1-6}CH_3$;
—CO—$(CH_2)_{0-3}$—Ar—$(CH_2)_{0-3}$— where Ar can be arylene or heteroarylene, which may be substituted with one or two groups selected from the group consisting of —$CH_3$, —$(CH_2)_{1-6}$—$CH_3$, —$NR^1R^2$, —$CONR^1R^2$ or —$SO_2NR^1R^2$, where $R^1$ and $R^2$, independently of each other can be H, —$CH_3$ or —$(CH_2)_{1-6}$—$CH_3$;
—$(CH_2CH_2O)_y$—; $(CH_2CH_2CH_2O)_y$—; $(CH_2CH_2CH_2CH_2O)_y$—; $(CH_2CH_2OCH_2CH_2CH_2CH_2O)_y$— or $(CH_2CH_2CH_2OCH_2CH_2CH_2CH_2O)_y$—;
—$(CH_2OCH_2)_y$— where y is 1-20;
arylene or heteroarylene, which may be substituted with one or two groups selected from the group consisting of —$CH_3$, —$(CH_2)_{1-6}$—$CH_3$, —$CONR^1R^2$ or —$SO_2NR^1R^2$, where $R^1$ and $R^2$, independently of each other can be H, —$CH_3$ or —$(CH_2)_{1-6}$—$CH_3$; or
a chain of the formula

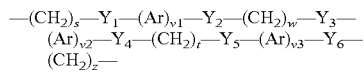

wherein Ar is defined as above, $Y_1$-$Y_6$ independently of each other can be O, S, S═O, $SO_2$ or a bond; where s, w, t and z independently of each other are zero or an integer from 1 to 10 so that the sum of s, w, t and z is in the range from 4 to 30, and $v_1$, $v_2$, and $v_3$ independently of each other can be zero or 1 with the proviso that $Y_1$-$Y_6$ do not link to each other and that the structure —O—$(CH_2)_1$—O— does not occur; or
a bond;
with the proviso that at least one of $Q_1$-$Q_5$ is not a bond;
$X_1$, $X_2$ and $X_3$ are independently of each other
O;
—C═O
a bond;
$NCOR^1$, where $R^1$ can be H, —$CH_3$ or —$(CH_2)_{1-6}$—$CH_3$; or

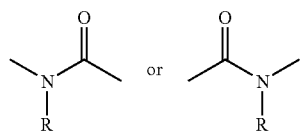

where R is hydrogen, $C_{1-3}$-alkyl, $C_{2-3}$-alkenyl or $C_{2-3}$-alkynyl;
with the proviso that
$X_1$, $X_2$ and $X_3$ cannot bind to Z and
when $X_1$, $X_2$ and $X_3$ are O, then $X_1$, $X_2$ and $X_3$ do not bind directly to O in $Q_1$, $Q_2$, $Q_3$, $Q_4$, and $Q_5$
and
Z is:
—COOH;
—CO-Asp;
—CO-Glu;
—CO-Gly;
—CO-Sar;
—CH(COOH)$_2$,
—N(CH$_2$COOH)$_2$;
—$SO_3H$
—$OSO_3H$
—$OPO3H_2$
—$PO_3H_2$
-tetrazol-5-yl
—O—$W_1$ or
$W_1$ where $W_1$ is arylene or heteroarylene, which may be substituted with one or two groups selected from the group consisting of tetrazo-5-lyl, —COOH, —$SO_3H$, —$(CH_2)_{1-6}$—$SO_3H$, —$(CH_2)_{1-6}$—O—$PO_3H_2$, —$CONR^3R^4$ or —$SO_2NR^3R^4$, where $R^3$ and $R^4$, independently of each other can be H, —$(CH_2)_{1-6}$—$SO_3H$, or —$(CH_2)_{1-6}$—O—$PO_3H_2$;
and any $Zn^{2+}$ complex thereof, provided that at least one amine or positively charged amino acid is present in the substituent.

The invention further relates to a zinc complex of the insulin derivative, a pharmaceutical composition comprising the insulin derivative or the zinc complex, a method for treating diabetic patients by the use of the insulin derivative or the zinc complex.

DEFINITIONS

By "insulin analogue" as used herein is meant a polypeptide which has a molecular structure which formally can be derived from the structure of a naturally occurring insulin, for example that of human insulin, by deleting and/or exchanging at least one amino acid residue occurring in the naturally occurring insulin and/or adding at least one amino acid residue. The added and/or exchanged amino acid residues can either be codable amino acid residues or other naturally occurring residues or purely synthetic amino acid residues.

The insulin analogues may be such wherein position 28 of the B chain may be modified from the natural Pro residue to one of Asp, Lys, or Ile. In another aspect Lys at position B29 is modified to Pro. Also, Asn at position A21 may be modified to Ala, Gln, Glu, Gly, His, Ile, Leu, Met, Ser, Thr, Trp, Tyr or Val, in particular to Gly, Ala, Ser, or Thr and preferably to Gly. Furthermore, Asn at position B3 may be modified to Lys or Asp. Further examples of insulin analogues are des(B30) human insulin; des(B30) human insulin analogues; insulin analogues wherein PheB1 has been deleted; insulin analogues wherein the A-chain and/or the B-chain have an N-terminal extension and insulin analogues wherein the A-chain and/or the B-chain have a C-terminal extension. Thus one or two Arg may be added to position B1.

In aspects of the invention a maximum of 17 amino acids have been modified. In aspects of the invention a maximum of 15 amino acids have been modified. In aspects of the invention a maximum of 10 amino acids have been modified. In aspects of the invention a maximum of 8 amino acids have been modified. In aspects of the invention a maximum of 7 amino acids have been modified. In aspects of the invention a maximum of 6 amino acids have been modified. In aspects of the invention a maximum of 5 amino acids have been modified. In aspects of the invention a maximum of 4 amino acids have been modified. In aspects of the invention a maximum of 3 amino acids have been modified. In aspects of the invention a maximum of 2 amino acids have been modified. In aspects of the invention 1 amino acid has been modified.

With "desB30 insulin", "desB30 human insulin" is meant a natural insulin or an analogue thereof lacking the B30 amino acid residue. Similarly, "desB29desB30 insulin" or "desB29desB30 human insulin" means a natural insulin or an analogue thereof lacking the B29 and B30 amino acid residues.

With "B1", "A1" etc. is meant the amino acid residue at position 1 in the B-chain of insulin (counted from the N-terminal end) and the amino acid residue at position 1 in the A-chain of insulin (counted from the N-terminal end), respectively. The amino acid residue in a specific position may also be denoted as e.g. PheB1 which means that the amino acid residue at position B1 is a phenylalanine residue.

With "insulin" as used herein is meant human insulin, porcine insulin or bovine insulin with disulfide bridges between CysA7 and CysB7 and between CysA20 and CysB19 and an internal disulfide bridge between CysA6 and CysA11.

By "parent insulin" is meant a naturally occurring insulin such as human insulin or porcine insulin. Alternatively, the parent insulin can be an insulin analogue.

The expression "positively charged" means that at least one group or more groups that would assume a positive charge at pH interval 4 to 9 are present.

When an insulin derivative according to the invention is stated to be "soluble at physiological pH values" it means that the insulin derivative can be used for preparing insulin compositions that are fully dissolved at physiological pH values. Such favourable solubility may either be due to the inherent properties of the insulin derivative alone or a result of a favourable interaction between the insulin derivative and one or more ingredients contained in the vehicle.

The term "no blunting" as used herein means that when formulated in one formulation both the rapid acting insulin and the acylated insulin has profile of action which is identical or substantially identical with the profile of action, when administering the rapid acting insulin and the acylated insulin in separate formulations.

The expression "high molecular weight insulin" or "hmw" means that the molecular weight of a complex of human insulin, of an insulin analogue or of an insulin derivative is above human serum albumin, above a dodecameric complex of an insulin analogue or of an insulin derivative or more than about 72 kDalton.

The expression "medium molecular weight insulin" or "mmw" means that the molecular weight of a complex of human insulin, of an insulin analogue or of an insulin derivative is from about an insulin hexamer to about an insulin dodecamer between 24 and 80 kDalton.

The expression "low molecular weight insulin" or "lmw" means that the molecular weight of a human insulin, an insulin analogue or an insulin derivative is below 24 kDalton.

The expression "substituent" means the chemical moiety that is conjugated to the insulin peptide and is not part of the insulin amino acid sequence.

The following abbreviations have been used in the specification and examples:

| | |
|---|---|
| CV | column volume |
| HPLC | High Performance Liquid Chromatography |
| HSA | human serum albumin |
| LC | liquid chromatography |
| MALDI | Matrix Assisted Laser Desorption Ionization |
| MS | mass spectrometry |
| RT | room temperature |
| SEC | size exclusion chromatography |
| SPA | Scitillation Proximity Assay |
| Tris | tris(hydroxymethyl)aminomethane |
| O.D. | optical density = absorbance |
| X2 monomer | AspB9 GluB27 human insulin |
| DIEA: | N,N-diisopropylethylamine |
| DMF: | N,N-dimethylformamide |
| Sar: | Sarcosine (N-methyl-glycine) |
| tBu: | tert-butyl |
| TSTU: | O-(N-succinimidyl)-1,1,3,3-tetramethyluronium tetrafluoroborate |
| THF: | Tetrahydrofuran |
| EtOAc or AcOEt: | Ethyl acetate |
| DIPEA: | Diisopropylethylamine |
| TEA: | triethyl amine |
| TFA: | trifluoracetic acid |
| DCM: | dichloromethane |
| PEG: | polyethyleneglycol |
| GIR: | Glucose infusion rate |
| DAP | 2,3-Diaminopropionic acid |
| DAB | 2,4-Diaminobutyric acid |
| Orn | Ornithine or 2,5-diamino-pentanoic acid |

DESCRIPTION OF THE INVENTION

The present invention is based on the recognition that having an amine or a positively charged substituent in an insulin derivative molecule and a charged terminal group, plays an important role for the in vivo duration of action of prolonged-acting insulins, and for the mixability of prolonged-acting insulin with fast-acting insulin with no blunting. The insulin derivatives have a tendency of forming complexes with a high molecular weight and thereby show a protracted profile of action.

Advantageously, insulin derivatives according to the invention are soluble at physiological pH values, have a potency which is comparable to that of human insulin, and are mixable with fast-acting insulins with no blunting.

The invention will be summarized in the following paragraphs:

1. An insulin derivative having a formula

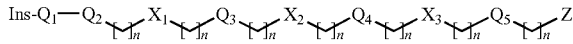

wherein Ins is a parent insulin moiety and $Q_1$-$Q_2$-$[CH_2]_n$—$X_1$—$[CH_2]_n$-$Q_3$-$[CH_2]_n$—$X_2$—$[CH_2]_n$-$Q_4$-$[CH_2]_n$—$X_3$—$[CH_2]_n$-$Q_5$-$[CH_2]_n$—Z is a substituent and where the Ins is attached to the substituent via an amide bond between the α-amino group of the N-terminal amino acid residue of the B chain of Ins or an ε-amino group of a Lys residue present in the A or B chain of Ins and a CO group in $Q_1$ or $Q_2$ of the substituent;

each n is independently 0, 1, 2, 3, 4, 5 or 6;

$Q_1$, $Q_2$, $Q_3$, $Q_4$ and $Q_5$, independently of each other can be:
  an amino acid residue, which residue forms, with its carboxylic acid group, an amide group together with the α-amino group of the N-terminal amino acid residue of the B chain of Ins or together with the ε-amino group of a Lys residue present in the A or B chain of Ins, or
  a chain composed of two, three or four α-amino acid residues as specified above linked together via amide bonds, which chain—via an amide bond—is linked to the α-amino group of the N-terminal amino acid residue of the B chain of Ins or to the ε-amino group of a Lys residue present in the A or B chain of Ins, or —CO—(CH$_2$)$_p$—NR$^1$—(CH$_2$)$_p$—, where each p is independently 1, 2, 3, 4, 5, or 6; and where R$^1$ can be H, —CH$_3$ or —(CH$_2$)$_{1-6}$—CH$_3$;

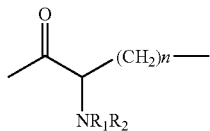

where n=1-6, and where R$^1$ and R$^2$, independently of each other can be H, —CH$_3$ or —(CH$_2$)$_{1-6}$—CH$_3$

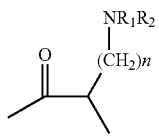

where n=1-6, and where R$^1$ and R$^2$, independently of each other can be H, —CH$_3$ or —(CH$_2$)$_{1-6}$—CH$_3$
—CO—(CH$_2$)$_p$—Ar—(CH$_2$)$_p$—, where Ar can be arylene or heteroarylene, which is substituted with at least one of the following groups consisting of —NR$^1$R$^2$, —(CH$_2$)$_p$—NR$^1$R$^2$— and Ar may also be substituted with one or two groups selected from the group consisting of —CH$_3$, —(CH$_2$)$_{1-6}$—CH$_3$, where each p is independently 1, 2, 3, 4, 5, or 6, and where R$^1$ and R$^2$, independently of each other can be H, —CH$_3$ or —(CH$_2$)$_{1-6}$—CH$_3$;

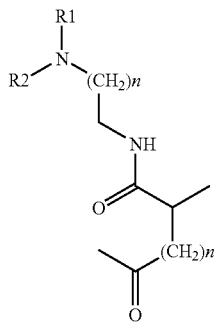

where n=1-6 and where R$^1$ and R$^2$, independently of each other can be H, —CH$_3$ or —(CH$_2$)$_{1-6}$—CH$_3$
—(CH$_2$)$_m$— where m is an integer in the range of 6 to 32;
a divalent hydrocarbon chain comprising 1, 2 or 3 —CH═CH— groups and a number of —CH$_2$— groups sufficient to give a total number of carbon atoms in the chain in the range of 4 to 32;
—CO—((CR$^5$R$^6$)$_{1-6}$—NH—CO)—;
—(CO—(CR$^5$R$^6$)$_{1-6}$—CO—NH)$_{1-4}$—, where R$^5$ independently can be H, —CH$_3$,—(CH$_2$)$_{1-6}$CH$_3$ or —CONH$_2$ and R$^6$ independently can be H, —CH$_3$,—(CH$_2$)$_{1-6}$CH$_3$;
—CO—(CH$_2$)$_{0-3}$—Ar—(CH$_2$)$_{0-3}$— where Ar can be arylene or heteroarylene, which may be substituted with one or two groups selected from the group consisting of —CH$_3$, —(CH$_2$)$_{1-6}$—CH$_3$, —NR$^1$R$^2$, —CONR$^1$R$^2$ or —SO$_2$NR$^1$R$^2$, where R$^1$ and R$^2$, independently of each other can be H, —CH$_3$ or —(CH$_2$)$_{1-6}$—CH$_3$;

(CH$_2$CH$_2$O)$_y$—; (CH$_2$CH$_2$CH$_2$O)$_y$—; (CH$_2$CH$_2$CH$_2$CH$_2$O)$_y$—; (CH$_2$CH$_2$OCH$_2$CH$_2$CH$_2$CH$_2$O)$_y$— or (CH$_2$CH$_2$CH$_2$OCH$_2$CH$_2$CH$_2$CH$_2$O)$_y$—;
—(CH$_2$OCH$_2$)$_y$— where y is 1-20;
arylene or heteroarylene, which may be substituted with one or two groups selected from the group consisting of —CH$_3$, —(CH$_2$)$_{1-6}$—CH$_3$, —CONR$^1$R$^2$ or —SO$_2$NR$^1$R$^2$, where R$^1$ and R$^2$, independently of each other can be H, —CH$_3$ or —(CH$_2$)$_{1-6}$—CH$_3$; or
a chain of the formula

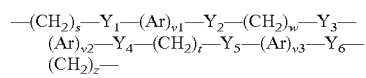

wherein Ar is defined as above, Y$_1$-Y$_6$ independently of each other can be O, S, S═O, SO$_2$ or a bond; where s, w, t and z independently of each other are zero or an integer from 1 to 10 so that the sum of s, w, t and z is in the range from 4 to 30, and v$_1$, v$_2$, and v$_3$ independently of each other can be zero or 1 with the proviso that Y$_1$-Y$_6$ do not link to each other and that the structure —O—(CH$_2$)$_1$—O— does not occur; or
a bond;
with the proviso that at least one of Q$_1$-Q$_5$ is not a bond;
X$_1$, X$_2$ and X$_3$ are independently of each other
O;
—C═O
a bond;
NCOR$^1$, where R$^1$ can be H, —CH$_3$ or —(CH$_2$)$_{1-6}$—CH$_3$; or

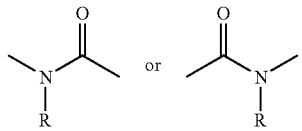

where R is hydrogen, C$_{1-3}$-alkyl, C$_{2-3}$-alkenyl or C$_{2-3}$-alkynyl;
with the proviso that
X$_1$, X$_2$ and X$_3$ cannot bind to Z and
when X$_1$, X$_2$ and X$_3$ are O, then X$_1$, X$_2$ and X$_3$ do not bind directly to O in Q$_1$, Q$_2$, Q$_3$, Q$_4$, and Q$_5$
and
Z is:
—COOH;
—CO-Asp;
—CO-Glu;
—CO-Gly;
—CO-Sar;
—CH(COOH)$_2$,
—N(CH$_2$COOH)$_2$;
—SO$_3$H
—OSO$_3$H
—OPO3H$_2$
—PO$_3$H$_2$
-tetrazol-5-yl
—O—W$_1$ or
—W$_1$
where W$_1$ is arylene or heteroarylene, which may be substituted with one or two groups selected from the group consisting of tetrazo-5-lyl, —COOH, —SO$_3$H, —(CH$_2$)$_{1-6}$—SO$_3$H, —(CH$_2$)$_{1-6}$—O—PO$_3$H$_2$, —CONR$^3$R$^4$ or —SO$_2$NR$^3$R$^4$, where R$^3$ and R$^4$, independently of each other can be H, —(CH$_2$)$_{1-6}$—SO$_3$H, or —(CH$_2$)$_{1-6}$—O—PO$_3$H$_2$;
and any Zn$^{2+}$ complex thereof, provided that at least one amine or positively charged amino acid is present in the substituent.

2. An insulin derivative according to paragraph 1 having a formula:

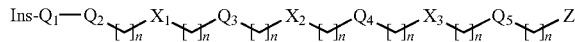

wherein Ins is a parent insulin moiety and $Q_1$-$Q_2$-$[CH_2]_n$—$X_1$—$[CH_2]_n$-$Q_3$-$[CH_2]_n$—$X_2$—$[CH_2]_n$-$Q_4$-$[CH_2]_n$—$X_3$—$[CH_2]_n$-$Q_5$-$[CH_2]_n$—Z is a substituent and where the Ins is attached to the substituent via an amide bond between the α-amino group of the N-terminal amino acid residue of the B chain of Ins or an ε-amino group of a Lys residue present in the A or B chain of Ins and a CO group in $Q_1$ or $Q_2$ of the substituent;

each n is independently 0, 1, 2, 3, 4, 5 or 6;

$Q_1$ is:
an amino acid residue, which residue forms, with its carboxylic acid group, an amide group together with the α-amino group of the N-terminal amino acid residue of the B chain of Ins or together with the ε-amino group of a Lys residue present in the A or B chain of Ins, or a chain composed of two, three or four α-amino acid residues as specified above linked together via amide bonds, which chain—via an amide bond—is linked to the α-amino group of the N-terminal amino acid residue of the B chain of Ins or to the ε-amino group of a Lys residue present in the A or B chain of Ins, or a bond $Q_2$ is:
—CO—$(CH_2)_p$—$NR^1$—$(CH_2)_p$—, where each p is independently 1, 2, 3, 4, 5, or 6; and where $R^1$ can be H, —$CH_3$ or —$(CH_2)_{1-6}$—$CH_3$;

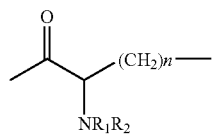

where n=1-6, and where $R^1$ and $R^2$, independently of each other can be H, —$CH_3$ or —$(CH_2)_{1-6}$—$CH_3$

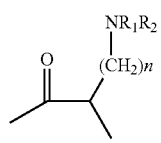

where n=1-6, and where $R^1$ and $R^2$, independently of each other can be H, —$CH_3$ or —$(CH_2)_{1-6}$—$CH_3$ —CO—$(CH_2)_p$—Ar—$(CH_2)_p$—, where Ar can be arylene or heteroarylene, which is substituted with at least one of the following groups consisting of —$NR^1R^2$, —$(CH_2)_p$—$NR^1R^2$— and Ar may also be substituted with one or two groups selected from the group consisting of —$CH_3$, —$(CH_2)_{1-6}$—$CH_3$, where each p is independently 1, 2, 3, 4, 5, or 6, and where $R^1$ and $R^2$, independently of each other can be H, —$CH_3$ or —$(CH_2)_{1-6}$—$CH_3$;

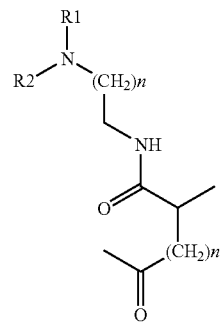

where n=1-6 and where $R^1$ and $R^2$, independently of each other can be H, —$CH_3$ or —$(CH_2)_{1-6}$—$CH_3$ a bond $Q_3$, $Q_4$, and $Q_5$ independently of each other can be
—$(CH_2)_m$— where m is an integer in the range of 6 to 32;
a divalent hydrocarbon chain comprising 1, 2 or 3 —CH=CH— groups and a number of —$CH_2$— groups sufficient to give a total number of carbon atoms in the chain in the range of 4 to 32;

—CO—$((CR^5R^6)_{1-6}$—NH—CO)—;

—(CO—$(CR^5R^6)_{1-6}$—CO—NH$)_{1-4}$—, where $R^5$ independently can be H, —$CH_3$,—$(CH_2)_{1-6}CH_3$ or —$CONH_2$ and $R^6$ independently can be H, —$CH_3$, —$(CH_2)_{1-6}$—$CH_3$;    —CO—$(CH_2)_{0-3}$—Ar—$(CH_2)_{0-3}$— where Ar can be arylene or heteroarylene, which may be substituted with one or two groups selected from the group consisting of —$CH_3$, —$(CH_2)_{1-6}$—$CH_3$, —$NR^1R^2$, —$CONR^1R^2$ or —$SO_2NR^1R^2$, where $R^1$ and $R^2$, independently of each other can be H, —$CH_3$ or —$(CH_2)_{1-6}$—$CH_3$;

$(CH_2CH_2O)_y$—;    $(CH_2CH_2CH_2O)_y$—;    $(CH_2CH_2CH_2CH_2O)_y$—;    $(CH_2CH_2OCH_2CH_2CH_2CH_2O)_y$— or $(CH_2CH_2CH_2OCH_2CH_2CH_2CH_2O)_y$—;

—$(CH_2OCH_2)_y$— where y is 1-20;

arylene or heteroarylene, which may be substituted with one or two groups selected from the group consisting of —$CH_3$, —$(CH_2)_{1-6}$—$CH_3$, —$CONR^1R^2$ or —$SO_2NR^1R^2$, where $R^1$ and $R^2$, independently of each other can be H, —$CH_3$ or —$(CH_2)_{1-6}$—$CH_3$; or a chain of the formula —$(CH_2)_s$—$Y_1$—$(Ar)_{v1}$—$Y_2$—$(CH_2)_w$—$Y_3$—$(Ar)_{v2}$—$Y_4$—$(CH_2)_t$—$Y_5$—$(Ar)_{v3}$—$Y_6$—$(CH_2)_z$— wherein Ar is defined as above, $Y_1$-$Y_6$ independently of each other can be O, S, S=O, $SO_2$ or a bond; where s, w, t and z independently of each other are zero or an integer from 1 to 10 so that the sum of s, w, t and z is in the range from 4 to 30, and $v_1$, $v_2$, and $v_3$ independently of each other can be zero or 1 with the proviso that $Y_1$-$Y_6$ do not link to each other and that the structure —O—$(CH_2)_1$—O— does not occur; or a bond;

with the proviso that at least one of $Q_3$-$Q_5$ is not a bond;

$X_1$, $X_2$ and $X_3$ are independently of each other
O;
—C=O
a bond;
$NCOR^1$, where $R^1$ can be H, —CH, or —$(CH_2)_{1-6}$—$CH_3$; or

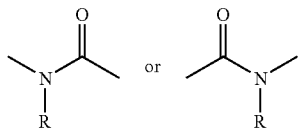 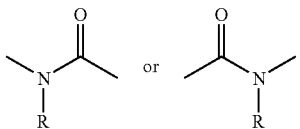

where R is hydrogen, $C_{1-3}$-alkyl, $C_{2-3}$-alkenyl or $C_{2-3}$-alkynyl;

with the proviso that $X_1$, $X_2$ and $X_3$ cannot bind to Z and when $X_1$, $X_2$ and $X_3$ are O, then $X_1$, $X_2$ and $X_3$ do not bind directly to O in $Q_3$, $Q_4$, and $Q_5$ and Z is:
- —COOH;
- CO-Asp;
- —CO-Glu;
- —CO-Gly;
- —CO-Sar;
- —CH(COOH)$_2$,
- —N(CH$_2$COOH)$_2$;
- —SO$_3$H
- —OSO$_3$H
- —OPO$_3$H$_2$
- —PO$_3$H$_2$
- -tetrazol-5-yl
- —O—W$_1$ or
- —W$_1$ where $W_1$ is arylene or heteroarylene, which may be substituted with one or two groups selected from the group consisting of tetrazo-5-lyl, —COOH, —SO$_3$H, —(CH$_2$)$_{1-6}$—SO$_3$H, —(CH$_2$)$_{1-6}$—O—PO$_3$H$_2$, —CONR$^3$R$^4$ or —SO$_2$NR$^3$R$^4$, where R$^3$ and R$^4$, independently of each other can be H, —(CH$_2$)$_{1-6}$—SO$_3$H, or —(CH$_2$)$_{1-6}$—O—PO$_3$H$_2$;

and any Zn$^{2+}$ complex thereof, provided that at least one amine or positively charged amino acid is present in the substituent.

3. Insulin derivative according to paragraphs 1-2, wherein $Q_1$ is selected from the group consisting of lysine, arginine, homoarginine, DAP, DAB and ornithine.

4. Insulin derivative according to paragraphs 1-2, wherein $Q_1$ is a bond

5. Insulin derivative according to paragraphs 1-4, wherein $Q_2$ is —CO—(CH$_2$)$_2$—NH—(CH$_2$)$_2$—, —CO—CH$_2$—NH—CH$_2$— or

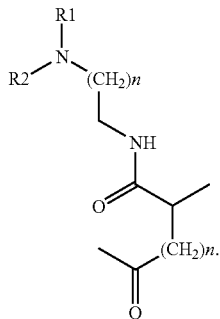

6. Insulin derivative according to paragraphs 1-5, wherein $X_1$, $X_2$ and $X_3$ are independently of each other are:
- O;
- —C=O 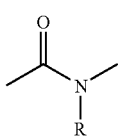
- a bond;
- NCOR$^1$, where R$^1$ can be H, —CH$_3$ or —(CH$_2$)$_{1-6}$—CH$_3$; or where R is hydrogen, $C_{1-3}$-alkyl, $C_{2-3}$-alkenyl or $C_{2-3}$-alkynyl;

with the proviso that $X_1$, $X_2$ and $X_3$ cannot bind to Z and when $X_1$, $X_2$ and $X_3$ are O, then $X_1$, $X_2$ and $X_3$ do not bind directly to O in $Q_3$, $Q_4$, and $Q_5$ 7. Insulin derivative according to paragraphs 1-6, wherein $X_1$ is

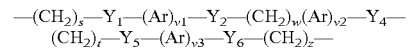

where R is hydrogen.

8. Insulin derivative according to paragraphs 1-7, wherein $Q_3$ is —(CH$_2$)$_m$— where m is an integer in the range of 6 to 32 or from 8 to 20.

9. Insulin derivative according to paragraph 8, where m is 12, 13, 14, 15 or 16.

10. Insulin derivative according to paragraphs 1-9, wherein $Q_4$, $Q_5$, $X_2$ and $X_3$ are bonds and all n are zero.

11. Insulin derivative according to any of paragraphs 1-10, wherein Z is —COOH.

12. Insulin derivative according to paragraphs 1-7, wherein $Q_3$ is a bond.

13. Insulin derivative according to paragraphs 1-7 or 12, wherein $Q_4$ is a divalent hydrocarbon chain comprising 1, 2 or 3 —CH=CH— groups and a number of —CH$_2$— groups sufficient to give a total number of carbon atoms in the chain in the range of 4 to 32.

14. Insulin derivative according to paragraphs 1-7 or 12, wherein $Q_4$ is

—(CH$_2$)$_s$—Y$_1$—(Ar)$_{v1}$—Y$_2$—(CH$_2$)$_w$(Ar)$_{v2}$—Y$_4$—(CH$_2$)$_t$—Y$_5$—(Ar)$_{v3}$—Y$_6$—(CH$_2$)$_z$— wherein Ar is defined as above, $Y_1$-$Y_6$ independently of each other can be O, S, S=O, SO$_2$ or a bond; where s, w, t and z independently of each other are zero or an integer from 1 to 10 so that the sum of s, w, t and z is in the range from 4 to 30, and $v_1$, $v_2$, and $v_3$ independently of each other can be zero or 1 with the proviso that $Y_1$-$Y_6$ do not link to each other and that the structure —O—(CH$_2$)$_1$—O— does not occur.

15. Insulin derivative according to any of paragraphs 1-7 and 14, wherein at least two of $v_1$, $v_2$, or $v_3$ are zero.

16. Insulin derivative according to any of paragraphs 1-7 and 14-15, wherein $Y_1$-$Y_6$ are bonds.

17. Insulin derivative according to any of paragraphs 1-7 and 14-15, wherein at least one of $Y_1$-$Y_6$ are O or S.

18. Insulin derivative according to any of paragraphs 1-7 and 14-15 and 17, wherein $Y_1$ is O or S and $v_1$ is one.

19. Insulin derivative according to any of paragraphs 1-7 and 14-18, wherein s is 6, 7, 8, 9 or 10.

20. Insulin derivative according to any of paragraphs 1-7 and 14-19, wherein Ar is $C_6H_4$.

21. Insulin derivative according to any of paragraphs 1-7 and 13-20, wherein $X_1$, $X_2$, $X_3$, and $Q_5$ are bonds and all n are zero.

22. Insulin derivative according to any of paragraphs 1-7, wherein one of $Q_3$, $Q_4$, or $Q_5$ is (CH$_2$CH$_2$O)$_y$—; (CH$_2$CH$_2$CH$_2$O)$_y$—; (CH$_2$CH$_2$CH$_2$CH$_2$O)$_y$—;

$(CH_2CH_2OCH_2CH_2CH_2CH_2O)_y$— or $(CH_2CH_2CH_2OCH_2CH_2CH_2CH_2O)_y$—; —$(CH_2OCH_2)_y$— where y is 1-20.

23. Insulin derivative according to paragraph 1-7 and 22, wherein one of $Q_3$, $Q_4$, or $Q_5$ is $(CH_2CH_2O)$— or $(CH_2CH_2OCH_2CH_2CH_2CH_2O)_y$ wherein y is in the range of 1-12, 2-4 or 2-3

24. Insulin derivative according to paragraph 1-7 and 22-23, wherein y is 1.

25. Insulin derivative according to any of paragraphs 1-7 and 22-24, wherein n is 0, 1, 2 or 3.

26. Insulin derivative according to any of paragraphs 1-7 and 12-25, wherein Z is —COOH.

27. Insulin derivative according to any of the preceding paragraphs, wherein the substituent is attached to the ε-amino group of a Lys residue present in the A or B chain of the parent insulin.

28. Insulin derivative according to any of the preceding paragraphs, wherein the substituent is attached to the ε-amino group of the Lys residue in position B29 present in the B chain of the parent insulin.

29. Insulin derivative according to any of the preceding paragraphs, wherein the parent insulin is human insulin or porcine insulin.

30. Insulin derivative according to paragraphs 1-28, wherein the parent insulin is an insulin analogue.

31. Insulin derivative according to any of the preceding paragraphs, wherein the amino acid residue at position B30 of the parent insulin is Lys or has been deleted.

32. Insulin derivative according to paragraphs 1-28 and 30-31, wherein the substituent is attached to the ε-amino group of the Lys residue in position B29 in desB30 human insulin 33. Insulin derivative according to paragraphs 1-28 and 30-32, wherein the parent insulin is AspB28 human insulin, GlyA21 human insulin or GlyA21desB30 human insulin, GlyA21ArgB31ArgB32 human insulin, LysB28ProB29 human insulin, ThrB29LysB30 human insulin or LysB3GluB29 human insulin.

34. A zinc complex of an insulin derivative according to any one of the preceding paragraphs wherein two zinc ions, three zinc ions, four zinc ions, five zinc ions, six zinc ions, seven zinc ions, eight zinc ions, nine zinc ions or ten zinc ions are bound per six molecules of insulin derivative.

35. A pharmaceutical composition for the treatment of diabetes in a patient in need of such treatment, comprising a therapeutically effective amount of an insulin derivative according to paragraphs 1-33 or a zinc complex according to paragraph 34.

36. A pharmaceutical composition according to paragraph 35, wherein the composition comprises one or more pharmaceutically acceptable excipients.

37. A pharmaceutical composition according to paragraphs 35-36, wherein the composition comprises an insulin analogue which has a rapid onset of action.

38. A pharmaceutical composition according to paragraphs 35-37, wherein the rapid acting insulin analogue is selected from the group consisting of AspB28 human insulin; LysB28ProB29 human insulin and LysB3GluB29 human insulin.

39. A method of treating diabetes in a patient in need of such a treatment by the use of a therapeutically effective amount of an insulin derivative according to paragraphs 1-33, a zinc complex according to paragraph 34 or a pharmaceutical composition according to paragraphs 35-38.

40. A method according to paragraph 39 for pulmonary treatment of diabetes.

41. Insulin derivative as defined in the examples.

The insulin derivative according to the invention and the rapid acting insulin analogue can be mixed in a ratio from about 90/10%; about 70/30% or about 50/50%.

In one aspect, the invention relates to a pharmaceutical composition comprising an insulin derivative according to the invention which is soluble at physiological pH values.

In one aspect, the invention relates to a pharmaceutical composition comprising an insulin derivative according to the invention which is soluble at pH values in the interval from about 6.5 to about 8.5.

In one aspect, the invention relates to a pharmaceutical composition with a prolonged profile of action which comprises an insulin derivative according to the invention.

In one aspect, the invention relates to a pharmaceutical composition which is a solution containing from about 120 nmol/ml to about 2400 nmol/ml, from about 400 nmol/ml to about 2400 nmol/ml, from about 400 nmol/ml to about 1200 nmol/ml, from about 600 nmol/ml to about 2400 nmol/ml, or from about 600 nmol/ml to about 1200 nmol/ml of an insulin derivative according to the invention or of a mixture of the insulin derivative according to the invention with a rapid acting insulin analogue.

The starting product for the acylation, the parent insulin or insulin analogue or a precursor thereof can be produced by either well-know peptide synthesis or by well known recombinant production in suitable transformed microorganisms. Thus the insulin starting product can be produced by a method which comprises culturing a host cell containing a DNA sequence encoding the polypeptide and capable of expressing the polypeptide in a suitable nutrient medium under conditions permitting the expression of the peptide, after which the resulting peptide is recovered from the culture.

The medium used to culture the cells may be any conventional medium suitable for growing the host cells, such as minimal or complex media containing appropriate supplements. Suitable media are available from commercial suppliers or may be prepared according to published recipes (e.g. in catalogues of the American Type Culture Collection). The peptide produced by the cells may then be recovered from the culture medium by conventional procedures including separating the host cells from the medium by centrifugation or filtration, precipitating the proteinaceous components of the supernatant or filtrate by means of a salt, e.g. ammonium sulphate, purification by a variety of chromatographic procedures, e.g. ion exchange chromatography, gel filtration chromatography, affinity chromatography, or the like, dependent on the type of peptide in question.

The DNA sequence encoding the parent insulin may suitably be of genomic or cDNA origin, for instance obtained by preparing a genomic or cDNA library and screening for DNA sequences coding for all or part of the polypeptide by hybridisation using synthetic oligonucleotide probes in accordance with standard techniques (see, for example, Sambrook, J, Fritsch, E F and Maniatis, T, *Molecular Cloning: A Laboratory Manual*, Cold Spring Harbor Laboratory Press, New York, 1989). The DNA sequence encoding the parent insulin may also be prepared synthetically by established standard methods, e.g. the phosphoamidite method described by Beaucage and Caruthers, *Tetrahedron Letters* 22 (1981), 1859-1869, or the method described by Matthes et al., *EMBO Journal* 3 (1984), 801-805. The DNA sequence may also be prepared by polymerase chain reaction using specific primers, for instance as described in U.S. Pat. No. 4,683,202 or Saiki et al., *Science* 239 (1988), 487-491.

The DNA sequence may be inserted into any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The vector is for example an expression vector in which the DNA sequence encoding the parent insulin is operably linked to additional segments required for transcription of the DNA, such as a promoter. The promoter may be any DNA sequence which shows transcriptional activity in the host cell of choice and may be derived from genes encoding proteins either homologous or heterologous to the host cell. Examples of suitable promoters for directing the transcription of the DNA encoding the parent insulin in a variety of host cells are well known in the art, cf. for instance Sambrook et al., supra.

The DNA sequence encoding the parent insulin may also, if necessary, be operably connected to a suitable terminator, polyadenylation signals, transcriptional enhancer sequences, and translational enhancer sequences. The recombinant vector of the invention may further comprise a DNA sequence enabling the vector to replicate in the host cell in question.

The vector may also comprise a selectable marker, e.g. a gene the product of which complements a defect in the host cell or one which confers resistance to a drug, e.g. ampicillin, kanamycin, tetracyclin, chloramphenicol, neomycin, hygromycin or methotrexate.

To direct a peptide of the present invention into the secretory pathway of the host cells, a secretory signal sequence (also known as a leader sequence, prepro sequence or pre sequence) may be provided in the recombinant vector. The secretory signal sequence is joined to the DNA sequence encoding the peptide in the correct reading frame. Secretory signal sequences are commonly positioned 5' to the DNA sequence encoding the peptide. The secretory signal sequence may be that normally associated with the peptide or may be from a gene encoding another secreted protein.

The procedures used to ligate the DNA sequences coding for the parent insulin, the promoter and optionally the terminator and/or secretory signal sequence, respectively, and to insert them into suitable vectors containing the information necessary for replication, are well known to persons skilled in the art (cf., for instance, Sambrook et al., supra).

The host cell into which the DNA sequence or the recombinant vector is introduced may be any cell which is capable of producing the present peptide and includes bacteria, yeast, fungi and higher eukaryotic cells. Examples of suitable host cells well known and used in the art are, without limitation, *E. coli, Saccharomyces cerevisiae*, or mammalian BHK or CHO cell lines.

The parent insulin molecule is then converted into the insulin derivatives of the invention by introducing of the relevant substituent in either the B1 position or in the chosen Lys position in the B-chain. The substituent can be introduced by any convenient method and many methods are disclosed in the prior art for acylation of an amino group. More details will appear from the following examples.

Pharmaceutical Compositions

The insulin derivatives of this invention of the claimed formula can, for example, be administered subcutaneously, orally, or pulmonary.

For subcutaneous administration, the compounds of the formula are formulated analogously with the formulation of known insulins. Furthermore, for subcutaneous administration, the compounds of the formula are administered analogously with the administration of known insulins and, generally, the physicians are familiar with this procedure.

The insulin derivatives of this invention may be administered by inhalation in a dose effective manner to increase circulating insulin levels and/or to lower circulating glucose levels. Such administration can be effective for treating disorders such as diabetes or hyperglycemia. Achieving effective doses of insulin requires administration of an inhaled dose of insulin derivative of this invention of more than about 0.5 µg/kg to about 50 µg/kg. A therapeutically effective amount can be determined by a knowledgeable practitioner, who will take into account factors including insulin level, blood glucose levels, the physical condition of the patient, the patient's pulmonary status, or the like.

Administration by inhalation can result in pharmacokinetics comparable to subcutaneous administration of insulins. Different inhalation devices typically provide similar pharmacokinetics when similar particle sizes and similar levels of lung deposition are compared.

According to the invention, insulin derivative of this invention may be delivered by any of a variety of inhalation devices known in the art for administration of a therapeutic agent by inhalation. These devices include metered dose inhalers, nebulizers, dry powder generators, sprayers, and the like. Insulin derivative of this invention is delivered by a dry powder inhaler or a sprayer. There are a several desirable features of an inhalation device for administering insulin derivative of this invention. For example, delivery by the inhalation device is advantageously reliable, reproducible, and accurate. The inhalation device should deliver small particles, for example, less than about 10 µm, for example about 1-5 µm, for good respirability. Some specific examples of commercially available inhalation devices suitable for the practice of this invention are Turbohaler™ (Astra), Rotahaler® (Glaxo), Diskus® (Glaxo), Spiros™ inhaler (Dura), devices marketed by Inhale Therapeutics, AERx™ (Aradigm), the Ultravent® nebulizer (Mallinckrodt), the Acorn II® nebulizer (Marquest Medical Products), the Ventolin® metered dose inhaler (Glaxo), the Spinhaler® powder inhaler (Fisons), or the like.

As those skilled in the art will recognize, the formulation of insulin derivative of this invention, the quantity of the formulation delivered, and the duration of administration of a single dose depend on the type of inhalation device employed. For some aerosol delivery systems, such as nebulizers, the frequency of administration and length of time for which the system is activated will depend mainly on the concentration of insulin conjugate in the aerosol. For example, shorter periods of administration can be used at higher concentrations of insulin conjugate in the nebulizer solution. Devices such as metered dose inhalers can produce higher aerosol concentrations, and can be operated for shorter periods to deliver the desired amount of insulin conjugate. Devices such as powder inhalers deliver active agent until a given charge of agent is expelled from the device. In this type of inhaler, the amount of insulin derivative of this invention in a given quantity of the powder determines the dose delivered in a single administration.

The particle size of insulin derivative of this invention in the formulation delivered by the inhalation device is critical with respect to the ability of insulin to make it into the lungs, and into the lower airways or alveoli. The insulin derivative of this invention can be formulated so that at least about 10% of the insulin conjugate delivered is deposited in the lung, for example about 10 to about 20%, or more. It is known that the maximum efficiency of pulmonary deposition for mouth breathing humans is obtained with particle sizes of about 2 µm to about 3 µm. When particle sizes are above about 5 µm pulmonary deposition decreases substantially. Particle sizes below about 1 µm cause pulmonary deposition to decrease, and it becomes difficult to deliver particles with sufficient mass to be therapeutically effective. Thus, particles of the insulin derivative delivered by inhalation have a particle size less than about 10 µm, for example in the range of about 1 µm to about 5 µm. The formulation of the insulin derivative is selected to yield the desired particle size in the chosen inhalation device.

Advantageously for administration as a dry powder, an insulin derivative of this invention is prepared in a particulate form with a particle size of less than about 10 µm, for example about 1 to about 5 µm. The particle size is effective for delivery to the alveoli of the patient's lung. The dry powder is largely composed of particles produced so that a majority of the particles have a size in the desired range. Advantageously, at least about 50% of the dry powder is made of particles having a diameter less than about 10 µm. Such formulations can be achieved by spray drying, milling, or critical point condensation of a solution containing insulin conjugate and other desired ingredients. Other methods also suitable for generating particles useful in the current invention are known in the art.

The particles are usually separated from a dry powder formulation in a container and then transported into the lung of a patient via a carrier air stream. Typically, in current dry powder inhalers, the force for breaking up the solid is provided solely by the patient's inhalation. In another type of inhaler, air flow generated by the patient's inhalation activates an impeller motor which deagglomerates the particles.

Formulations of insulin derivatives of this invention for administration from a dry powder inhaler typically include a finely divided dry powder containing the derivative, but the powder can also include a bulking agent, carrier, excipient, another additive, or the like. Additives can be included in a dry powder formulation of insulin conjugate, for example, to dilute the powder as required for delivery from the particular powder inhaler, to facilitate processing of the formulation, to provide advantageous powder properties to the formulation, to facilitate dispersion of the powder from the inhalation device, to stabilize the formulation (for example, antioxidants or buffers), to provide taste to the formulation, or the like. Advantageously, the additive does not adversely affect the patient's airways. The insulin derivative can be mixed with an additive at a molecular level or the solid formulation can include particles of the insulin conjugate mixed with or coated on particles of the additive. Typical additives include mono-, di-, and polysaccharides; sugar alcohols and other polyols, such as, for example, lactose, glucose, raffinose, melezitose, lactitol, maltitol, trehalose, sucrose, mannitol, starch, or combinations thereof; surfactants, such as sorbitols, diphosphatidyl choline, or lecithin; or the like. Typically an additive, such as a bulking agent, is present in an amount effective for a purpose described above, often at about 50% to about 90% by weight of the formulation. Additional agents known in the art for formulation of a protein such as insulin analogue protein can also be included in the formulation.

A spray including the insulin derivatives of this invention can be produced by forcing a suspension or solution of insulin conjugate through a nozzle under pressure. The nozzle size and configuration, the applied pressure, and the liquid feed rate can be chosen to achieve the desired output and particle size. An electrospray can be produced, for example, by an electric field in connection with a capillary or nozzle feed. Advantageously, particles of insulin conjugate delivered by a sprayer have a particle size less than about 10 µm, for example in the range of about 1 µm to about 5 µm.

Formulations of insulin derivatives of this invention suitable for use with a sprayer will typically include the insulin derivative in an aqueous solution at a concentration of about 1 mg to about 20 mg of insulin conjugate per ml of solution. The formulation can include agents such as an excipient, a buffer, an isotonicity agent, a preservative, a surfactant, and, for example zinc. The formulation can also include an excipient or agent for stabilization of the insulin derivative, such as a buffer, a reducing agent, a bulk protein, or a carbohydrate. Bulk proteins useful in formulating insulin conjugates include albumin, protamine, or the like. Typical carbohydrates useful in formulating insulin conjugates include sucrose, mannitol, lactose, trehalose, glucose, or the like. The insulin derivative formulation can also include a surfactant, which can reduce or prevent surface-induced aggregation of the insulin conjugate caused by atomization of the solution in forming an aerosol. Various conventional surfactants can be employed, such as polyoxyethylene fatty acid esters and alcohols, and polyoxyethylene sorbitol fatty acid esters. Amounts will generally range between about 0.001 and about 4% by weight of the formulation.

Pharmaceutical compositions containing an insulin derivative according to the present invention may also be administered parenterally to patients in need of such a treatment. Parenteral administration may be performed by subcutaneous, intramuscular or intravenous injection by means of a syringe, optionally a pen-like syringe. Alternatively, parenteral administration can be performed by means of an infusion pump. Further options are to administer the insulin nasally or pulmonally, for example in compositions, powders or liquids, specifically designed for the purpose.

Injectable compositions of the insulin derivatives of the invention can be prepared using the conventional techniques of the pharmaceutical industry which involve dissolving and mixing the ingredients as appropriate to give the desired end product. Thus, according to one procedure, an insulin derivative according to the invention is dissolved in an amount of water which is somewhat less than the final volume of the composition to be prepared. An isotonic agent, a preservative and a buffer is added as required and the pH value of the solution is adjusted—if necessary—using an acid, e.g. hydrochloric acid, or a base, e.g. aqueous sodium hydroxide as needed. Finally, the volume of the solution is adjusted with water to give the desired concentration of the ingredients.

In a further aspect of the invention the buffer is selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid or mixtures thereof. Each one of these specific buffers constitutes an alternative aspect of the invention.

In a further aspect of the invention the formulation further comprises a pharmaceutically acceptable preservative which may be selected from the group consisting of phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, bronopol, benzoic acid, imidurea, chlorohexidine, sodium dehydroacetate, chlorocresol, ethyl p-hydroxybenzoate, benzethonium chloride, chlorphenesine (3p-chlorphenoxypropane-1,2-diol) or mixtures thereof. In a further aspect of the invention the preservative is present in a concentration from 0.1 mg/ml to 20 mg/ml. In a further aspect of the invention the preservative is present in a concentration from 0.1 mg/ml to 5 mg/ml. In a further aspect of the invention the preservative is present in a concentration from 5 mg/ml to 10 mg/ml. In a further aspect of the invention the preservative is present in a concentration from 10 mg/ml to 20 mg/ml. Each one of these specific preservatives constitutes an alternative aspect of the invention. The use of a preservative in pharmaceutical compositions is well-known to the skilled person. For convenience reference is made to Remington: *The Science and Practice of Pharmacy*, $19^{th}$ edition, 1995.

In a further aspect of the invention the formulation further comprises an isotonic agent which may be selected from the group consisting of a salt (e.g. sodium chloride), a sugar or sugar alcohol, an amino acid (e.g. glycine, L-histidine, arginine, lysine, isoleucine, aspartic acid, tryptophan, threonine), an alditol (e.g. glycerol (glycerine), 1,2-propanediol (propyleneglycol), 1,3-propanediol, 1,3-butanediol)polyethyleneglycol (e.g. PEG400), or mixtures thereof. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, soluble starch, hydroxyethyl starch and carboxymethylcellulose-Na may be used. In one aspect the sugar additive is sucrose. Sugar alcohol is defined as a C4-C8 hydrocarbon having at least one —OH group and includes, for example, mannitol, sorbitol, inositol, galactitol, dulcitol, xylitol, and arabitol. In one aspect the sugar alcohol additive is mannitol. The sugars or sugar alcohols mentioned above may be used individually or in combination. There is no fixed limit to the amount used, as long as the sugar or sugar alcohol is soluble in the liquid preparation and does not adversely effect the stabilizing effects achieved using the methods of the invention. In one aspect, the sugar or sugar alcohol concentration is between about 1 mg/ml and about 150 mg/ml. In a further aspect of the invention the isotonic agent is present in a concentration from 1 mg/ml to 50 mg/ml. In a further aspect of the invention the isotonic agent is present in a concentration from 1 mg/ml to 7 mg/ml. In a further aspect of the invention the isotonic agent is present in a concentration from 8 mg/ml to 24 mg/ml. In a further aspect of the invention the isotonic agent is present in a concentration from 25 mg/ml to 50 mg/ml. Each one of these specific isotonic agents constitutes an alternative aspect of the invention. The use of an isotonic agent in pharmaceutical compositions is well-known to the skilled person. For convenience reference is made to Remington: *The Science and Practice of Pharmacy*, 19$^{th}$ edition, 1995.

Typical isotonic agents are sodium chloride, mannitol, dimethyl sulfone and glycerol and typical preservatives are phenol, m-cresol, methyl p-hydroxybenzoate and benzyl alcohol.

Examples of suitable buffers are sodium acetate, glycylglycine, HEPES (4-(2-hydroxyethyl)-1-piperazineethanesulfonic acid) and sodium phosphate.

A composition for nasal administration of an insulin derivative according to the present invention may, for example, be prepared as described in European Patent No. 272097 (to Novo Nordisk A/S).

Compositions containing insulin derivatives of this invention can be used in the treatment of states which are sensitive to insulin. Thus, they can be used in the treatment of type 1 diabetes, type 2 diabetes and hyperglycaemia for example as sometimes seen in seriously injured persons and persons who have undergone major surgery. The optimal dose level for any patient will depend on a variety of factors including the efficacy of the specific insulin derivative employed, the age, body weight, physical activity, and diet of the patient, on a possible combination with other drugs, and on the severity of the state to be treated. It is recommended that the daily dosage of the insulin derivative of this invention be determined for each individual patient by those skilled in the art in a similar way as for known insulin compositions.

Where expedient, the insulin derivatives of this invention may be used in mixture with other types of insulin, e.g. insulin analogues with a more rapid onset of action. Examples of such insulin analogues are described e.g. in the European patent applications having the publication Nos. EP 214826 (Novo Nordisk A/S), EP 375437 (Novo Nordisk A/S) and EP 383472 (Eli Lilly & Co.).

The present invention is further illustrated by the following examples which, however, are not to be construed as limiting the scope of protection.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

EXAMPLES

Example 1

Synthesis of N$^{\epsilon B29}$-{3-[2-(16-Carboxyhexadecylcarbamoyl)ethylamino]propionyl}desB30 human insulin

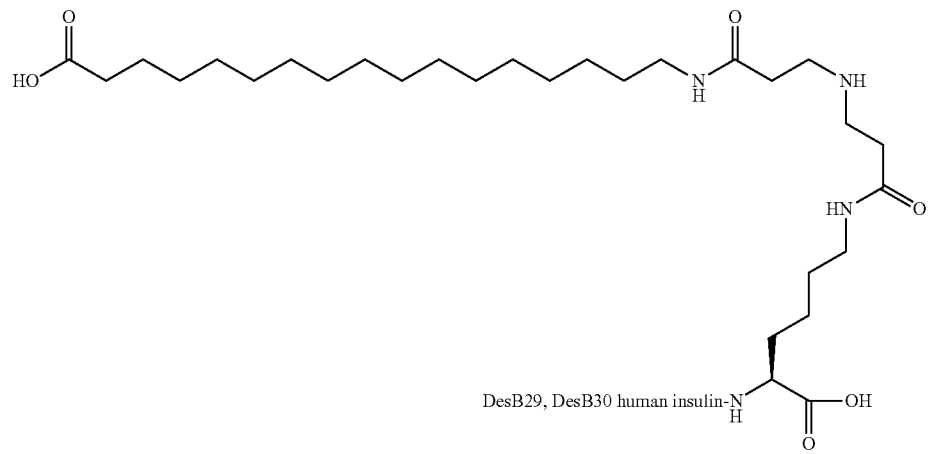

Step 1: 3-(2-Benzyloxycarbonylethylamino)propionic acid

3-Aminopropionic acid (5 g, 56 mmol) was added to ethanol (50 mL), and TEA (7.8 ml, 56 mmol) and water (50 mL) were added and the mixture was refluxed under nitrogen. Acrylic acid benzyl ester ((9.1 g, 56 mmol) and more ethanol (50 mL) were added, and the mixture was refluxed for 16 h. The sample was concentrated under vacuum, adding toluene and reevaporating twice to yield 17.5 grams (product plus TEA).

$^1$H-NMR (DMSO, 300 MHz) δ 7.12-7.40 (m, 5H), 4.49 (s, 2H), 2.98 (t, 4H), 2.42 (t, 4H) (plus TEA signals 2.79 and 1.08)

Step 2: 3-[(2-Benzyloxycarbonylethyl)tert-butoxycarbonylamino]propionic acid 3-(2-Benzyloxycarbonylethylamino) propionic acid (2 g, 7.2 mmol) was dissolved in DCM (20 mL) and di-tert-butyl-dicarbonate (3.5 g, 15.8 mmol) and TEA (2.59 mL, 18.6 mmol) were added. After 8 days, DCM (50 mL) was added and the solution was washed with water (75 mL) and 1 N HCl (30 ml). The aqueos washing were extracted with DCM (25 mL). The organic phases were pooled, dried over MgSO$_4$ and concentrated under vacuum. The compound was purified by flash chromatography (AcOEt/heptane) to yield 0.4 g.

$^1$H-NMR (DMSO, 300 MHz) δ 12.24 (br. 1H), 7.25-7.45 (m, 5H), 5.09 (s, 2H), 3.42 (t, 2H) 3.34 (t-br, 4H, theo. 2H), 2.58 (t, 2H), 2.41 (t, 2H)

Step 3: 17-Aminoheptadecanoic acid tert-butyl ester

Acetonitrile (10 mL) was added to octadecanedioic acid mono-tert-butyl ester (500 mg, 1.3 mmol) and TEA (0.226 mL, 1.6 mmol) was added. Diphenylphosphonic azide (0.37 g, 1.3 mmol) was added in a solution of acetonitrile (1 mL). The mixture was stirred at reflux for 2 h, and at RT for 16 h. The reaction was concentrated under vacuum, and suspended/dissolved in 1:2, AcOEt:heptane (2 mL) and applied to a dry bed of silica (2×4 cm dia). It was eluated with 1:2 AcOEt:heptane (2 mL) and 1:1 AcOEt:heptane (60 mL). The eluate was concentrated to dryness. The residue was partly suspended in THF (2 mL) and 1 N NaOH (2 mL) was added. The turbid solution/suspension was stirred for 1 h at RT. Water (15 mL) was added and this was extracted with AcOEt (2×25 mL), adding some brine to aid separation. The organic phase was washed with sat. NaCl, dried, filtered and conc. to dryness. To the residue was added 20% acetonitrile/water (15 mL), TFA (15-20 ul) and DMSO (1 mL). A filtration of the mixture failed, so the filter and the solution were extracted with DCM (2×60 mL). The organic extracts were concentrated to yield the crude product (0.14 g), LCMS: m/z: 342 (M+1)

Step 4: 17-{3-[(2-Benzyloxycarbonylethyl)tert-butoxycarbonylamino]propionylamino}heptadecanoic acid tert-butyl ester 3-[(2-Benzyloxycarbonylethyl) tert-butoxycarbonylamino]propionic acid (0.17 g, 0.48 mmol) was dissolved in DMF (2 mL) and HOBt (0.065 g, 0.48 mmol) and EDAC (0.093 g, 0.48 mmol) were added. The mixture was stirred for 30 min., and DIEA (0.083 mL, 0.48 mmol) was added and 17-aminoheptadecanoic acid tert-butyl ester (0.15 g, 0.44 mmol) dissolved in THF (3 mL)+DMF (0.5 mL) was added. The reaction was stirred for 2 days. The reaction was concentrated and the residue was dissolved in AcOEt (50 mL) and washed with 0.2 N HCl (2×15 mL). The organic phase was dried over MgSO$_4$ and concentrated under vacuum. The product was purified by flash chromatography (Silica) eluting with AcOEt/Heptane (1:1, 7:3, 8:2) then DCM, DCM:methanol (8:2) and 5% AcOH in DCM. The appropriate fractions were pooled and concentrated under vacuum. The residue was dissolved in DCM. Silica was added and the product was concentrated onto the silica under vacuum. The silica was used in another flash chromatography, eluting with AcOEt/heptane (3:7 and 1:1). The appropriate fractions were pooled and concentrated under vacuum to yield 135 mg.

LCMS: m/z: 697 (M+23)

$^1$H-NMR (CDCl3, 300 MHz) δ 7.31-7.41 (m, 5H), 5.12 (s, 2H), 3.48 (m, 2H) 3.21 (m, 2H), 2.60 (t, 2H), 2.20 (t, 2H), 1.57 (m, 2H), 1.45 (m, 20H, 1.25 (m-br, 24H).

Step 5: 17-{3-[tert-Butoxycarbonyl (2-carboxyethyl)amino]propionylamino}heptadecanoic acid tert-butyl ester 17-{3-[(2-Benzyloxycarbonylethyl)tert-butoxycarbonylamino]propionylamino}heptadecanoic acid tert-butyl ester (0.135 g, 0.2 mmol) was dissolved in THF (10 mL) in a flask. The flask was filled with nitrogen and purged under vacuum several times. Pd/C, wet 10% (0.03 g) was added and the flask was equipped with a balloon filled with the mixture was stirred for 16 h. The mixture was filtered through a celite, eluting with THF. The filtrate was concentrated under vacuum. TLC indicated the reaction was not complete, so the process was repeated twice more. The filtrate was concentrated under vacuum to yield a yellow oil (0.12 g)

LCMS: m/z: 607 (M+23)

Step 6: 17-(3-{tert-Butoxycarbonyl[2-(2,5-dioxopyrrolidin-1-yloxycarbonyl)ethyl]amino}propionylamino)heptadecanoic acid tert-butyl ester 17-{3-[tert-Butoxycarbonyl (2-carboxyethyl)amino]propionylamino}heptadecanoic acid tert-butyl ester (0.122 g, 0.2 mmol) was dissolved in THF (5 mL). DIEA (39 ul) was added and the mixture was cooled to 0° C. TSTU (66 mg, 0.22 mmol) was added. The mixture was stirred at 0° C. for 30 min, then for 16 h at RT. The mixture was concentrated under vacuum. AcOEt (15 mL) and the solution was washed with 0.2 N HCl (5 ml) and sat. NaCl (5 ml), dried over MgSO$_4$, and dried under vacuum. The residue was purified by flash chromatography (silica) eluting with AcOEt/heptane (9:1) and AcOEt. The appropriate fractions were pooled and concentrated under vacuum to yield 58 mg.

LCMS: m/z: 682 (M+1)

Step 7: N$^{εB29}$-{3-[2-(16-Carboxyhexadecylcarbamoyl)ethylamino]propionyl}desB30 human insulin DesB30 insulin (126 mg, 0.022 mmol) was dissolved by adding 100 mM Na$_2$CO$_3$ (1.5 ml) and acetonitrile (1.5 ml) in a 10 ml round bottom-flask. 17-(3-{tert-Butoxycarbonyl[2-(2,5-dioxopyrrolidin-1-yloxycarbonyl)ethyl]amino}propionylamino)heptadecanoic acid tert-butyl ester (15 mg, 0.022 mmol) was added in acetonitrile (750 ul) and $Na_2CO_3$ (750 ul) was added so the final solution was 50:50 100 mM $Na_2CO_3$/acetonitrile. The solution was stirred at RT for 1 h. The solution was transferred to a 15 ml centrifuge tube, washing with Milli-Q water (6 ml). The solution was cooled on ice, and the pH was adjusted to 5.1 by adding 1N HCl, which lead to precipitation. The tube was centrifuged at 5000 rpm for 10 min at 10° C. The solvent was decanted from the solid. 95:5 TFA/water (2.5 ml) was added to the solid. The solution was poured into a RB-flask, washing with more 95:5 TFA/water (2.5 ml). The solution was stirred for 30 min at RT, and concentrated under vacuum. DCM was added and removed twice, and the flask was dried under vacuum at RT. The product was purified using ion exchange chromatography.

Column: Resource Q 6 ml
Buffer A: 15 mM TRIS, 30 mM ammoniumacetate, 50% v/v ethanol, pH 7.5 with AcOH.
Buffer B: 15 mM TRIS, 300 mM ammoniumacetate, 50% v/v ethanol, pH 7.5 with AcOH.
Elute with 4 ml/min. 2 CV buffer A then a gradient from 0-80% buffer B over 12 CV.

The appropriate fraction was diluted with water and acidified to pH 2. and loaded onto a resource RPC 3 ml column in 20% ethanol, 0.1% TFA and eluted with 50% ethanol, 0.1% TFA. The appropriate fractions were pooled, diluted with water and freeze dried to yield 15 mg.

LCMS: m/z: 1529.7 (M/4=1529.3)

Example 2

Synthesis of $N^{\epsilon B29}$-{3-[2-(14-Carboxytetradecylcarbamoyl)ethylamino]propionyl}desB30 human insulin

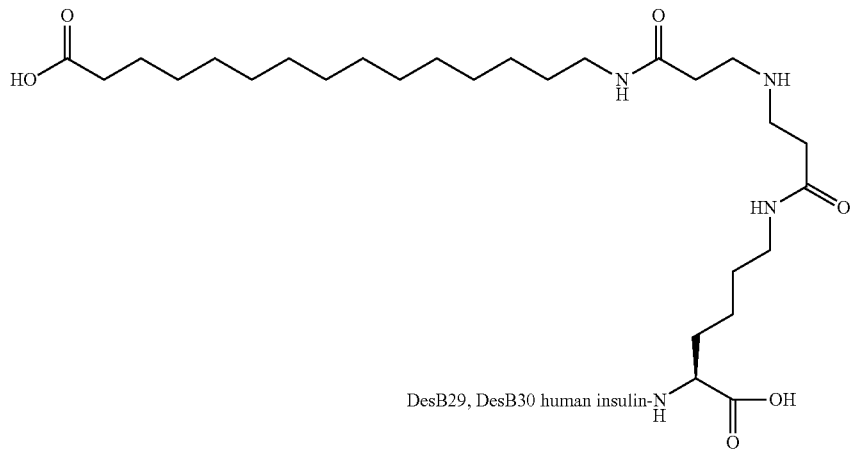

The title compound was prepared in analogous fashion to the methods described in Example 1, though the final product was purified using preparative HPLC (2 cm dia. $C_{18}$ column, acetonitrile/water/0.1% TFA)

LCMS: 1523.3 (M/4=1522.3)

Example 3

Synthesis of $N^{\epsilon B29}$-(2-{[(14-Carboxytetradecylcarbamoyl)methyl]amino}acetyl)desB30 human insulin

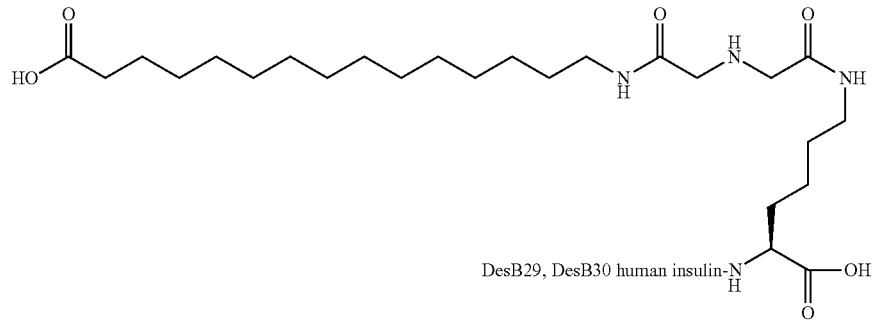

Step 1: (tert-Butoxycarbonylmethoxycarbonylmethylamino)acetic acid (tert-Butoxycarbonylcarboxymethylamino)acetic acid (9.5 g, 41 mmol) was dissolved in DMF and ADAC (7.78 g, 41 mmol) was added. The solution was stirred at RT for 1 h under nitrogen and MeOH (1.65 ml, 41 mmol) was added. The mixture was stirred for 4 h, and concentrated under vacuum. AcOEt (150 mL) was added, and the solution was washed with water (3×100 mL), dried over $Na_2SO_4$ and concentrated under vacuum to yield a colorless oil (9.15 g).

LCMS: m/z: 270.1 (M+23)

Step 2: 15-[2-(tert-Butoxycarbonyl methoxycarbonylmethyl amino)acetylamino]pentadecanoic acid tert-butyl ester 15-Aminopentadecanoic acid tert-butyl ester was prepared in analogous fashion to 17-aminoheptadecanoic acid tert-butyl ester, and was coupled to (tert-butoxycarbonyl-methoxycarbonylmethylamino) acetic acid in analogous fashion to the method described in Example 1, step 4.

Step 3: 15-[2-(tert-Butoxycarbonyl-carboxymethyl-amino)acetylamino]pentadecanoic acid tert-butyl ester 15-[2-(tert-Butoxycarbonyl methoxycarbonylmethyl amino)acetylamino]pentadecanoic acid tert-butyl ester (0.22 g, 0.405 mmol) was dissolved in THF (5 mL) and 1 N NaOH (0.405 mL) was added. The mixture was stirred under nitrogen for 16 h. The mixture was concentrated under vacuum. The residue was suspended in AcOEt (ca 25 mL) and water (15 mL) and AcOH (3 mL) were added. The organic phase was isolated and washed with water (15 mL)+AcOH (1 mL), water (15 mL) and dried over magnesium sulphate, and concentrated under vacuum.

The remaining steps were performed in analogous fashion to the methods used in example 1, and the final compound was purified first by preparative HPLC and then by ion exchange chromatography using a Resource Q 1 mL column and eluting from 0.25% ammonium acetate to 2.5% ammonium acetate (0.24% Tris, 42.5% ethanol, pH 7.5).

LCMS: m/z: 1516.55 (M/4=1515.3)

Example 4

Synthesis of $N^{\epsilon B29}$-[(S)-2-Amino-6-(15-carboxypentadecanoylamino)hexanoyl]desB30 human insulin Hexadecanedioic acid mono-tert-butyl ester can be activated with TSTU in similar fashion to the method described in Example 1, Step 6. The product can be reacted with Boc-Lys-OH in DMF at RT for 16 h. After concentrating under vacuum, AcOEt can be added the residue and the mixture can be washed with 0.2 N HCl. The organic phase is then dried over $MgSO_4$ and concentrated under vacuum to yield the crude product, 15-((S)-5-tert-Butoxycarbonylamino-5-carboxypentylcarbamoyl)pentadecanoic acid tert-butyl ester. This can either be used without further purification or purified by flash chromatography. This compound can be activated with TSTU in similar fashion to the method described in Example 1, Step 6 to yield 15-[(S)-5-tert-butoxycarbonylamino-5-(2,5-dioxopyrrolidin-1-yloxycarbonyl) pentylcarbamoyl]pentadecanoic acid tert-butyl ester, and this compound can be coupled to insulin and deprotected to yield the title compound as described in Example 1, Step 7 using prepatative HPLC to isolate the product.

Example 5

Synthesis of $N^{\epsilon B29}$-{(S)-2-Amino-3-[(S)-2-amino-3-(15-carboxypentadecanoylamino)propionylamino]propionyl}desB30 human insulin 15-[(S)-2-tert-Butoxycarbonylamino-2-(2,5-dioxo-pyrrolidin-1-yloxycarbonyl)ethylcarbamoyl]pentadecanoic acid tert-butyl ester can be prepared in similar fashion as that described for 15-[(S)-5-tert-butoxycarbonylamino-5-(2,5-dioxopyrrolidin-1-yloxycarbonyl)pentylcarbamoyl]pentadecanoic acid tert-butyl ester using (S)-3-amino-2-tert-butoxycarbonylamino propionic acid, and it can be reacted with (S)-3-amino-2-tert-butoxycarbonylamino propionic acid in DMF at RT for 16 h. After concentrating under vacuum, AcOEt can be added the residue and the mixture can be washed with 0.2 N HCl. The organic phase is then dried over $MgSO_4$ and concentrated under vacuum to yield the crude product, 15-[(S)-2-tert-butoxycarbonylamino-2-((S)-2-tert-butoxycarbonylamino-2-carboxyethylcarbamoyl)ethylcarbamoyl]pentadecanoic acid tert-butyl ester. This can either be used without further purification or purified by flash chromatography.

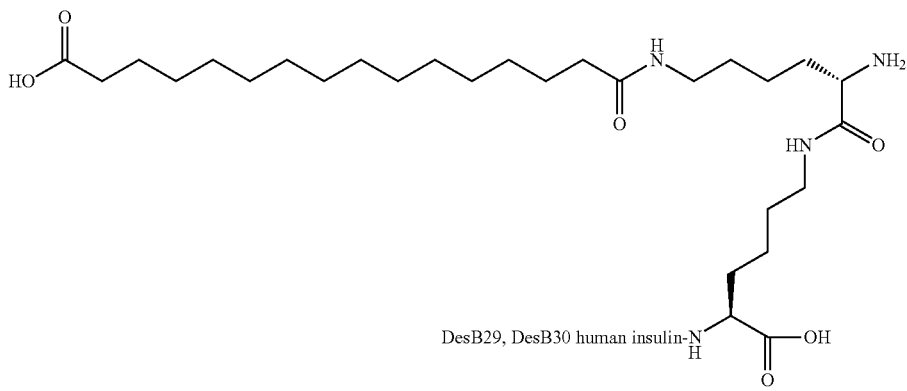

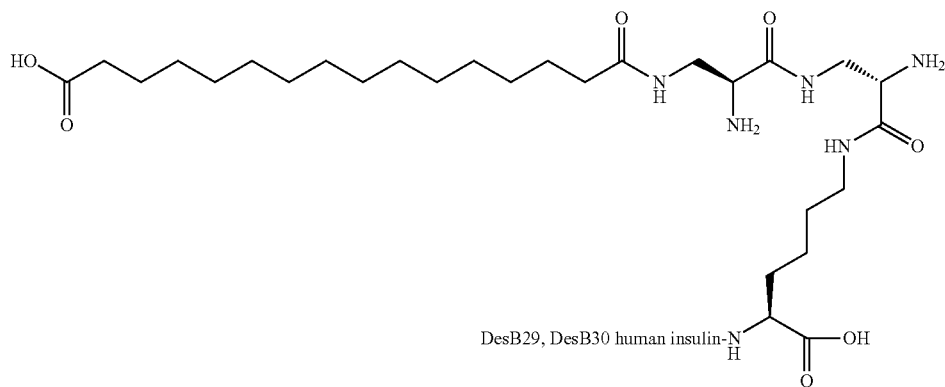

This compound can be activated with TSTU in similar fashion to the method described in Example 1, Step 6 to yield 15-{(S)-2-tert-butoxycarbonylamino-2-[(S)-2-tert-butoxycarbonylamino-2-(2,5-dioxopyrrolidin-1-yloxycarbonyl)ethylcarbamoyl]ethylcarbamoyl}pentadecanoic acid tert-butyl ester, and this compound can be coupled to insulin to yield the title compound as described in Example 1, Step 7 using prepatative HPLC to isolate the product.

Example 6

Synthesis of $N^{\epsilon B29}$-[(S)-6-Amino-2-(15-carboxybentadecanoylamino)hexanoyl]desB30 human insulin

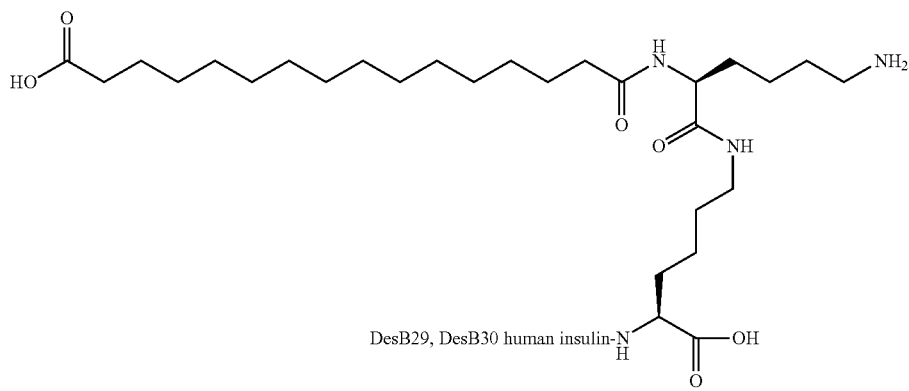

The title compound can be prepared in similar fashion as the methods used in example 4.

Example 7

Synthesis of $N^{\epsilon B29}$-3-{[2-(15-carboxy-pentadecanoylamino)-ethyl]-methyl-amino}-propionyl desB30 human insulin

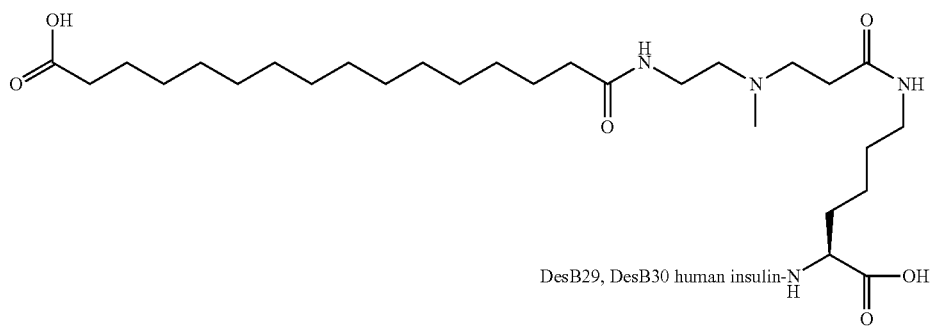

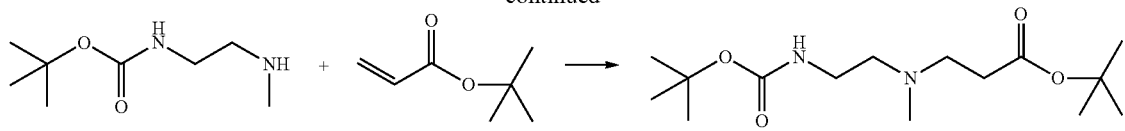

1-Boc-amino-2-methylamino-ethane (1 g, 4.75 mmol) and tert-butyl acrylate (0.61 g, 4.75 mmol) were dissolved in ethanol (10 mL) with triethylamine (1.32 mL, 9.5 mmol) and refluxed overnight. The solvent was evaporated in vacuo, and 3-(Boc-aminoethyl-methyl-amino)-propionic acid tert-butyl ester was isolated by addition of ethyl acetate (300 ml) and washing with 2×5% sodium carbonate, water and brine followed by drying over magnesium sulphate and evaporation in vacuo to leave an oil (630 mg, 44%).

LCMS: m/z: 303.5 (M+H)

¹H-NMR (CDCl3, 400 MHz) δ 5.11 (bs, 1H), 3.20 (t, 2H), 2.65 (t, 2H), 2.46 (t, 2H), 2.37 (t, 2H), 2.21 (s, 3H), 1.46 (s, 9H), 1.44 (s, 9H).

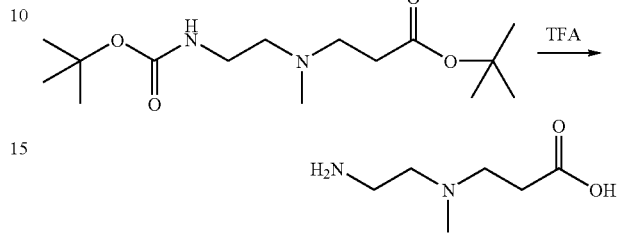

3-(Boc-aminoethyl-methyl-amino)-propionic acid tert-butyl ester (630 mg, 2.1 mmol) was treated with trifluoroacetic acid (6 mL) for 2 hours. 3-(Aminoethyl-methyl-amino)-propionic acid trifluoroacetic acid salt was isolated by recrystallisation from THF to give a white powder, 974 mg (quantitative).

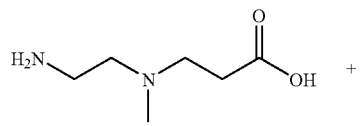

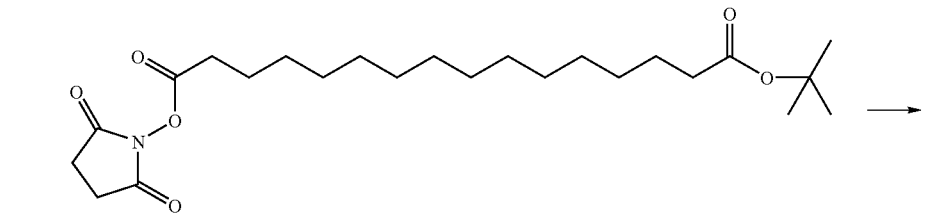

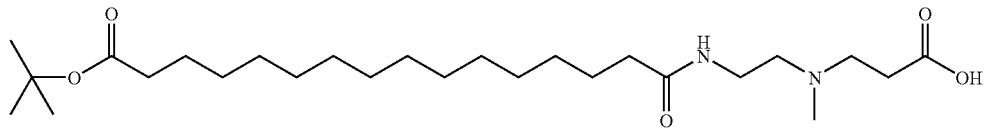

3-(aminoethyl-methyl-amino)-propionic acid (448 mg, 1.2 mmol) and tert-butyl succinimidyl hexadecandioate (474 mg, 1.1 mmol) were reacted overnight in DMF (6 mL) with triethylamine (0.53 mL, 2.0 mmol). The solvent was evaporated in vacuo, and 3-{[2-(15-tert-butyl-carboxy-pentadecanoylamino)-ethyl]-methyl-amino}-propionic acid was isolated by addition of ethyl acetate and washing with 0.1 M phosphate buffer pH 4, water and brine followed by drying over magnesium sulphate and evaporation in vacuo.

LCMS: m/z: 471.4 (M+H)

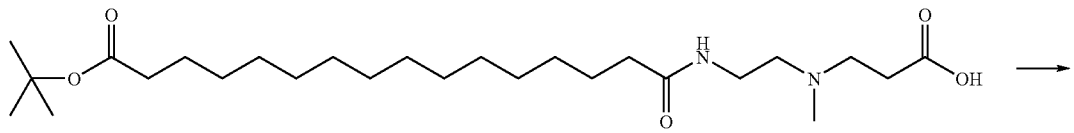

-continued

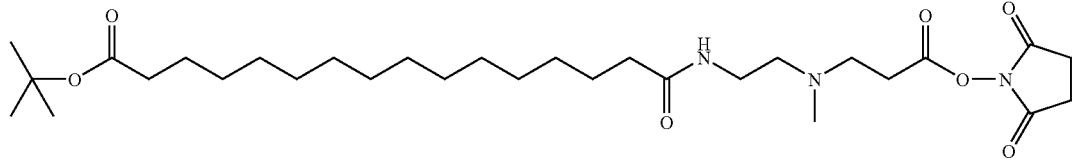

3-{[2-(15-tert-butyl-carboxy-pentadecanoylamino)-ethyl]-methyl-amino}-propionic acid (25 mg, 0.053 mmol) was dissolved in tetrahydrofuran (0.3 mL) and treated with O—(N-succinimidyl)-1,1,3,3-tetramethyluronium tetrafluoroborate (10 mg, 0.042 mmol) and triethylamine (7.3 μL, 0.053 mmol) overnight. The crude mixture was used directly in insulin acylation.
DesB30 human insulin (200 mg, 0.022 mmol) was dissolved in 100 mM sodium carbonate, pH 10.5 (1 mL) at room temperature. Crude 3-{[2-(15-tert-butyl-carboxy-pentadecanoylamino)-ethyl]-methyl-amino}-propionic acid O-succinimidyl ester from above was added to the insulin solution. After 30 mins, pH was adjusted by HCl to 5.5, and the isoelectric precipitate is collected by centrifugation and dried in vacuo.

The protected insulin intermediate was dissolved in 95% TFA (3 mL), which after 30 mins was evaporated in vacuo. $N^{\epsilon B29}$-3-{[2-(15-carboxy-pentadecanoylamino)-ethyl]-methyl-amino}-propionyl desB30 human insulin was purified by RP-HPLC on C4 column in buffer A: 10% MeCN in 0.1% TFA-water, buffer B: 80% MeCN in 0.1% TFA-water.
LCMS: 1526.6 (M/4=1526.8).

Example 8

Synthesis of $N^{\epsilon B29}$-3-{[2-(14-carboxy-tetradecanoylamino)-ethyl]-methyl-amino}-propionyl desB30 human insulin

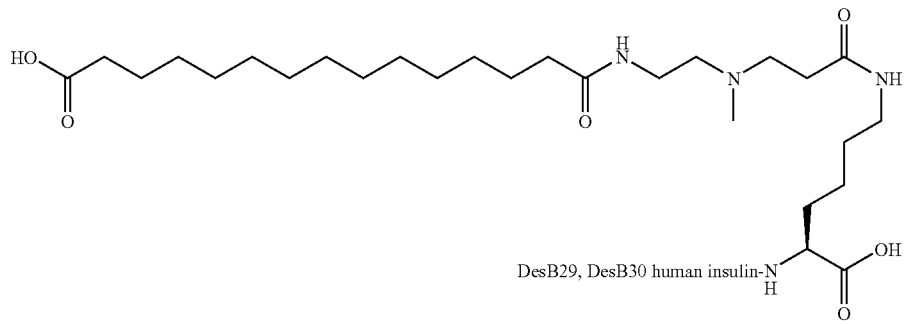

The compound is prepared as described above, from 1-Boc-amino-2-methylamino-ethane and tert-butyl acrylate and tert-butyl succinimidyl pentadecanoate.

Example 9

Synthesis of $N^{\epsilon B29}$-3-{[2-(15-carboxy-tetradecanoylamino)-propyl]-methyl-amino}-propionyl desB30 human insulin

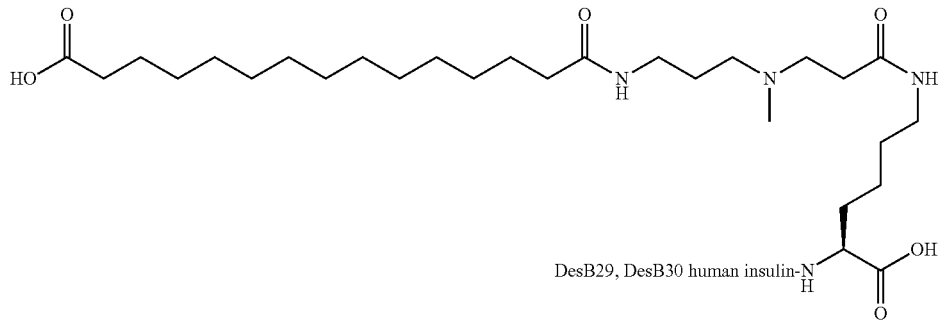

The compound is prepared as described above, from 1-Boc-amino-3-methylamino-propane and tert-butyl acrylate and tert-butyl succinimidyl pentadecanoate.

Example 10

Synthesis of $N^{\epsilon B29}$-3-{[2-(15-carboxy-pentadecanoylamino)-ethyl]-ethyl-amino}-propionyl desB30 human insulin

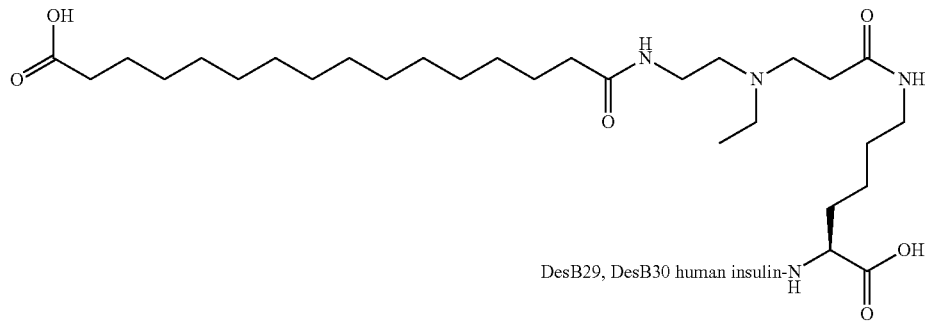

The compound is prepared as described above, from 1-Boc-amino-2-amino-ethane and tert-butyl acrylate. The intermediary 3-(Boc-aminoethyl-amino)-propionic acid tert-butyl ester is reductively alkylated using acetaldehyde and sodium borohydride in methanol, followed by reaction with protected tert-butyl succinimidyl hexadecandioate, activation as succinimidyl ester and reaction with insulin as described above.

Example 11

Synthesis of $N^{\epsilon B29}$-(15-carboxy-pentadecanoyl-γ-L-glutamyl-(2-dimethylaminoethyl-amide) desB30 human insulin Boc-L-Glu(OtBu)-OSu is reacted with 2-dimethylaminoethylamine in tetrahydrofuran and triethylamine at room temperature overnight, and worked up from ethyl acetate as described above. The product, Boc-L-Glu(OtBu)-NHCH$_2$CH$_2$NMe$_2$ is treated with trifloroacetic acid for 2 hours and dried in vacuo. The product, L-glutamyl-2-dimethylaminoethyl-amide is reacted with tert-butyl succinimidyl hexadecandioate, activated as succinimidyl ester and coupled to desB30 human insulin as described above.

Example 12

Hydrophobicity, Albumin Affinity, Self-Association and Mixability of Long Acting and Short-Acting Insulins Analysis of Selv-Associating Properties of the Insulin Derivatives of the Invention The ability of the insulin derivatives of the invention to self-associate into large, but soluble complexes is analysed using SEC (size exclusion chromatography):

Column: Superose™ 6 PC 3.2/30, CV=2.4 ml (Amerham Biosciences)

Temperature: 37° C.

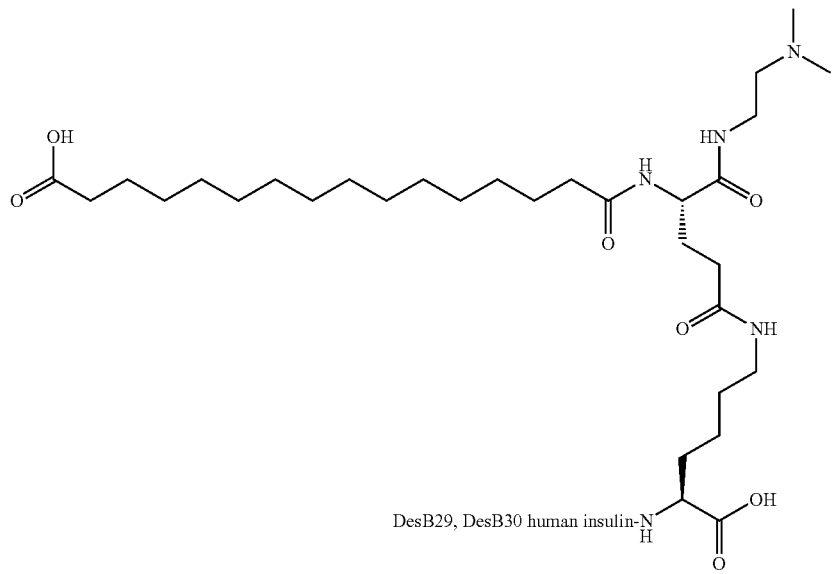

SEC buffer: 140 mM NaCl, 10 mM TrisHCl, 0.01% NaN$_3$, pH 7.5

Injection volume: 20 μl
Flow: 0.05 ml/min
Runtime: 60 min and equilibration of additional 100 min For this analysis the insulin derivatives of the invention are in a solution consisting of 0.6 mM derivative, 2.1 Zn$^{2+}$/hexamer, 16 mM phenol, 7 mM phosphate pH 7.8. The retention time of the derivative is then compared to the retention times of the following standard molecules: Blue dextran (>5 MDa, K$_{AV}$ 0.0), Thyroglobulin (669 kDa, K$_{AV}$ 0.28), Ferritin (440 kDa, K$_{AV}$ 0.39), Ovalbumin (44.5 kDa, K$_{AV}$ 0.56), Ribonuclease (13.7 kDa, K$_{AV}$ 0.69) and a second reference of Albumin (66 kDa, K$_{AV}$ 0.53), Co(III)insulin-hexamer (35 kDa, K$_{AV}$ 0.61), and monomeric insulin X2 (6 kDa, K$_{AV}$ 0.73). The following equation is used to determine the K$_{av}$ for the derivative:

$$K_{av} = (t-t_0)/(V_t/(f+t_d-t_0))$$

Where t is the retention time for a given peak, $t_0$ is the retention time for Blue dextran, $V_t$ is the total column volume (here 2.4 ml), f is the flow (here 0.04 ml/min), and $t_d$ is the retention time for Blue dextran without the column in the system.

The K$_{av}$ value indicates the degree of selv-association of a derivative, i.e. a large K$_{av}$, similar to the K$_{av}$, for the Co(III) insulin hexamer and X2 insulin monomer shows low or no propensity of the derivative to form large, selv-associated complexes, while very small K$_{av}$, close to zero or even negative shows great propensity of the derivative for selv-association into large, soluble complexes.

Hydrophobicity Data on Insulin Derivatives According to the Invention.

The hydrophobicity (hydrophobic index) of the insulin derivatives of the invention relative to human insulin, k'$_{rel}$, was measured on a LiChrosorb RP18 (5 μm, 250×4 mm) HPLC column by isocratic elution at 40° C. using mixtures of A) 0.1 M sodium phosphate buffer, pH 7.3, containing 10% acetonitrile, and B) 50% acetonitrile in water as eluents. The elution was monitored by following the UV absorption of the eluate at 214 nm. Void time, $t_0$, was found by injecting 0.1 mM sodium nitrate. Retention time for human insulin, $t_{human}$, was adjusted to at least 2$t_0$ by varying the ratio between the A and B solutions. k'$_{rel}$=($t_{derivative}$-$t_0$)/($t_{human}$-$t_0$). k'$_{rel}$ found for a number of insulin derivatives according to the invention are given in Table 1.

Human Serum Albumin Affinity Assay

Relative binding constant of 125I-TyrA14-analogue to human serum albumin immobilised on Minileak particles and measured at 23° C. (detemir=1 in saline buffer).

Mixability of Long-Acting and Short-Acting Insulins as Analyzed by Size-Exclusion Chromatography of Insulin Mixtures SEC: Mixability of Insulin Aspart (3 Zn/6 insulin, glycerol 1.6%, 16 mM phenol and 16 mM m-cresol, sodium chloride 10 mM, phosphate 7 mM, pH 7.4) and prolonged acting insulin (2.1 or 6 Zn/6 insulin) 30:70, as measured by collecting fractions from SEC (as described above) and quantifying by HPLC the presence of prolonged-acting and fast-acting insulins in the high molecular weight fraction (fraction 2, MW>HSA) and in the low molecular weight fraction (fraction 3, MW=HSA), respectively.

Four fractions are collected at size of 16 min after delay, of which fraction 2 [16-32 min] (peak 1) contain associated form larger than albumin (32 min correspond to K$_{AV}$ 0.46) and fraction 3 (peak 2) contain dihexameric, hexameric, dimeric and monomeric forms of insulin.

HPLC: Reverse phase chromatography on a Zorbax Eclipse XDB-C18 2.1*15 mm (1.8 μm) gradient eluted with buffer A: 0.2 M sodium sulphate, 0.04 M sodium phosphate, 10% acetonitrile, pH 7.2 and buffer B: 70% acetonitrile at 30° C., 19-34% B in 4.5 min. linear, sudden initial condition at 5 min., run time of 7 min., flow of 0.5 ml/min., injection volume of 14 μL and UV detection at 276 nm using Insulin Aspart reference of 609 μM for both analogues.

| Compound | Hydrophobicity relative to human insulin | Insulin receptor affinity relative to human insulin | Human serum albumin affinity relative to insulin detemir | Self-association: K$_{av}$ (% area of peak) |
|---|---|---|---|---|
| Example 1 | 18 | 17% | 14 | 0.03 (88) |
| Example 2 | 5.3 | 34% | 2.1 | 0.29 (36) |
| Example 3 | 2.4 | 28% | 2.3 | 0.15 (77) |
| Example 7 | 4.2 | 31% | — | — |

Table legend:
K$_{av}$ = 0.55 for human serum albumin,
K$_{av}$ = 0.63 for human insulin Co(III)hexamer,
K$_{av}$ = 0.72 for the monomeric insulin analogue X2.
n.a. = not analyzed.

Example 13

Euglycaemic Glucose Clamp after s.c. Administration of Insulin Preparations to Pigs Female pigs, 60-90 kg, fasted for 18 h. During the experiments the pigs are free to move in their pens. An insulin dose is administered s.c., depending of dose size often divided in two depots. Each pig is kept euglycaemic at its individual fasting glucose levels for up to 24 h by a variable rate intravenous infusion of a 20% glucose solution. The infusion is given through a catheter inserted in the jugular vein. Depending on changes in plasma glucose concentrations observed during frequent plasma glucose monitoring, the necessary adjustments of the glucose infusion are made empirically. Blood samples are collected in EDTA glass tubes every 15-30 min, plasma separated for glucose and insulin measurements. Glucose is determined within 1.5 min of blood sampling with an YSI (Yellow Springs Instruments) glucose analyser (glucose oxidase method). Mean glucose infusion rate (GIR) profiles and mean plasma insulin profiles are made for each insulin preparation. (FIGS. 2-4 show mean±SEM).

Example 14

Formulations of Insulin Derivative—600-900-1200-1800-2400-3000 nmol/mL

A. LysB29Nε-hexadecandioyl-γ-Glu desB30 human insulin 12 µmol was dissolved in water and mixed with an aqueous solution containing phenol 0.16 mmol, m-cresol 0.16 mmol and glycerol ca. 2 mmol (to make isotonicity). Zinc acetate 8 µmol was added, pH was adjusted to 7.6 and finally the volume adjusted to 10 mL by adding water.

B. LysB29Nε-hexadecandioyl-γ-Glu desB30 human insulin 12 µmol was dissolved in water and mixed with an aqueous solution containing phenol 0.16 mmol, m-cresol 0.16 mmol and glycerol ca. 2 mmol. Zinc acetate 10 µmol was added, pH was adjusted to 7.6 and finally the volume adjusted to 10 mL by adding water.

C. LysB29Nε-hexadecandioyl-γ-Glu desB30 human insulin 12 µmol was dissolved in water and mixed with an aqueous solution containing phenol 0.16 mmol, m-cresol 0.16 mmol and glycerol ca. 2 mmol. Zinc acetate 12 µmol was added, pH was adjusted to 7.6 and finally the volume adjusted to 10 mL by adding water.

D. LysB29Nε-hexadecandioyl-γ-Glu desB30 human insulin 18 µmol was dissolved in water and mixed with an aqueous solution containing phenol 0.16 mmol, m-cresol 0.16 mmol and glycerol ca. 2 mmol. Zinc acetate 12 µmol was added, pH was adjusted to 7.6 and finally the volume adjusted to 10 mL by adding water.

E. LysB29Nε-hexadecandioyl-γ-Glu desB30 human insulin 18 µmol was dissolved in water and mixed with an aqueous solution containing phenol 0.16 mmol, m-cresol 0.16 mmol and glycerol ca. 2 mmol. Zinc acetate 15 µmol was added, pH was adjusted to 7.6 and finally the volume adjusted to 10 mL by adding water.

F. LysB29Nε-hexadecandioyl-γ-Glu desB30 human insulin 18 µmol was dissolved in water and mixed with an aqueous solution containing phenol 0.16 mmol, m-cresol 0.16 mmol and glycerol ca. 2 mmol. Zinc acetate 18 µmol was added, pH was adjusted to 7.6 and finally the volume adjusted to 10 mL by adding water.

G. LysB29Nε-hexadecandioyl-γ-Glu desB30 human insulin 12 µmol was dissolved in water and mixed with an aqueous solution containing phenol 0.16 mmol, m-cresol 0.16 mmol, trishydroxymethylaminomethan 70 µmol and glycerol ca. 2 mmol. Zinc acetate 8 µmol was added, pH was adjusted to 7.6 and finally the volume adjusted to 10 mL by adding water.

H. LysB29Nε-hexadecandioyl-γ-Glu desB30 human insulin 12 µmol was dissolved in water and mixed with an aqueous solution containing phenol 0.16 mmol, m-cresol 0.16 mmol, trishydroxymethylaminomethan 70 µmol and glycerol ca. 2 mmol. Zinc acetate 10 µmol was added, pH was adjusted to 7.6 and finally the volume adjusted to 10 mL by adding water.

I. LysB29Nε-hexadecandioyl-γ-Glu desB30 human insulin 12 µmol was dissolved in water and mixed with an aqueous solution containing phenol 0.16 mmol, m-cresol 0.16 mmol, trishydroxymethylaminomethan 70 µmol and glycerol ca. 2 mmol. Zinc acetate 12 µmol was added, pH was adjusted to 7.6 and finally the volume adjusted to 10 mL by adding water.

J. LysB29Nε-hexadecandioyl-γ-Glu desB30 human insulin 18 µmol was dissolved in water and mixed with an aqueous solution containing phenol 0.16 mmol, m-cresol 0.16 mmol, trishydroxymethylaminomethan 70 µmol and glycerol ca. 2 mmol. Zinc acetate 12 µmol was added, pH was adjusted to 7.6 and finally the volume adjusted to 10 mL by adding water.

K. LysB29Nε-hexadecandioyl-γ-Glu desB30 human insulin 18 µmol was dissolved in water and mixed with an aqueous solution containing phenol 0.16 mmol, m-cresol 0.16 mmol, trishydroxymethylaminomethan 70 µmol and glycerol ca. 2 mmol. Zinc acetate 15 µmol was added, pH was adjusted to 7.6 and finally the volume adjusted to 10 mL by adding water.

L. LysB29Nε-hexadecandioyl-γ-Glu desB30 human insulin 18 µmol was dissolved in water and mixed with an aqueous solution containing phenol 0.16 mmol, m-cresol 0.16 mmol, trishydroxymethylaminomethan 70 µmol and glycerol ca. 2 mmol. Zinc acetate 18 µmol was added, pH was adjusted to 7.6 and finally the volume adjusted to 10 mL by adding water.

M. LysB29Nε-hexadecandioyl-γ-Glu desB30 human insulin 12 µmol was dissolved in water and mixed with an aqueous solution containing phenol 0.19 mmol, m-cresol 0.19 mmol and glycerol ca. 2 mmol. Zinc acetate 8 µmol was added, pH was adjusted to 7.6 and finally the volume adjusted to 10 mL by adding water.

N. LysB29Nε-hexadecandioyl-γ-Glu desB30 human insulin 12 µmol was dissolved in water and mixed with an aqueous solution containing phenol 0.19 mmol, m-cresol 0.19 mmol and glycerol ca. 2 mmol. Zinc acetate 10 µmol was added, pH was adjusted to 7.6 and finally the volume adjusted to 10 mL by adding water.

O. LysB29Nε-hexadecandioyl-γ-Glu desB30 human insulin 12 µmol was dissolved in water and mixed with an aqueous solution containing phenol 0.19 mmol, m-cresol 0.19 mmol and glycerol ca. 2 mmol. Zinc acetate 12 µmol was added, pH was adjusted to 7.6 and finally the volume adjusted to 10 mL by adding water.

P. LysB29Nε-hexadecandioyl-γ-Glu desB30 human insulin 18 µmol was dissolved in water and mixed with an aqueous solution containing phenol 0.19 mmol, m-cresol 0.19 mmol and glycerol ca. 2 mmol. Zinc acetate 12 µmol was added, pH was adjusted to 7.6 and finally the volume adjusted to 10 mL by adding water.

Q. LysB29Nε-hexadecandioyl-γ-Glu desB30 human insulin 18 µmol was dissolved in water and mixed with an aqueous solution containing phenol 0.19 mmol, m-cresol 0.19 mmol and glycerol ca. 2 mmol. Zinc acetate 15 µmol was added, pH was adjusted to 7.6 and finally the volume adjusted to 10 mL by adding water.

R. LysB29Nε-hexadecandioyl-γ-Glu desB30 human insulin 18 µmol was dissolved in water and mixed with an aqueous solution containing phenol 0.19 mmol, m-cresol 0.19 mmol and glycerol ca. 2 mmol. Zinc acetate 18 µmol was added, pH was adjusted to 7.6 and finally the volume adjusted to 10 mL by adding water.

S. LysB29Nε-hexadecandioyl-γ-Glu desB30 human insulin 12 µmol was dissolved in water and mixed with an aqueous solution containing phenol 0.19 mmol, m-cresol 0.19 mmol, trishydroxymethylaminomethan 70 µmol and glycerol ca. 2 mmol. Zinc acetate 8 µmol was added, pH was adjusted to 7.6 and finally the volume adjusted to 10 mL by adding water.

T. LysB29Nε-hexadecandioyl-γ-Glu desB30 human insulin 12 µmol was dissolved in water and mixed with an aqueous solution containing phenol 0.19 mmol, m-cresol 0.19 mmol, trishydroxymethylaminomethan 70 µmol and glycerol ca. 2 mmol. Zinc acetate 10 µmol was added, pH was adjusted to 7.6 and finally the volume adjusted to 10 mL by adding water.

U. LysB29Nε-hexadecandioyl-γ-Glu desB30 human insulin 12 µmol was dissolved in water and mixed with an aqueous solution containing phenol 0.19 mmol, m-cresol 0.19 mmol, trishydroxymethylaminomethan 70 µmol and glycerol ca. 2 mmol. Zinc acetate 12 µmol was added, pH was adjusted to 7.6 and finally the volume adjusted to 10 mL by adding water.

V. LysB29Nε-hexadecandioyl-γ-Glu desB30 human insulin 18 μmol was dissolved in water and mixed with an aqueous solution containing phenol 0.19 mmol, m-cresol 0.19 mmol, trishydroxymethylaminomethan 70 μmol and glycerol ca. 2 mmol. Zinc acetate 12 μmol was added, pH was adjusted to 7.6 and finally the volume adjusted to 10 mL by adding water.

X. LysB29Nε-hexadecandioyl-γ-Glu desB30 human insulin 18 μmol was dissolved in water and mixed with an aqueous solution containing phenol 0.19 mmol, m-cresol 0.19 mmol, trishydroxymethylaminomethan 70 μmol and glycerol ca. 2 mmol. Zinc acetate 15 μmol was added, pH was adjusted to 7.6 and finally the volume adjusted to 10 mL by adding water.

Y. LysB29Nε-hexadecandioyl-γ-Glu desB30 human insulin 18 μmol was dissolved in water and mixed with an aqueous solution containing phenol 0.19 mmol, m-cresol 0.19 mmol, trishydroxymethylaminomethan 70 μmol and glycerol ca. 2 mmol. Zinc acetate 18 μmol was added, pH was adjusted to 7.6 and finally the volume adjusted to 10 mL by adding water.

AA. LysB29Nε-hexadecandioyl-γ-Glu desB30 human insulin 6 μmol was dissolved in water and mixed with an aqueous solution containing phenol 0.16 mmol, m-cresol 0.16 mmol and glycerol ca. 2 mmol (to make isotonicity). Zinc acetate 4 μmol was added, pH was adjusted to 7.6 and finally the volume adjusted to 10 mL by adding water.

AB. LysB29Nε-hexadecandioyl-γ-Glu desB30 human insulin 6 μmol was dissolved in water and mixed with an aqueous solution containing phenol 0.16 mmol, m-cresol 0.16 mmol and glycerol ca. 2 mmol. Zinc acetate 5 μmol was added, pH was adjusted to 7.6 and finally the volume adjusted to 10 mL by adding water.

AC. LysB29Nε-hexadecandioyl-γ-Glu desB30 human insulin 6 μmol was dissolved in water and mixed with an aqueous solution containing phenol 0.16 mmol, m-cresol 0.16 mmol and glycerol ca. 2 mmol. Zinc acetate 6 μmol was added, pH was adjusted to 7.6 and finally the volume adjusted to 10 mL by adding water.

AD. LysB29Nε-hexadecandioyl-γ-Glu desB30 human insulin 9 μmol was dissolved in water and mixed with an aqueous solution containing phenol 0.16 mmol, m-cresol 0.16 mmol and glycerol ca. 2 mmol. Zinc acetate 6 μmol was added, pH was adjusted to 7.6 and finally the volume adjusted to 10 mL by adding water.

AE. LysB29Nε-hexadecandioyl-γ-Glu desB30 human insulin 9 μmol was dissolved in water and mixed with an aqueous solution containing phenol 0.16 mmol, m-cresol 0.16 mmol and glycerol ca. 2 mmol. Zinc acetate 7.5 μmol was added, pH was adjusted to 7.6 and finally the volume adjusted to 10 mL by adding water.

AF. LysB29Nε-hexadecandioyl-γ-Glu desB30 human insulin 9 μmol was dissolved in water and mixed with an aqueous solution containing phenol 0.16 mmol, m-cresol 0.16 mmol and glycerol ca. 2 mmol. Zinc acetate 9 μmol was added, pH was adjusted to 7.6 and finally the volume adjusted to 10 mL by adding water.

AG. LysB29Nε-hexadecandioyl-γ-Glu desB30 human insulin 6 μmol was dissolved in water and mixed with an aqueous solution containing phenol 0.16 mmol, m-cresol 0.16 mmol, trishydroxymethylaminomethan 70 μmol and glycerol ca. 2 mmol. Zinc acetate 4 μmol was added, pH was adjusted to 7.6 and finally the volume adjusted to 10 mL by adding water.

AH. LysB29Nε-hexadecandioyl-γ-Glu desB30 human insulin 6 μmol was dissolved in water and mixed with an aqueous solution containing phenol 0.16 mmol, m-cresol 0.16 mmol, trishydroxymethylaminomethan 70 μmol and glycerol ca. 2 mmol. Zinc acetate 5 μmol was added, pH was adjusted to 7.6 and finally the volume adjusted to 10 mL by adding water.

AI. LysB29Nε-hexadecandioyl-γ-Glu desB30 human insulin 6 μmol was dissolved in water and mixed with an aqueous solution containing phenol 0.16 mmol, m-cresol 0.16 mmol, trishydroxymethylaminomethan 70 μmol and glycerol ca. 2 mmol. Zinc acetate 6 μmol was added, pH was adjusted to 7.6 and finally the volume adjusted to 10 mL by adding water.

AJ. LysB29Nε-hexadecandioyl-γ-Glu desB30 human insulin 9 μmol was dissolved in water and mixed with an aqueous solution containing phenol 0.16 mmol, m-cresol 0.16 mmol, trishydroxymethylaminomethan 70 μmol and glycerol ca. 2 mmol. Zinc acetate 6 μmol was added, pH was adjusted to 7.6 and finally the volume adjusted to 10 mL by adding water.

AK. LysB29Nε-hexadecandioyl-γ-Glu desB30 human insulin 9 μmol was dissolved in water and mixed with an aqueous solution containing phenol 0.16 mmol, m-cresol 0.16 mmol, trishydroxymethylaminomethan 70 μmol and glycerol ca. 2 mmol. Zinc acetate 7.5 μmol was added, pH was adjusted to 7.6 and finally the volume adjusted to 10 mL by adding water.

AL. LysB29Nε-hexadecandioyl-γ-Glu desB30 human insulin 9 μmol was dissolved in water and mixed with an aqueous solution containing phenol 0.16 mmol, m-cresol 0.16 mmol, trishydroxymethylaminomethan 70 μmol and glycerol ca. 2 mmol. Zinc acetate 9 μmol was added, pH was adjusted to 7.6 and finally the volume adjusted to 10 mL by adding water.

AM. LysB29Nε-hexadecandioyl-γ-Glu desB30 human insulin 24 μmol was dissolved in water and mixed with an aqueous solution containing phenol 0.19 mmol, m-cresol 0.19 mmol and glycerol ca. 2 mmol. Zinc acetate 16 μmol was added, pH was adjusted to 7.6 and finally the volume adjusted to 10 mL by adding water.

AN. LysB29Nε-hexadecandioyl-γ-Glu desB30 human insulin 24 μmol was dissolved in water and mixed with an aqueous solution containing phenol 0.19 mmol, m-cresol 0.19 mmol and glycerol ca. 2 mmol. Zinc acetate 20 μmol was added, pH was adjusted to 7.6 and finally the volume adjusted to 10 mL by adding water.

AO. LysB29Nε-hexadecandioyl-γ-Glu desB30 human insulin 24 μmol was dissolved in water and mixed with an aqueous solution containing phenol 0.19 mmol, m-cresol 0.19 mmol and glycerol ca. 2 mmol. Zinc acetate 24 μmol was added, pH was adjusted to 7.6 and finally the volume adjusted to 10 mL by adding water.

AP. LysB29Nε-hexadecandioyl-γ-Glu desB30 human insulin 24 μmol was dissolved in water and mixed with an aqueous solution containing phenol 0.19 mmol, m-cresol 0.19 mmol, trishydroxymethylaminomethan 70 μmol and glycerol ca. 2 mmol. Zinc acetate 16 μmol was added, pH was adjusted to 7.6 and finally the volume adjusted to 10 mL by adding water.

AQ. LysB29Nε-hexadecandioyl-γ-Glu desB30 human insulin 24 μmol was dissolved in water and mixed with an aqueous solution containing phenol 0.19 mmol, m-cresol 0.19 mmol, trishydroxymethylaminomethan 70 μmol and glycerol ca. 2 mmol. Zinc acetate 20 μmol was added, pH was adjusted to 7.6 and finally the volume adjusted to 10 mL by adding water.

AR. LysB29Nε-hexadecandioyl-γ-Glu desB30 human insulin 24 μmol was dissolved in water and mixed with an aqueous solution containing phenol 0.19 mmol, m-cresol 0.19 mmol, trishydroxymethylaminomethan 70 μmol and glycerol ca. 2 mmol. Zinc acetate 24 µmol was added, pH was adjusted to 7.6 and finally the volume adjusted to 10 mL by adding water.

AS. LysB29Nε-hexadecandioyl-γ-Glu desB30 human insulin 30 µmol was dissolved in water and mixed with an aqueous solution containing phenol 0.19 mmol, m-cresol 0.19 mmol and glycerol ca. 2 mmol. Zinc acetate 20 µmol was added, pH was adjusted to 7.6 and finally the volume adjusted to 10 mL by adding water.

AT. LysB29Nε-hexadecandioyl-γ-Glu desB30 human insulin 30 µmol was dissolved in water and mixed with an aqueous solution containing phenol 0.19 mmol, m-cresol 0.19 mmol and glycerol ca. 2 mmol. Zinc acetate 25 µmol was added, pH was adjusted to 7.6 and finally the volume adjusted to 10 mL by adding water.

AU. LysB29Nε-hexadecandioyl-γ-Glu desB30 human insulin 30 µmol was dissolved in water and mixed with an aqueous solution containing phenol 0.19 mmol, m-cresol 0.19 mmol and glycerol ca. 2 mmol. Zinc acetate 30 µmol was added, pH was adjusted to 7.6 and finally the volume adjusted to 10 mL by adding water.

AV. LysB29Nε-hexadecandioyl-γ-Glu desB30 human insulin 30 µmol was dissolved in water and mixed with an aqueous solution containing phenol 0.19 mmol, m-cresol 0.19 mmol, trishydroxymethylaminomethan 70 µmol and glycerol ca. 2 mmol. Zinc acetate 20 µmol was added, pH was adjusted to 7.6 and finally the volume adjusted to 10 mL by adding water.

AX. LysB29Nε-hexadecandioyl-γ-Glu desB30 human insulin 30 µmol was dissolved in water and mixed with an aqueous solution containing phenol 0.19 mmol, m-cresol 0.19 mmol, trishydroxymethylaminomethan 70 µmol and glycerol ca. 2 mmol. Zinc acetate 25 µmol was added, pH was adjusted to 7.6 and finally the volume adjusted to 10 mL by adding water.

AY. LysB29Nε-hexadecandioyl-γ-Glu desB30 human insulin 30 µmol was dissolved in water and mixed with an aqueous solution containing phenol 0.19 mmol, m-cresol 0.19 mmol, trishydroxymethylaminomethan 70 µmol and glycerol ca. 2 mmol. Zinc acetate 30 µmol was added, pH was adjusted to 7.6 and finally the volume adjusted to 10 mL by adding water.

Example 15

Formulations of Insulin Derivative—1200-1800-2400 nmol/ml and Insulin Aspart—1200-1800-2400 nmol/ml.

A: Insulin Aspart 12 µmol was suspended in water and mixed with a solution containing 6 µmol Zinc acetate and hydrochloric acid to obtain a solution. A solution containing phenol 0.16 mmol, m-cresol 0.16 mmol, sodium chloride 0.10 mmol, and glycerol ca. 2 mmol was then added. Finally pH was adjusted to 7.4 with sodium hydroxide and the volume was adjusted to 8 mL by adding water.

B: Insulin Aspart 18 µmol was suspended in water and mixed with a solution containing 9 µmol Zinc acetate and hydrochloric acid to obtain a solution. A solution containing phenol 0.16 mmol, m-cresol 0.16 mmol, sodium chloride 0.10 mmol, and glycerol ca. 2 mmol was then added. Finally pH was adjusted to 7.4 with sodium hydroxide and the volume was adjusted to 8 mL by adding water.

C: Insulin Aspart 24 µmol was suspended in water and mixed with a solution containing 12 µmol Zinc acetate and hydrochloric acid to obtain a solution. A solution containing phenol 0.16 mmol, m-cresol 0.16 mmol, sodium chloride 0.10 mmol, and glycerol ca. 2 mmol was then added. Finally pH was adjusted to 7.4 with sodium hydroxide and the volume was adjusted to 8 mL by adding water.

D: Insulin Aspart 12 µmol was suspended in water and mixed with a solution containing 6 µmol Zinc acetate and hydrochloric acid to obtain a solution. A solution containing phenol 0.19 mmol, m-cresol 0.19 mmol, sodium chloride 0.10 mmol, and glycerol ca. 2 mmol was then added. Finally pH was adjusted to 7.4 with sodium hydroxide and the volume was adjusted to 8 mL by adding water.

E: Insulin Aspart 18 µmol was suspended in water and mixed with a solution containing 9 µmol Zinc acetate and hydrochloric acid to obtain a solution. A solution containing phenol 0.19 mmol, m-cresol 0.19 mmol, sodium chloride 0.10 mmol, and glycerol ca. 2 mmol was then added. Finally pH was adjusted to 7.4 with sodium hydroxide and the volume was adjusted to 8 mL by adding water.

F: Insulin Aspart 24 µmol was suspended in water and mixed with a solution containing 12 µmol Zinc acetate and hydrochloric acid to obtain a solution. A solution containing phenol 0.19 mmol, m-cresol 0.19 mmol, sodium chloride 0.10 mmol, and glycerol ca. 2 mmol was then added. Finally pH was adjusted to 7.4 with sodium hydroxide and the volume was adjusted to 8 mL by adding water.

G: Insulin Aspart 12 µmol was suspended in water and mixed with a solution containing 6 µmol Zinc acetate and hydrochloric acid to obtain a solution. A solution containing phenol 0.16 mmol, m-cresol 0.16 mmol, sodium chloride 0.10 mmol, trishydroxymethylaminomethane 70 µmol and glycerol ca. 2 mmol was then added. Finally pH was adjusted to 7.4 with sodium hydroxide and the volume was adjusted to 8 mL by adding water.

H: Insulin Aspart 18 µmol was suspended in water and mixed with a solution containing 9 µmol Zinc acetate and hydrochloric acid to obtain a solution. A solution containing phenol 0.16 mmol, m-cresol 0.16 mmol, sodium chloride 0.10 mmol, trishydroxymethylaminomethane 70 µmol and glycerol ca. 2 mmol was then added. Finally pH was adjusted to 7.4 with sodium hydroxide and the volume was adjusted to 8 mL by adding water.

I: Insulin Aspart 24 µmol was suspended in water and mixed with a solution containing 12 µmol Zinc acetate and hydrochloric acid to obtain a solution. A solution containing phenol 0.16 mmol, m-cresol 0.16 mmol, sodium chloride 0.10 mmol, trishydroxymethylaminomethane 70 µmol and glycerol ca. 2 mmol was then added. Finally pH was adjusted to 7.4 with sodium hydroxide and the volume was adjusted to 8 mL by adding water.

J: Insulin Aspart 12 µmol was suspended in water and mixed with a solution containing 6 µmol Zinc acetate and hydrochloric acid to obtain a solution. A solution containing phenol 0.19 mmol, m-cresol 0.19 mmol, sodium chloride 0.10 mmol, trishydroxymethylaminomethane 70 µmol and glycerol ca. 2 mmol was then added. Finally pH was adjusted to 7.4 with sodium hydroxide and the volume was adjusted to 8 mL by adding water.

K: Insulin Aspart 18 µmol was suspended in water and mixed with a solution containing 9 µmol Zinc acetate and hydrochloric acid to obtain a solution. A solution containing phenol 0.19 mmol, m-cresol 0.19 mmol, sodium chloride 0.10 mmol, trishydroxymethylaminomethane 70 µmol and glycerol ca. 2 mmol was then added. Finally pH was adjusted to 7.4 with sodium hydroxide and the volume was adjusted to 8 mL by adding water.

L: Insulin Aspart 24 µmol was suspended in water and mixed with a solution containing 12 µmol Zinc acetate and hydrochloric acid to obtain a solution. A solution containing phenol 0.19 mmol, m-cresol 0.19 mmol, sodium chloride 0.10 mmol, trishydroxymethylaminomethane 70 µmol and glycerol ca. 2 mmol was then added. Finally pH was adjusted to 7.4 with sodium hydroxide and the volume was adjusted to 8 mL by adding water.

M: LysB29Nε-hexadecandioyl-γ-Glu desB30 human insulin 12 µmol was dissolved in water and mixed with an aqueous solution containing phenol 0.16 mmol, m-cresol 0.16 mmol, sodium chloride 0.10 mmol and glycerol ca. 2 mmol (to make isotonicity). Zinc acetate 6 µmol was added, pH was adjusted to 7.4 and finally the volume adjusted to 8 mL by adding water.

N: LysB29Nε-hexadecandioyl-γ-Glu desB30 human insulin 12 µmol was dissolved in water and mixed with an aqueous solution containing phenol 0.16 mmol, m-cresol 0.16 mmol, sodium chloride 0.10 mmol and glycerol ca. 2 mmol (to make isotonicity). Zinc acetate 8 µmol was added, pH was adjusted to 7.4 and finally the volume adjusted to 8 mL by adding water.

O: LysB29Nε-hexadecandioyl-γ-Glu desB30 human insulin 12 µmol was dissolved in water and mixed with an aqueous solution containing phenol 0.16 mmol, m-cresol 0.16 mmol, sodium chloride 0.10 mmol and glycerol ca. 2 mmol (to make isotonicity). Zinc acetate 12 µmol was added, pH was adjusted to 7.4 and finally the volume adjusted to 8 mL by adding water.

P: LysB29Nε-hexadecandioyl-γ-Glu desB30 human insulin 12 µmol was dissolved in water and mixed with an aqueous solution containing phenol 0.16 mmol, m-cresol 0.16 mmol, sodium chloride 0.10 mmol and glycerol ca. 2 mmol (to make isotonicity). Zinc acetate 16 µmol was added, pH was adjusted to 7.4 and finally the volume adjusted to 8 mL by adding water.

Q: LysB29Nε-hexadecandioyl-γ-Glu desB30 human insulin 18 µmol was dissolved in water and mixed with an aqueous solution containing phenol 0.16 mmol, m-cresol 0.16 mmol, sodium chloride 0.10 mmol and glycerol ca. 2 mmol (to make isotonicity). Zinc acetate 9 µmol was added, pH was adjusted to 7.4 and finally the volume adjusted to 8 mL by adding water.

R: LysB29Nε-hexadecandioyl-γ-Glu desB30 human insulin 18 µmol was dissolved in water and mixed with an aqueous solution containing phenol 0.16 mmol, m-cresol 0.16 mmol, sodium chloride 0.10 mmol and glycerol ca. 2 mmol (to make isotonicity). Zinc acetate 12 µmol was added, pH was adjusted to 7.4 and finally the volume adjusted to 8 mL by adding water.

S: LysB29Nε-hexadecandioyl-γ-Glu desB30 human insulin 18 µmol was dissolved in water and mixed with an aqueous solution containing phenol 0.16 mmol, m-cresol 0.16 mmol, sodium chloride 0.10 mmol and glycerol ca. 2 mmol (to make isotonicity). Zinc acetate 18 µmol was added, pH was adjusted to 7.4 and finally the volume adjusted to 8 mL by adding water.

T: LysB29Nε-hexadecandioyl-γ-Glu desB30 human insulin 18 µmol was dissolved in water and mixed with an aqueous solution containing phenol 0.16 mmol, m-cresol 0.16 mmol, sodium chloride 0.10 mmol and glycerol ca. 2 mmol (to make isotonicity). Zinc acetate 24 µmol was added, pH was adjusted to 7.4 and finally the volume adjusted to 8 mL by adding water.

U: LysB29Nε-hexadecandioyl-γ-Glu desB30 human insulin 24 µmol was dissolved in water and mixed with an aqueous solution containing phenol 0.16 mmol, m-cresol 0.16 mmol, sodium chloride 0.10 mmol and glycerol ca. 2 mmol (to make isotonicity). Zinc acetate 12 µmol was added, pH was adjusted to 7.4 and finally the volume adjusted to 8 mL by adding water.

V: LysB29Nε-hexadecandioyl-γ-Glu desB30 human insulin 24 µmol was dissolved in water and mixed with an aqueous solution containing phenol 0.16 mmol, m-cresol 0.16 mmol, sodium chloride 0.10 mmol and glycerol ca. 2 mmol (to make isotonicity). Zinc acetate 16 µmol was added, pH was adjusted to 7.4 and finally the volume adjusted to 8 mL by adding water.

X: LysB29Nε-hexadecandioyl-γ-Glu desB30 human insulin 24 µmol was dissolved in water and mixed with an aqueous solution containing phenol 0.16 mmol, m-cresol 0.16 mmol, sodium chloride 0.10 mmol and glycerol ca. 2 mmol (to make isotonicity). Zinc acetate 24 µmol was added, pH was adjusted to 7.4 and finally the volume adjusted to 8 mL by adding water.

Y: LysB29Nε-hexadecandioyl-γ-Glu desB30 human insulin 24 µmol was dissolved in water and mixed with an aqueous solution containing phenol 0.16 mmol, m-cresol 0.16 mmol, sodium chloride 0.10 mmol and glycerol ca. 2 mmol (to make isotonicity). Zinc acetate 32 µmol was added, pH was adjusted to 7.4 and finally the volume adjusted to 8 mL by adding water.

Z: LysB29Nε-hexadecandioyl-γ-Glu desB30 human insulin 12 µmol was dissolved in water and mixed with an aqueous solution containing phenol 0.19 mmol, m-cresol 0.19 mmol, sodium chloride 0.10 mmol and glycerol ca. 2 mmol (to make isotonicity). Zinc acetate 6 µmol was added, pH was adjusted to 7.4 and finally the volume adjusted to 8 mL by adding water.

AA: LysB29Nε-hexadecandioyl-γ-Glu desB30 human insulin 12 µmol was dissolved in water and mixed with an aqueous solution containing phenol 0.19 mmol, m-cresol 0.19 mmol, sodium chloride 0.10 mmol and glycerol ca. 2 mmol (to make isotonicity). Zinc acetate 8 µmol was added, pH was adjusted to 7.4 and finally the volume adjusted to 8 mL by adding water.

AB: LysB29Nε-hexadecandioyl-γ-Glu desB30 human insulin 12 µmol was dissolved in water and mixed with an aqueous solution containing phenol 0.19 mmol, m-cresol 0.19 mmol, sodium chloride 0.10 mmol and glycerol ca. 2 mmol (to make isotonicity). Zinc acetate 12 µmol was added, pH was adjusted to 7.4 and finally the volume adjusted to 8 mL by adding water.

AC: LysB29Nε-hexadecandioyl-γ-Glu desB30 human insulin 12 µmol was dissolved in water and mixed with an aqueous solution containing phenol 0.19 mmol, m-cresol 0.19 mmol, sodium chloride 0.10 mmol and glycerol ca. 2 mmol (to make isotonicity). Zinc acetate 16 µmol was added, pH was adjusted to 7.4 and finally the volume adjusted to 8 mL by adding water.

AD: LysB29Nε-hexadecandioyl-γ-Glu desB30 human insulin 18 µmol was dissolved in water and mixed with an aqueous solution containing phenol 0.19 mmol, m-cresol 0.19 mmol, sodium chloride 0.10 mmol and glycerol ca. 2 mmol (to make isotonicity). Zinc acetate 9 µmol was added, pH was adjusted to 7.4 and finally the volume adjusted to 8 mL by adding water.

AE: LysB29Nε-hexadecandioyl-γ-Glu desB30 human insulin 18 µmol was dissolved in water and mixed with an aqueous solution containing phenol 0.19 mmol, m-cresol 0.19 mmol, sodium chloride 0.10 mmol and glycerol ca. 2 mmol (to make isotonicity). Zinc acetate 12 µmol was added, pH was adjusted to 7.4 and finally the volume adjusted to 8 mL by adding water.

AF: LysB29Nε-hexadecandioyl-γ-Glu desB30 human insulin 18 µmol was dissolved in water and mixed with an aqueous solution containing phenol 0.19 mmol, m-cresol 0.19 mmol, sodium chloride 0.10 mmol and glycerol ca. 2

AG: LysB29Nε-hexadecandioyl-γ-Glu desB30 human insulin 18 μmol was dissolved in water and mixed with an aqueous solution containing phenol 0.19 mmol, m-cresol 0.19 mmol, sodium chloride 0.10 mmol and glycerol ca. 2 mmol (to make isotonicity). Zinc acetate 24 μmol was added, pH was adjusted to 7.4 and finally the volume adjusted to 8 mL by adding water.

AH: LysB29Nε-hexadecandioyl-γ-Glu desB30 human insulin 24 μmol was dissolved in water and mixed with an aqueous solution containing phenol 0.19 mmol, m-cresol 0.19 mmol, sodium chloride 0.10 mmol and glycerol ca. 2 mmol (to make isotonicity). Zinc acetate 12 μmol was added, pH was adjusted to 7.4 and finally the volume adjusted to 8 mL by adding water.

AI: LysB29Nε-hexadecandioyl-γ-Glu desB30 human insulin 24 μmol was dissolved in water and mixed with an aqueous solution containing phenol 0.19 mmol, m-cresol 0.19 mmol, sodium chloride 0.10 mmol and glycerol ca. 2 mmol (to make isotonicity). Zinc acetate 16 μmol was added, pH was adjusted to 7.4 and finally the volume adjusted to 8 mL by adding water.

AJ: LysB29Nε-hexadecandioyl-γ-Glu desB30 human insulin 24 μmol was dissolved in water and mixed with an aqueous solution containing phenol 0.19 mmol, m-cresol 0.19 mmol, sodium chloride 0.10 mmol and glycerol ca. 2 mmol (to make isotonicity). Zinc acetate 24 μmol was added, pH was adjusted to 7.4 and finally the volume adjusted to 8 mL by adding water.

AK: LysB29Nε-hexadecandioyl-γ-Glu desB30 human insulin 24 μmol was dissolved in water and mixed with an aqueous solution containing phenol 0.19 mmol, m-cresol 0.19 mmol, sodium chloride 0.10 mmol and glycerol ca. 2 mmol (to make isotonicity). Zinc acetate 32 μmol was added, pH was adjusted to 7.4 and finally the volume adjusted to 8 mL by adding water.

AL: LysB29Nε-hexadecandioyl-γ-Glu desB30 human insulin 12 μmol was dissolved in water and mixed with an aqueous solution containing phenol 0.16 mmol, m-cresol 0.16 mmol, sodium chloride 0.10 mmol, trishydroxymethylaminomethane 70 μmol and glycerol ca. 2 mmol (to make isotonicity). Zinc acetate 6 μmol was added, pH was adjusted to 7.4 and finally the volume adjusted to 8 mL by adding water.

AM: LysB29Nε-hexadecandioyl-γ-Glu desB30 human insulin 12 μmol was dissolved in water and mixed with an aqueous solution containing phenol 0.16 mmol, m-cresol 0.16 mmol, sodium chloride 0.10 mmol, trishydroxymethylaminomethane 70 μmol and glycerol ca. 2 mmol (to make isotonicity). Zinc acetate 8 μmol was added, pH was adjusted to 7.4 and finally the volume adjusted to 8 mL by adding water.

AN: LysB29Nε-hexadecandioyl-γ-Glu desB30 human insulin 12 μmol was dissolved in water and mixed with an aqueous solution containing phenol 0.16 mmol, m-cresol 0.16 mmol, sodium chloride 0.10 mmol, trishydroxymethylaminomethane 70 μmol and glycerol ca. 2 mmol (to make isotonicity). Zinc acetate 12 μmol was added, pH was adjusted to 7.4 and finally the volume adjusted to 8 mL by adding water.

AO: LysB29Nε-hexadecandioyl-γ-Glu desB30 human insulin 12 μmol was dissolved in water and mixed with an aqueous solution containing phenol 0.16 mmol, m-cresol 0.16 mmol, sodium chloride 0.10 mmol, trishydroxymethylaminomethane 70 μmol and glycerol ca. 2 mmol (to make isotonicity). Zinc acetate 16 μmol was added, pH was adjusted to 7.4 and finally the volume adjusted to 8 mL by adding water.

AP: LysB29Nε-hexadecandioyl-γ-Glu desB30 human insulin 18 μmol was dissolved in water and mixed with an aqueous solution containing phenol 0.16 mmol, m-cresol 0.16 mmol, sodium chloride 0.10 mmol, trishydroxymethylaminomethane 70 μmol and glycerol ca. 2 mmol (to make isotonicity). Zinc acetate 9 μmol was added, pH was adjusted to 7.4 and finally the volume adjusted to 8 mL by adding water.

AQ: LysB29Nε-hexadecandioyl-γ-Glu desB30 human insulin 18 μmol was dissolved in water and mixed with an aqueous solution containing phenol 0.16 mmol, m-cresol 0.16 mmol, sodium chloride 0.10 mmol, trishydroxymethylaminomethane 70 μmol and glycerol ca. 2 mmol (to make isotonicity). Zinc acetate 12 μmol was added, pH was adjusted to 7.4 and finally the volume adjusted to 8 mL by adding water.

AR: LysB29Nε-hexadecandioyl-γ-Glu desB30 human insulin 18 μmol was dissolved in water and mixed with an aqueous solution containing phenol 0.16 mmol, m-cresol 0.16 mmol, sodium chloride 0.10 mmol, trishydroxymethylaminomethane 70 μmol and glycerol ca. 2 mmol (to make isotonicity). Zinc acetate 18 μmol was added, pH was adjusted to 7.4 and finally the volume adjusted to 8 mL by adding water.

AS: LysB29Nε-hexadecandioyl-γ-Glu desB30 human insulin 18 μmol was dissolved in water and mixed with an aqueous solution containing phenol 0.16 mmol, m-cresol 0.16 mmol, sodium chloride 0.10 mmol, trishydroxymethylaminomethane 70 μmol and glycerol ca. 2 mmol (to make isotonicity). Zinc acetate 24 μmol was added, pH was adjusted to 7.4 and finally the volume adjusted to 8 mL by adding water.

AT: LysB29Nε-hexadecandioyl-γ-Glu desB30 human insulin 24 μmol was dissolved in water and mixed with an aqueous solution containing phenol 0.16 mmol, m-cresol 0.16 mmol, sodium chloride 0.10 mmol, trishydroxymethylaminomethane 70 μmol and glycerol ca. 2 mmol (to make isotonicity). Zinc acetate 12 μmol was added, pH was adjusted to 7.4 and finally the volume adjusted to 8 mL by adding water.

AU: LysB29Nε-hexadecandioyl-γ-Glu desB30 human insulin 24 μmol was dissolved in water and mixed with an aqueous solution containing phenol 0.16 mmol, m-cresol 0.16 mmol, sodium chloride 0.10 mmol, trishydroxymethylaminomethane 70 μmol and glycerol ca. 2 mmol (to make isotonicity). Zinc acetate 16 μmol was added, pH was adjusted to 7.4 and finally the volume adjusted to 8 mL by adding water.

AV: LysB29Nε-hexadecandioyl-γ-Glu desB30 human insulin 24 μmol was dissolved in water and mixed with an aqueous solution containing phenol 0.16 mmol, m-cresol 0.16 mmol, sodium chloride 0.10 mmol, trishydroxymethylaminomethane 70 μmol and glycerol ca. 2 mmol (to make isotonicity). Zinc acetate 24 μmol was added, pH was adjusted to 7.4 and finally the volume adjusted to 8 mL by adding water.

AX: LysB29Nε-hexadecandioyl-γ-Glu desB30 human insulin 24 μmol was dissolved in water and mixed with an aqueous solution containing phenol 0.16 mmol, m-cresol 0.16 mmol, sodium chloride 0.10 mmol, trishydroxymethylaminomethane 70 μmol and glycerol ca. 2 mmol (to make isotonicity). Zinc acetate 32 μmol was added, pH was adjusted to 7.4 and finally the volume adjusted to 8 mL by adding water.

AY: LysB29Nε-hexadecandioyl-γ-Glu desB30 human insulin 12 µmol was dissolved in water and mixed with an aqueous solution containing phenol 0.19 mmol, m-cresol 0.19 mmol, sodium chloride 0.10 mmol, trishydroxymethylaminomethane 70 µmol and glycerol ca. 2 mmol (to make isotonicity). Zinc acetate 6 µmol was added, pH was adjusted to 7.4 and finally the volume adjusted to 8 mL by adding water.

AZ: LysB29Nε-hexadecandioyl-γ-Glu desB30 human insulin 12 µmol was dissolved in water and mixed with an aqueous solution containing phenol 0.19 mmol, m-cresol 0.19 mmol, sodium chloride 0.10 mmol, trishydroxymethylaminomethane 70 µmol and glycerol ca. 2 mmol (to make isotonicity). Zinc acetate 8 µmol was added, pH was adjusted to 7.4 and finally the volume adjusted to 8 mL by adding water.

BA: LysB29Nε-hexadecandioyl-γ-Glu desB30 human insulin 12 µmol was dissolved in water and mixed with an aqueous solution containing phenol 0.19 mmol, m-cresol 0.19 mmol, sodium chloride 0.10 mmol, trishydroxymethylaminomethane 70 µmol and glycerol ca. 2 mmol (to make isotonicity). Zinc acetate 12 µmol was added, pH was adjusted to 7.4 and finally the volume adjusted to 8 mL by adding water.

BB: LysB29Nε-hexadecandioyl-γ-Glu desB30 human insulin 12 µmol was dissolved in water and mixed with an aqueous solution containing phenol 0.19 mmol, m-cresol 0.19 mmol, sodium chloride 0.10 mmol, trishydroxymethylaminomethane 70 µmol and glycerol ca. 2 mmol (to make isotonicity). Zinc acetate 16 µmol was added, pH was adjusted to 7.4 and finally the volume adjusted to 8 mL by adding water.

BC: LysB29Nε-hexadecandioyl-γ-Glu desB30 human insulin 18 µmol was dissolved in water and mixed with an aqueous solution containing phenol 0.19 mmol, m-cresol 0.19 mmol, sodium chloride 0.10 mmol, trishydroxymethylaminomethane 70 µmol and glycerol ca. 2 mmol (to make isotonicity). Zinc acetate 9 µmol was added, pH was adjusted to 7.4 and finally the volume adjusted to 8 mL by adding water.

BD: LysB29Nε-hexadecandioyl-γ-Glu desB30 human insulin 18 µmol was dissolved in water and mixed with an aqueous solution containing phenol 0.19 mmol, m-cresol 0.19 mmol, sodium chloride 0.10 mmol, trishydroxymethylaminomethane 70 µmol and glycerol ca. 2 mmol (to make isotonicity). Zinc acetate 12 µmol was added, pH was adjusted to 7.4 and finally the volume adjusted to 8 mL by adding water.

BE: LysB29Nε-hexadecandioyl-γ-Glu desB30 human insulin 18 µmol was dissolved in water and mixed with an aqueous solution containing phenol 0.19 mmol, m-cresol 0.19 mmol, sodium chloride 0.10 mmol, trishydroxymethylaminomethane 70 µmol and glycerol ca. 2 mmol (to make isotonicity). Zinc acetate 18 µmol was added, pH was adjusted to 7.4 and finally the volume adjusted to 8 mL by adding water.

BF: LysB29Nε-hexadecandioyl-γ-Glu desB30 human insulin 18 µmol was dissolved in water and mixed with an aqueous solution containing phenol 0.19 mmol, m-cresol 0.19 mmol, sodium chloride 0.10 mmol, trishydroxymethylaminomethane 70 µmol and glycerol ca. 2 mmol (to make isotonicity). Zinc acetate 24 µmol was added, pH was adjusted to 7.4 and finally the volume adjusted to 8 mL by adding water.

BG: LysB29Nε-hexadecandioyl-γ-Glu desB30 human insulin 24 µmol was dissolved in water and mixed with an aqueous solution containing phenol 0.19 mmol, m-cresol 0.19 mmol, sodium chloride 0.10 mmol, trishydroxymethylaminomethane 70 µmol and glycerol ca. 2 mmol (to make isotonicity). Zinc acetate 12 µmol was added, pH was adjusted to 7.4 and finally the volume adjusted to 8 mL by adding water.

BH: LysB29Nε-hexadecandioyl-γ-Glu desB30 human insulin 24 µmol was dissolved in water and mixed with an aqueous solution containing phenol 0.19 mmol, m-cresol 0.19 mmol, sodium chloride 0.10 mmol, trishydroxymethylaminomethane 70 µmol and glycerol ca. 2 mmol (to make isotonicity). Zinc acetate 16 µmol was added, pH was adjusted to 7.4 and finally the volume adjusted to 8 mL by adding water.

BI: LysB29Nε-hexadecandioyl-γ-Glu desB30 human insulin 24 µmol was dissolved in water and mixed with an aqueous solution containing phenol 0.19 mmol, m-cresol 0.19 mmol, sodium chloride 0.10 mmol, trishydroxymethylaminomethane 70 µmol and glycerol ca. 2 mmol (to make isotonicity). Zinc acetate 24 µmol was added, pH was adjusted to 7.4 and finally the volume adjusted to 8 mL by adding water.

BJ: LysB29Nε-hexadecandioyl-γ-Glu desB30 human insulin 24 µmol was dissolved in water and mixed with an aqueous solution containing phenol 0.19 mmol, m-cresol 0.19 mmol, sodium chloride 0.10 mmol, trishydroxymethylaminomethane 70 µmol and glycerol ca. 2 mmol (to make isotonicity). Zinc acetate 32 µmol was added, pH was adjusted to 7.4 and finally the volume adjusted to 8 mL by adding water.

BK: A formulation consisting of insulin aspart and an insulin derivative was obtained by mixing 0.8 mL of formulation A with 7.2 mL of formulation M and finally the volume was adjusted to 10 mL by adding water.

BL: A formulation consisting of insulin aspart and an insulin derivative was obtained by mixing 1.6 mL of formulation A with 6.4 mL of formulation M and finally the volume was adjusted to 10 mL by adding water.

BM: A formulation consisting of insulin aspart and an insulin derivative was obtained by mixing 2.4 mL of formulation A with 5.6 mL of formulation M and finally the volume was adjusted to 10 mL by adding water.

BN: A formulation consisting of insulin aspart and an insulin derivative was obtained by mixing 3.2 mL of formulation A with 4.8 mL of formulation M and finally the volume was adjusted to 10 mL by adding water.

BO: A formulation consisting of insulin aspart and an insulin derivative was obtained by mixing 4.0 mL of formulation A with 4.0 mL of formulation M and finally the volume was adjusted to 10 mL by adding water.

BP: A formulation consisting of insulin aspart and an insulin derivative was obtained by mixing 4.8 mL of formulation A with 3.2 mL of formulation M and finally the volume was adjusted to 10 mL by adding water.

BQ: A formulation consisting of insulin aspart and an insulin derivative was obtained by mixing 5.6 mL of formulation A with 2.4 mL of formulation M and finally the volume was adjusted to 10 mL by adding water.

BR: A formulation consisting of insulin aspart and an insulin derivative was obtained by mixing 6.4 mL of formulation A with 1.6 mL of formulation M and finally the volume was adjusted to 10 mL by adding water.

BS: A formulation consisting of insulin aspart and an insulin derivative was obtained by mixing 7.2 mL of formulation A with 0.8 mL of formulation M and finally the volume was adjusted to 10 mL by adding water.

BT: A formulation consisting of insulin aspart and an insulin derivative was obtained by mixing 0.8 mL of formulation A with 7.2 mL of formulation N and finally the volume was adjusted to 10 mL by adding water.

BU: A formulation consisting of insulin aspart and an insulin derivative was obtained by mixing 1.6 mL of formulation A with 6.4 mL of formulation N and finally the volume was adjusted to 10 mL by adding water.

BV: A formulation consisting of insulin aspart and an insulin derivative was obtained by mixing 2.4 mL of formulation A with 5.6 mL of formulation N and finally the volume was adjusted to 10 mL by adding water.

BX: A formulation consisting of insulin aspart and an insulin derivative was obtained by mixing 3.2 mL of formulation A with 4.8 mL of formulation N and finally the volume was adjusted to 10 mL by adding water.

BY: A formulation consisting of insulin aspart and an insulin derivative was obtained by mixing 4.0 mL of formulation A with 4.0 mL of formulation N and finally the volume was adjusted to 10 mL by adding water.

BZ: A formulation consisting of insulin aspart and an insulin derivative was obtained by mixing 4.8 mL of formulation A with 3.2 mL of formulation N and finally the volume was adjusted to 10 mL by adding water.

CA: A formulation consisting of insulin aspart and an insulin derivative was obtained by mixing 5.6 mL of formulation A with 2.4 mL of formulation N and finally the volume was adjusted to 10 mL by adding water.

CB: A formulation consisting of insulin aspart and an insulin derivative was obtained by mixing 6.4 mL of formulation A with 1.6 mL of formulation N and finally the volume was adjusted to 10 mL by adding water.

CC: A formulation consisting of insulin aspart and an insulin derivative was obtained by mixing 7.2 mL of formulation A with 0.8 mL of formulation N and finally the volume was adjusted to 10 mL by adding water.

CD: A formulation consisting of insulin aspart and an insulin derivative was obtained by mixing 0.8 mL of formulation A with 7.2 mL of formulation 0 and finally the volume was adjusted to 10 mL by adding water.

CE: A formulation consisting of insulin aspart and an insulin derivative was obtained by mixing 1.6 mL of formulation A with 6.4 mL of formulation 0 and finally the volume was adjusted to 10 mL by adding water.

CF: A formulation consisting of insulin aspart and an insulin derivative was obtained by mixing 2.4 mL of formulation A with 5.6 mL of formulation 0 and finally the volume was adjusted to 10 mL by adding water.

CG: A formulation consisting of insulin aspart and an insulin derivative was obtained by mixing 3.2 mL of formulation A with 4.8 mL of formulation 0 and finally the volume was adjusted to 10 mL by adding water.

CH: A formulation consisting of insulin aspart and an insulin derivative was obtained by mixing 4.0 mL of formulation A with 4.0 mL of formulation 0 and finally the volume was adjusted to 10 mL by adding water.

CI: A formulation consisting of insulin aspart and an insulin derivative was obtained by mixing 4.8 mL of formulation A with 3.2 mL of formulation 0 and finally the volume was adjusted to 10 mL by adding water.

CJ: A formulation consisting of insulin aspart and an insulin derivative was obtained by mixing 5.6 mL of formulation A with 2.4 mL of formulation 0 and finally the volume was adjusted to 10 mL by adding water.

CK: A formulation consisting of insulin aspart and an insulin derivative was obtained by mixing 6.4 mL of formulation A with 1.6 mL of formulation 0 and finally the volume was adjusted to 10 mL by adding water.

CL: A formulation consisting of insulin aspart and an insulin derivative was obtained by mixing 7.2 mL of formulation A with 0.8 mL of formulation 0 and finally the volume was adjusted to 10 mL by adding water.

CM: A formulation consisting of insulin aspart and an insulin derivative was obtained by mixing 0.8 mL of formulation A with 7.2 mL of formulation P and finally the volume was adjusted to 10 mL by adding water.

CN: A formulation consisting of insulin aspart and an insulin derivative was obtained by mixing 1.6 mL of formulation A with 6.4 mL of formulation P and finally the volume was adjusted to 10 mL by adding water.

CO: A formulation consisting of insulin aspart and an insulin derivative was obtained by mixing 2.4 mL of formulation A with 5.6 mL of formulation P and finally the volume was adjusted to 10 mL by adding water.

CP: A formulation consisting of insulin aspart and an insulin derivative was obtained by mixing 3.2 mL of formulation A with 4.8 mL of formulation P and finally the volume was adjusted to 10 mL by adding water.

CQ: A formulation consisting of insulin aspart and an insulin derivative was obtained by mixing 4.0 mL of formulation A with 4.0 mL of formulation P and finally the volume was adjusted to 10 mL by adding water.

CR: A formulation consisting of insulin aspart and an insulin derivative was obtained by mixing 4.8 mL of formulation A with 3.2 mL of formulation P and finally the volume was adjusted to 10 mL by adding water.

CS: A formulation consisting of insulin aspart and an insulin derivative was obtained by mixing 5.6 mL of formulation A with 2.4 mL of formulation P and finally the volume was adjusted to 10 mL by adding water.

CT: A formulation consisting of insulin aspart and an insulin derivative was obtained by mixing 6.4 mL of formulation A with 1.6 mL of formulation P and finally the volume was adjusted to 10 mL by adding water.

CU: A formulation consisting of insulin aspart and an insulin derivative was obtained by mixing 7.2 mL of formulation A with 0.8 mL of formulation P and finally the volume was adjusted to 10 mL by adding water.

CV: A formulation consisting of insulin aspart and an insulin derivative was obtained by mixing 0.8 mL of formulation B with 7.2 mL of formulation Q and finally the volume was adjusted to 10 mL by adding water.

CX: A formulation consisting of insulin aspart and an insulin derivative was obtained by mixing 1.6 mL of formulation B with 6.4 mL of formulation Q and finally the volume was adjusted to 10 mL by adding water.

CY: A formulation consisting of insulin aspart and an insulin derivative was obtained by mixing 2.4 mL of formulation B with 5.6 mL of formulation Q and finally the volume was adjusted to 10 mL by adding water.

CZ: A formulation consisting of insulin aspart and an insulin derivative was obtained by mixing 3.2 mL of formulation B with 4.8 mL of formulation Q and finally the volume was adjusted to 10 mL by adding water.

DA: A formulation consisting of insulin aspart and an insulin derivative was obtained by mixing 4.0 mL of formulation B with 4.0 mL of formulation Q and finally the volume was adjusted to 10 mL by adding water.

DB: A formulation consisting of insulin aspart and an insulin derivative was obtained by mixing 4.8 mL of formulation B with 3.2 mL of formulation Q and finally the volume was adjusted to 10 mL by adding water.

DC: A formulation consisting of insulin aspart and an insulin derivative was obtained by mixing 5.6 mL of formulation B with 2.4 mL of formulation Q and finally the volume was adjusted to 10 mL by adding water.

DD: A formulation consisting of insulin aspart and an insulin derivative was obtained by mixing 6.4 mL of formulation B with 1.6 mL of formulation Q and finally the volume was adjusted to 10 mL by adding water.

DE: A formulation consisting of insulin aspart and an insulin derivative was obtained by mixing 7.2 mL of formulation B with 0.8 mL of formulation Q and finally the volume was adjusted to 10 mL by adding water.

DF: A formulation consisting of insulin aspart and an insulin derivative was obtained by mixing 0.8 mL of formulation B with 7.2 mL of formulation R and finally the volume was adjusted to 10 mL by adding water.

DG: A formulation consisting of insulin aspart and an insulin derivative was obtained by mixing 1.6 mL of formulation B with 6.4 mL of formulation R and finally the volume was adjusted to 10 mL by adding water.

DH: A formulation consisting of insulin aspart and an insulin derivative was obtained by mixing 2.4 mL of formulation B with 5.6 mL of formulation R and finally the volume was adjusted to 10 mL by adding water.

DI: A formulation consisting of insulin aspart and an insulin derivative was obtained by mixing 3.2 mL of formulation B with 4.8 mL of formulation R and finally the volume was adjusted to 10 mL by adding water.

DJ: A formulation consisting of insulin aspart and an insulin derivative was obtained by mixing 4.0 mL of formulation B with 4.0 mL of formulation R and finally the volume was adjusted to 10 mL by adding water.

DK: A formulation consisting of insulin aspart and an insulin derivative was obtained by mixing 4.8 mL of formulation B with 3.2 mL of formulation R and finally the volume was adjusted to 10 mL by adding water.

DL: A formulation consisting of insulin aspart and an insulin derivative was obtained by mixing 5.6 mL of formulation B with 2.4 mL of formulation R and finally the volume was adjusted to 10 mL by adding water.

DM: A formulation consisting of insulin aspart and an insulin derivative was obtained by mixing 6.4 mL of formulation B with 1.6 mL of formulation R and finally the volume was adjusted to 10 mL by adding water.

DN: A formulation consisting of insulin aspart and an insulin derivative was obtained by mixing 7.2 mL of formulation B with 0.8 mL of formulation R and finally the volume was adjusted to 10 mL by adding water.

DO: A formulation consisting of insulin aspart and an insulin derivative was obtained by mixing 0.8 mL of formulation B with 7.2 mL of formulation S and finally the volume was adjusted to 10 mL by adding water.

DP: A formulation consisting of insulin aspart and an insulin derivative was obtained by mixing 1.6 mL of formulation B with 6.4 mL of formulation S and finally the volume was adjusted to 10 mL by adding water.

DQ: A formulation consisting of insulin aspart and an insulin derivative was obtained by mixing 2.4 mL of formulation B with 5.6 mL of formulation S and finally the volume was adjusted to 10 mL by adding water.

DR: A formulation consisting of insulin aspart and an insulin derivative was obtained by mixing 3.2 mL of formulation B with 4.8 mL of formulation S and finally the volume was adjusted to 10 mL by adding water.

DS: A formulation consisting of insulin aspart and an insulin derivative was obtained by mixing 4.0 mL of formulation B with 4.0 mL of formulation S and finally the volume was adjusted to 10 mL by adding water.

DT: A formulation consisting of insulin aspart and an insulin derivative was obtained by mixing 4.8 mL of formulation B with 3.2 mL of formulation S and finally the volume was adjusted to 10 mL by adding water.

DU: A formulation consisting of insulin aspart and an insulin derivative was obtained by mixing 5.6 mL of formulation B with 2.4 mL of formulation S and finally the volume was adjusted to 10 mL by adding water.

DV: A formulation consisting of insulin aspart and an insulin derivative was obtained by mixing 6.4 mL of formulation B with 1.6 mL of formulation S and finally the volume was adjusted to 10 mL by adding water.

DX: A formulation consisting of insulin aspart and an insulin derivative was obtained by mixing 7.2 mL of formulation B with 0.8 mL of formulation S and finally the volume was adjusted to 10 mL by adding water.

DY: A formulation consisting of insulin aspart and an insulin derivative was obtained by mixing 0.8 mL of formulation B with 7.2 mL of formulation T and finally the volume was adjusted to 10 mL by adding water.

DZ: A formulation consisting of insulin aspart and an insulin derivative was obtained by mixing 1.6 mL of formulation B with 6.4 mL of formulation T and finally the volume was adjusted to 10 mL by adding water.

EA: A formulation consisting of insulin aspart and an insulin derivative was obtained by mixing 2.4 mL of formulation B with 5.6 mL of formulation T and finally the volume was adjusted to 10 mL by adding water.

EB: A formulation consisting of insulin aspart and an insulin derivative was obtained by mixing 3.2 mL of formulation B with 4.8 mL of formulation T and finally the volume was adjusted to 10 mL by adding water.

EC: A formulation consisting of insulin aspart and an insulin derivative was obtained by mixing 4.0 mL of formulation B with 4.0 mL of formulation T and finally the volume was adjusted to 10 mL by adding water.

ED: A formulation consisting of insulin aspart and an insulin derivative was obtained by mixing 4.8 mL of formulation B with 3.2 mL of formulation T and finally the volume was adjusted to 10 mL by adding water.

EE: A formulation consisting of insulin aspart and an insulin derivative was obtained by mixing 5.6 mL of formulation B with 2.4 mL of formulation T and finally the volume was adjusted to 10 mL by adding water.

EF: A formulation consisting of insulin aspart and an insulin derivative was obtained by mixing 6.4 mL of formulation B with 1.6 mL of formulation T and finally the volume was adjusted to 10 mL by adding water.

EG: A formulation consisting of insulin aspart and an insulin derivative was obtained by mixing 7.2 mL of formulation B with 0.8 mL of formulation T and finally the volume was adjusted to 10 mL by adding water.

EH: A formulation consisting of insulin aspart and an insulin derivative was obtained by mixing 0.8 mL of formulation C with 7.2 mL of formulation U and finally the volume was adjusted to 10 mL by adding water.

EI: A formulation consisting of insulin aspart and an insulin derivative was obtained by mixing 1.6 mL of formulation C with 6.4 mL of formulation U and finally the volume was adjusted to 10 mL by adding water.

EJ: A formulation consisting of insulin aspart and an insulin derivative was obtained by mixing 2.4 mL of formulation C with 5.6 mL of formulation U and finally the volume was adjusted to 10 mL by adding water.

EK: A formulation consisting of insulin aspart and an insulin derivative was obtained by mixing 3.2 mL of formulation C with 4.8 mL of formulation U and finally the volume was adjusted to 10 mL by adding water.

EL: A formulation consisting of insulin aspart and an insulin derivative was obtained by mixing 4.0 mL of formulation C with 4.0 mL of formulation U and finally the volume was adjusted to 10 mL by adding water.

EM: A formulation consisting of insulin aspart and an insulin derivative was obtained by mixing 4.8 mL of formulation C with 3.2 mL of formulation U and finally the volume was adjusted to 10 mL by adding water.

EN: A formulation consisting of insulin aspart and an insulin derivative was obtained by mixing 5.6 mL of formulation C with 2.4 mL of formulation U and finally the volume was adjusted to 10 mL by adding water.

EO: A formulation consisting of insulin aspart and an insulin derivative was obtained by mixing 6.4 mL of formulation C with 1.6 mL of formulation U and finally the volume was adjusted to 10 mL by adding water.

EP: A formulation consisting of insulin aspart and an insulin derivative was obtained by mixing 7.2 mL of formulation C with 0.8 mL of formulation U and finally the volume was adjusted to 10 mL by adding water.

EQ: A formulation consisting of insulin aspart and an insulin derivative was obtained by mixing 0.8 mL of formulation C with 7.2 mL of formulation V and finally the volume was adjusted to 10 mL by adding water.

ER: A formulation consisting of insulin aspart and an insulin derivative was obtained by mixing 1.6 mL of formulation C with 6.4 mL of formulation V and finally the volume was adjusted to 10 mL by adding water.

ES: A formulation consisting of insulin aspart and an insulin derivative was obtained by mixing 2.4 mL of formulation C with 5.6 mL of formulation V and finally the volume was adjusted to 10 mL by adding water.

ET: A formulation consisting of insulin aspart and an insulin derivative was obtained by mixing 3.2 mL of formulation C with 4.8 mL of formulation V and finally the volume was adjusted to 10 mL by adding water.

EU: A formulation consisting of insulin aspart and an insulin derivative was obtained by mixing 4.0 mL of formulation C with 4.0 mL of formulation V and finally the volume was adjusted to 10 mL by adding water.

EV: A formulation consisting of insulin aspart and an insulin derivative was obtained by mixing 4.8 mL of formulation C with 3.2 mL of formulation V and finally the volume was adjusted to 10 mL by adding water.

EX: A formulation consisting of insulin aspart and an insulin derivative was obtained by mixing 5.6 mL of formulation C with 2.4 mL of formulation V and finally the volume was adjusted to 10 mL by adding water.

EY: A formulation consisting of insulin aspart and an insulin derivative was obtained by mixing 6.4 mL of formulation C with 1.6 mL of formulation V and finally the volume was adjusted to 10 mL by adding water.

EZ: A formulation consisting of insulin aspart and an insulin derivative was obtained by mixing 7.2 mL of formulation C with 0.8 mL of formulation V and finally the volume was adjusted to 10 mL by adding water.

FA: A formulation consisting of insulin aspart and an insulin derivative was obtained by mixing 0.8 mL of formulation C with 7.2 mL of formulation X and finally the volume was adjusted to 10 mL by adding water.

FB: A formulation consisting of insulin aspart and an insulin derivative was obtained by mixing 1.6 mL of formulation C with 6.4 mL of formulation X and finally the volume was adjusted to 10 mL by adding water.

FC: A formulation consisting of insulin aspart and an insulin derivative was obtained by mixing 2.4 mL of formulation C with 5.6 mL of formulation X and finally the volume was adjusted to 10 mL by adding water.

FD: A formulation consisting of insulin aspart and an insulin derivative was obtained by mixing 3.2 mL of formulation C with 4.8 mL of formulation X and finally the volume was adjusted to 10 mL by adding water.

FE: A formulation consisting of insulin aspart and an insulin derivative was obtained by mixing 4.0 mL of formulation C with 4.0 mL of formulation X and finally the volume was adjusted to 10 mL by adding water.

FF: A formulation consisting of insulin aspart and an insulin derivative was obtained by mixing 4.8 mL of formulation C with 3.2 mL of formulation X and finally the volume was adjusted to 10 mL by adding water.

FG: A formulation consisting of insulin aspart and an insulin derivative was obtained by mixing 5.6 mL of formulation C with 2.4 mL of formulation X and finally the volume was adjusted to 10 mL by adding water.

FH: A formulation consisting of insulin aspart and an insulin derivative was obtained by mixing 6.4 mL of formulation C with 1.6 mL of formulation X and finally the volume was adjusted to 10 mL by adding water.

FI: A formulation consisting of insulin aspart and an insulin derivative was obtained by mixing 7.2 mL of formulation C with 0.8 mL of formulation X and finally the volume was adjusted to 10 mL by adding water.

FJ: A formulation consisting of insulin aspart and an insulin derivative was obtained by mixing 0.8 mL of formulation C with 7.2 mL of formulation Y and finally the volume was adjusted to 10 mL by adding water.

FK: A formulation consisting of insulin aspart and an insulin derivative was obtained by mixing 1.6 mL of formulation C with 6.4 mL of formulation Y and finally the volume was adjusted to 10 mL by adding water.

FL: A formulation consisting of insulin aspart and an insulin derivative was obtained by mixing 2.4 mL of formulation C with 5.6 mL of formulation Y and finally the volume was adjusted to 10 mL by adding water.

FM: A formulation consisting of insulin aspart and an insulin derivative was obtained by mixing 3.2 mL of formulation C with 4.8 mL of formulation Y and finally the volume was adjusted to 10 mL by adding water.

FN: A formulation consisting of insulin aspart and an insulin derivative was obtained by mixing 4.0 mL of formulation C with 4.0 mL of formulation Y and finally the volume was adjusted to 10 mL by adding water.

FO: A formulation consisting of insulin aspart and an insulin derivative was obtained by mixing 4.8 mL of formulation C with 3.2 mL of formulation Y and finally the volume was adjusted to 10 mL by adding water.

FP: A formulation consisting of insulin aspart and an insulin derivative was obtained by mixing 5.6 mL of formulation C with 2.4 mL of formulation Y and finally the volume was adjusted to 10 mL by adding water.

FQ: A formulation consisting of insulin aspart and an insulin derivative was obtained by mixing 6.4 mL of formulation C with 1.6 mL of formulation Y and finally the volume was adjusted to 10 mL by adding water.

FR: A formulation consisting of insulin aspart and an insulin derivative was obtained by mixing 7.2 mL of formulation C with 0.8 mL of formulation Y and finally the volume was adjusted to 10 mL by adding water.

FS: A formulation consisting of insulin aspart and an insulin derivative was obtained by mixing 0.8 mL of formulation D with 7.2 mL of formulation Z and finally the volume was adjusted to 10 mL by adding water.

FT: A formulation consisting of insulin aspart and an insulin derivative was obtained by mixing 1.6 mL of formulation D with 6.4 mL of formulation Z and finally the volume was adjusted to 10 mL by adding water.

FU: A formulation consisting of insulin aspart and an insulin derivative was obtained by mixing 2.4 mL of formulation D with 5.6 mL of formulation Z and finally the volume was adjusted to 10 mL by adding water.

FV: A formulation consisting of insulin aspart and an insulin derivative was obtained by mixing 3.2 mL of formulation D with 4.8 mL of formulation Z and finally the volume was adjusted to 10 mL by adding water.

FX: A formulation consisting of insulin aspart and an insulin derivative was obtained by mixing 4.0 mL of formulation D with 4.0 mL of formulation Z and finally the volume was adjusted to 10 mL by adding water.

FY: A formulation consisting of insulin aspart and an insulin derivative was obtained by mixing 4.8 mL of formulation D with 3.2 mL of formulation Z and finally the volume was adjusted to 10 mL by adding water.

FZ: A formulation consisting of insulin aspart and an insulin derivative was obtained by mixing 5.6 mL of formulation D with 2.4 mL of formulation Z and finally the volume was adjusted to 10 mL by adding water.

GA: A formulation consisting of insulin aspart and an insulin derivative was obtained by mixing 6.4 mL of formulation D with 1.6 mL of formulation Z and finally the volume was adjusted to 10 mL by adding water.

GB: A formulation consisting of insulin aspart and an insulin derivative was obtained by mixing 7.2 mL of formulation D with 0.8 mL of formulation Z and finally the volume was adjusted to 10 mL by adding water.

GC: A formulation consisting of insulin aspart and an insulin derivative was obtained by mixing 0.8 mL of formulation D with 7.2 mL of formulation AA and finally the volume was adjusted to 10 mL by adding water.

GD: A formulation consisting of insulin aspart and an insulin derivative was obtained by mixing 1.6 mL of formulation D with 6.4 mL of formulation AA and finally the volume was adjusted to 10 mL by adding water.

GE: A formulation consisting of insulin aspart and an insulin derivative was obtained by mixing 2.4 mL of formulation D with 5.6 mL of formulation AA and finally the volume was adjusted to 10 mL by adding water.

GF: A formulation consisting of insulin aspart and an insulin derivative was obtained by mixing 3.2 mL of formulation D with 4.8 mL of formulation AA and finally the volume was adjusted to 10 mL by adding water.

GG: A formulation consisting of insulin aspart and an insulin derivative was obtained by mixing 4.0 mL of formulation D with 4.0 mL of formulation AA and finally the volume was adjusted to 10 mL by adding water.

GH: A formulation consisting of insulin aspart and an insulin derivative was obtained by mixing 4.8 mL of formulation D with 3.2 mL of formulation AA and finally the volume was adjusted to 10 mL by adding water.

GI: A formulation consisting of insulin aspart and an insulin derivative was obtained by mixing 5.6 mL of formulation D with 2.4 mL of formulation AA and finally the volume was adjusted to 10 mL by adding water.

GJ: A formulation consisting of insulin aspart and an insulin derivative was obtained by mixing 6.4 mL of formulation D with 1.6 mL of formulation AA and finally the volume was adjusted to 10 mL by adding water.

GK: A formulation consisting of insulin aspart and an insulin derivative was obtained by mixing 7.2 mL of formulation D with 0.8 mL of formulation AA and finally the volume was adjusted to 10 mL by adding water.

GL: A formulation consisting of insulin aspart and an insulin derivative was obtained by mixing 0.8 mL of formulation D with 7.2 mL of formulation AB and finally the volume was adjusted to 10 mL by adding water.

GM: A formulation consisting of insulin aspart and an insulin derivative was obtained by mixing 1.6 mL of formulation D with 6.4 mL of formulation AB and finally the volume was adjusted to 10 mL by adding water.

GN: A formulation consisting of insulin aspart and an insulin derivative was obtained by mixing 2.4 mL of formulation D with 5.6 mL of formulation AB and finally the volume was adjusted to 10 mL by adding water.

GO: A formulation consisting of insulin aspart and an insulin derivative was obtained by mixing 3.2 mL of formulation D with 4.8 mL of formulation AB and finally the volume was adjusted to 10 mL by adding water.

GP: A formulation consisting of insulin aspart and an insulin derivative was obtained by mixing 4.0 mL of formulation D with 4.0 mL of formulation AB and finally the volume was adjusted to 10 mL by adding water.

GQ: A formulation consisting of insulin aspart and an insulin derivative was obtained by mixing 4.8 mL of formulation D with 3.2 mL of formulation AB and finally the volume was adjusted to 10 mL by adding water.

GR: A formulation consisting of insulin aspart and an insulin derivative was obtained by mixing 5.6 mL of formulation D with 2.4 mL of formulation AB and finally the volume was adjusted to 10 mL by adding water.

GS: A formulation consisting of insulin aspart and an insulin derivative was obtained by mixing 6.4 mL of formulation D with 1.6 mL of formulation AB and finally the volume was adjusted to 10 mL by adding water.

GT: A formulation consisting of insulin aspart and an insulin derivative was obtained by mixing 7.2 mL of formulation D with 0.8 mL of formulation AB and finally the volume was adjusted to 10 mL by adding water.

GU: A formulation consisting of insulin aspart and an insulin derivative was obtained by mixing 0.8 mL of formulation D with 7.2 mL of formulation AC and finally the volume was adjusted to 10 mL by adding water.

GV: A formulation consisting of insulin aspart and an insulin derivative was obtained by mixing 1.6 mL of formulation D with 6.4 mL of formulation AC and finally the volume was adjusted to 10 mL by adding water.

GX: A formulation consisting of insulin aspart and an insulin derivative was obtained by mixing 2.4 mL of formulation D with 5.6 mL of formulation AC and finally the volume was adjusted to 10 mL by adding water.

GY: A formulation consisting of insulin aspart and an insulin derivative was obtained by mixing 3.2 mL of formulation D with 4.8 mL of formulation AC and finally the volume was adjusted to 10 mL by adding water.

GZ: A formulation consisting of insulin aspart and an insulin derivative was obtained by mixing 4.0 mL of formulation D with 4.0 mL of formulation AC and finally the volume was adjusted to 10 mL by adding water.

HA: A formulation consisting of insulin aspart and an insulin derivative was obtained by mixing 4.8 mL of formulation D with 3.2 mL of formulation AC and finally the volume was adjusted to 10 mL by adding water.

HB: A formulation consisting of insulin aspart and an insulin derivative was obtained by mixing 5.6 mL of formulation D with 2.4 mL of formulation AC and finally the volume was adjusted to 10 mL by adding water.

HC: A formulation consisting of insulin aspart and an insulin derivative was obtained by mixing 6.4 mL of formulation D with 1.6 mL of formulation AC and finally the volume was adjusted to 10 mL by adding water.

HD: A formulation consisting of insulin aspart and an insulin derivative was obtained by mixing 7.2 mL of formulation D with 0.8 mL of formulation AC and finally the volume was adjusted to 10 mL by adding water.

HE: A formulation consisting of insulin aspart and an insulin derivative was obtained by mixing 0.8 mL of formulation E with 7.2 mL of formulation AD and finally the volume was adjusted to 10 mL by adding water.

HF: A formulation consisting of insulin aspart and an insulin derivative was obtained by mixing 1.6 mL of formulation E with 6.4 mL of formulation AD and finally the volume was adjusted to 10 mL by adding water.

HG: A formulation consisting of insulin aspart and an insulin derivative was obtained by mixing 2.4 mL of formulation E with 5.6 mL of formulation AD and finally the volume was adjusted to 10 mL by adding water.

HH: A formulation consisting of insulin aspart and an insulin derivative was obtained by mixing 3.2 mL of formulation E with 4.8 mL of formulation AD and finally the volume was adjusted to 10 mL by adding water.

HI: A formulation consisting of insulin aspart and an insulin derivative was obtained by mixing 4.0 mL of formulation E with 4.0 mL of formulation AD and finally the volume was adjusted to 10 mL by adding water.

HJ: A formulation consisting of insulin aspart and an insulin derivative was obtained by mixing 4.8 mL of formulation E with 3.2 mL of formulation AD and finally the volume was adjusted to 10 mL by adding water.

HK: A formulation consisting of insulin aspart and an insulin derivative was obtained by mixing 5.6 mL of formulation E with 2.4 mL of formulation AD and finally the volume was adjusted to 10 mL by adding water.

HL: A formulation consisting of insulin aspart and an insulin derivative was obtained by mixing 6.4 mL of formulation E with 1.6 mL of formulation AD and finally the volume was adjusted to 10 mL by adding water.

HM: A formulation consisting of insulin aspart and an insulin derivative was obtained by mixing 7.2 mL of formulation E with 0.8 mL of formulation AD and finally the volume was adjusted to 10 mL by adding water.

HN: A formulation consisting of insulin aspart and an insulin derivative was obtained by mixing 0.8 mL of formulation E with 7.2 mL of formulation AE and finally the volume was adjusted to 10 mL by adding water.

HO: A formulation consisting of insulin aspart and an insulin derivative was obtained by mixing 1.6 mL of formulation E with 6.4 mL of formulation AE and finally the volume was adjusted to 10 mL by adding water.

HP: A formulation consisting of insulin aspart and an insulin derivative was obtained by mixing 2.4 mL of formulation E with 5.6 mL of formulation AE and finally the volume was adjusted to 10 mL by adding water.

HQ: A formulation consisting of insulin aspart and an insulin derivative was obtained by mixing 3.2 mL of formulation E with 4.8 mL of formulation AE and finally the volume was adjusted to 10 mL by adding water.

HR: A formulation consisting of insulin aspart and an insulin derivative was obtained by mixing 4.0 mL of formulation E with 4.0 mL of formulation AE and finally the volume was adjusted to 10 mL by adding water.

HS: A formulation consisting of insulin aspart and an insulin derivative was obtained by mixing 4.8 mL of formulation E with 3.2 mL of formulation AE and finally the volume was adjusted to 10 mL by adding water.

HT: A formulation consisting of insulin aspart and an insulin derivative was obtained by mixing 5.6 mL of formulation E with 2.4 mL of formulation AE and finally the volume was adjusted to 10 mL by adding water.

HU: A formulation consisting of insulin aspart and an insulin derivative was obtained by mixing 6.4 mL of formulation E with 1.6 mL of formulation AE and finally the volume was adjusted to 10 mL by adding water.

HV: A formulation consisting of insulin aspart and an insulin derivative was obtained by mixing 7.2 mL of formulation E with 0.8 mL of formulation AE and finally the volume was adjusted to 10 mL by adding water.

HX: A formulation consisting of insulin aspart and an insulin derivative was obtained by mixing 0.8 mL of formulation E with 7.2 mL of formulation AF and finally the volume was adjusted to 10 mL by adding water.

HY: A formulation consisting of insulin aspart and an insulin derivative was obtained by mixing 1.6 mL of formulation E with 6.4 mL of formulation AF and finally the volume was adjusted to 10 mL by adding water.

HZ: A formulation consisting of insulin aspart and an insulin derivative was obtained by mixing 2.4 mL of formulation E with 5.6 mL of formulation AF and finally the volume was adjusted to 10 mL by adding water.

IA: A formulation consisting of insulin aspart and an insulin derivative was obtained by mixing 3.2 mL of formulation E with 4.8 mL of formulation AF and finally the volume was adjusted to 10 mL by adding water.

IB: A formulation consisting of insulin aspart and an insulin derivative was obtained by mixing 4.0 mL of formulation E with 4.0 mL of formulation AF and finally the volume was adjusted to 10 mL by adding water.

IC: A formulation consisting of insulin aspart and an insulin derivative was obtained by mixing 4.8 mL of formulation E with 3.2 mL of formulation AF and finally the volume was adjusted to 10 mL by adding water.

ID: A formulation consisting of insulin aspart and an insulin derivative was obtained by mixing 5.6 mL of formulation E with 2.4 mL of formulation AF and finally the volume was adjusted to 10 mL by adding water.

IE: A formulation consisting of insulin aspart and an insulin derivative was obtained by mixing 6.4 mL of formulation E with 1.6 mL of formulation AF and finally the volume was adjusted to 10 mL by adding water.

IF: A formulation consisting of insulin aspart and an insulin derivative was obtained by mixing 7.2 mL of formulation E with 0.8 mL of formulation AF and finally the volume was adjusted to 10 mL by adding water.

IG: A formulation consisting of insulin aspart and an insulin derivative was obtained by mixing 0.8 mL of formulation E with 7.2 mL of formulation AG and finally the volume was adjusted to 10 mL by adding water.

IH: A formulation consisting of insulin aspart and an insulin derivative was obtained by mixing 1.6 mL of formulation E with 6.4 mL of formulation AG and finally the volume was adjusted to 10 mL by adding water.

II: A formulation consisting of insulin aspart and an insulin derivative was obtained by mixing 2.4 mL of formulation E with 5.6 mL of formulation AG and finally the volume was adjusted to 10 mL by adding water.

IJ: A formulation consisting of insulin aspart and an insulin derivative was obtained by mixing 3.2 mL of formulation E with 4.8 mL of formulation AG and finally the volume was adjusted to 10 mL by adding water.

IK: A formulation consisting of insulin aspart and an insulin derivative was obtained by mixing 4.0 mL of formulation E with 4.0 mL of formulation AG and finally the volume was adjusted to 10 mL by adding water.

IL: A formulation consisting of insulin aspart and an insulin derivative was obtained by mixing 4.8 mL of formulation E with 3.2 mL of formulation AG and finally the volume was adjusted to 10 mL by adding water.

IM: A formulation consisting of insulin aspart and an insulin derivative was obtained by mixing 5.6 mL of formulation E with 2.4 mL of formulation AG and finally the volume was adjusted to 10 mL by adding water.

IN: A formulation consisting of insulin aspart and an insulin derivative was obtained by mixing 6.4 mL of formulation E with 1.6 mL of formulation AG and finally the volume was adjusted to 10 mL by adding water.

IO: A formulation consisting of insulin aspart and an insulin derivative was obtained by mixing 7.2 mL of formulation E with 0.8 mL of formulation AG and finally the volume was adjusted to 10 mL by adding water.

IP: A formulation consisting of insulin aspart and an insulin derivative was obtained by mixing 0.8 mL of formulation F with 7.2 mL of formulation AH and finally the volume was adjusted to 10 mL by adding water.

IQ: A formulation consisting of insulin aspart and an insulin derivative was obtained by mixing 1.6 mL of formulation F with 6.4 mL of formulation AH and finally the volume was adjusted to 10 mL by adding water.

IR: A formulation consisting of insulin aspart and an insulin derivative was obtained by mixing 2.4 mL of formulation F with 5.6 mL of formulation AH and finally the volume was adjusted to 10 mL by adding water.

IS: A formulation consisting of insulin aspart and an insulin derivative was obtained by mixing 3.2 mL of formulation F with 4.8 mL of formulation AH and finally the volume was adjusted to 10 mL by adding water.

IT: A formulation consisting of insulin aspart and an insulin derivative was obtained by mixing 4.0 mL of formulation F with 4.0 mL of formulation AH and finally the volume was adjusted to 10 mL by adding water.

IU: A formulation consisting of insulin aspart and an insulin derivative was obtained by mixing 4.8 mL of formulation F with 3.2 mL of formulation AH and finally the volume was adjusted to 10 mL by adding water.

IV: A formulation consisting of insulin aspart and an insulin derivative was obtained by mixing 5.6 mL of formulation F with 2.4 mL of formulation AH and finally the volume was adjusted to 10 mL by adding water.

IX: A formulation consisting of insulin aspart and an insulin derivative was obtained by mixing 6.4 mL of formulation F with 1.6 mL of formulation AH and finally the volume was adjusted to 10 mL by adding water.

IY: A formulation consisting of insulin aspart and an insulin derivative was obtained by mixing 7.2 mL of formulation F with 0.8 mL of formulation AH and finally the volume was adjusted to 10 mL by adding water.

IZ: A formulation consisting of insulin aspart and an insulin derivative was obtained by mixing 0.8 mL of formulation F with 7.2 mL of formulation AI and finally the volume was adjusted to 10 mL by adding water.

JA: A formulation consisting of insulin aspart and an insulin derivative was obtained by mixing 1.6 mL of formulation F with 6.4 mL of formulation AI and finally the volume was adjusted to 10 mL by adding water.

JB: A formulation consisting of insulin aspart and an insulin derivative was obtained by mixing 2.4 mL of formulation F with 5.6 mL of formulation AI and finally the volume was adjusted to 10 mL by adding water.

JC: A formulation consisting of insulin aspart and an insulin derivative was obtained by mixing 3.2 mL of formulation F with 4.8 mL of formulation AI and finally the volume was adjusted to 10 mL by adding water.

JD: A formulation consisting of insulin aspart and an insulin derivative was obtained by mixing 4.0 mL of formulation F with 4.0 mL of formulation AI and finally the volume was adjusted to 10 mL by adding water.

JE: A formulation consisting of insulin aspart and an insulin derivative was obtained by mixing 4.8 mL of formulation F with 3.2 mL of formulation AI and finally the volume was adjusted to 10 mL by adding water.

JF: A formulation consisting of insulin aspart and an insulin derivative was obtained by mixing 5.6 mL of formulation F with 2.4 mL of formulation AI and finally the volume was adjusted to 10 mL by adding water.

JG: A formulation consisting of insulin aspart and an insulin derivative was obtained by mixing 6.4 mL of formulation F with 1.6 mL of formulation AI and finally the volume was adjusted to 10 mL by adding water.

JH: A formulation consisting of insulin aspart and an insulin derivative was obtained by mixing 7.2 mL of formulation F with 0.8 mL of formulation AI and finally the volume was adjusted to 10 mL by adding water.

JI: A formulation consisting of insulin aspart and an insulin derivative was obtained by mixing 0.8 mL of formulation F with 7.2 mL of formulation AJ and finally the volume was adjusted to 10 mL by adding water.

JJ: A formulation consisting of insulin aspart and an insulin derivative was obtained by mixing 1.6 mL of formulation F with 6.4 mL of formulation AJ and finally the volume was adjusted to 10 mL by adding water.

JK: A formulation consisting of insulin aspart and an insulin derivative was obtained by mixing 2.4 mL of formulation F with 5.6 mL of formulation AJ and finally the volume was adjusted to 10 mL by adding water.

JL: A formulation consisting of insulin aspart and an insulin derivative was obtained by mixing 3.2 mL of formulation F with 4.8 mL of formulation AJ and finally the volume was adjusted to 10 mL by adding water.

JM: A formulation consisting of insulin aspart and an insulin derivative was obtained by mixing 4.0 mL of formulation F with 4.0 mL of formulation AJ and finally the volume was adjusted to 10 mL by adding water.

JN: A formulation consisting of insulin aspart and an insulin derivative was obtained by mixing 4.8 mL of formulation F with 3.2 mL of formulation AJ and finally the volume was adjusted to 10 mL by adding water.

JO: A formulation consisting of insulin aspart and an insulin derivative was obtained by mixing 5.6 mL of formulation F with 2.4 mL of formulation AJ and finally the volume was adjusted to 10 mL by adding water.

JP: A formulation consisting of insulin aspart and an insulin derivative was obtained by mixing 6.4 mL of formulation F with 1.6 mL of formulation AJ and finally the volume was adjusted to 10 mL by adding water.

JQ: A formulation consisting of insulin aspart and an insulin derivative was obtained by mixing 7.2 mL of formulation F with 0.8 mL of formulation AJ and finally the volume was adjusted to 10 mL by adding water.

JR: A formulation consisting of insulin aspart and an insulin derivative was obtained by mixing 0.8 mL of formulation F with 7.2 mL of formulation AK and finally the volume was adjusted to 10 mL by adding water.

JS: A formulation consisting of insulin aspart and an insulin derivative was obtained by mixing 1.6 mL of formulation F with 6.4 mL of formulation AK and finally the volume was adjusted to 10 mL by adding water.

JT: A formulation consisting of insulin aspart and an insulin derivative was obtained by mixing 2.4 mL of formulation F with 5.6 mL of formulation AK and finally the volume was adjusted to 10 mL by adding water.

JU: A formulation consisting of insulin aspart and an insulin derivative was obtained by mixing 3.2 mL of formulation F with 4.8 mL of formulation AK and finally the volume was adjusted to 10 mL by adding water.

JV: A formulation consisting of insulin aspart and an insulin derivative was obtained by mixing 4.0 mL of formulation F with 4.0 mL of formulation AK and finally the volume was adjusted to 10 mL by adding water.

JX: A formulation consisting of insulin aspart and an insulin derivative was obtained by mixing 4.8 mL of formulation F with 3.2 mL of formulation AK and finally the volume was adjusted to 10 mL by adding water.

JY: A formulation consisting of insulin aspart and an insulin derivative was obtained by mixing 5.6 mL of formulation F with 2.4 mL of formulation AK and finally the volume was adjusted to 10 mL by adding water.

JZ: A formulation consisting of insulin aspart and an insulin derivative was obtained by mixing 6.4 mL of formulation F with 1.6 mL of formulation AK and finally the volume was adjusted to 10 mL by adding water.

KA: A formulation consisting of insulin aspart and an insulin derivative was obtained by mixing 7.2 mL of formulation F with 0.8 mL of formulation AK and finally the volume was adjusted to 10 mL by adding water.

KB: A formulation consisting of insulin aspart and an insulin derivative was obtained by mixing 0.8 mL of formulation G with 7.2 mL of formulation AL and finally the volume was adjusted to 10 mL by adding water.

KC: A formulation consisting of insulin aspart and an insulin derivative was obtained by mixing 1.6 mL of formulation G with 6.4 mL of formulation AL and finally the volume was adjusted to 10 mL by adding water.

KD: A formulation consisting of insulin aspart and an insulin derivative was obtained by mixing 2.4 mL of formulation G with 5.6 mL of formulation AL and finally the volume was adjusted to 10 mL by adding water.

KE: A formulation consisting of insulin aspart and an insulin derivative was obtained by mixing 3.2 mL of formulation G with 4.8 mL of formulation AL and finally the volume was adjusted to 10 mL by adding water.

KF: A formulation consisting of insulin aspart and an insulin derivative was obtained by mixing 4.0 mL of formulation G with 4.0 mL of formulation AL and finally the volume was adjusted to 10 mL by adding water.

KG: A formulation consisting of insulin aspart and an insulin derivative was obtained by mixing 4.8 mL of formulation G with 3.2 mL of formulation AL and finally the volume was adjusted to 10 mL by adding water.

KH: A formulation consisting of insulin aspart and an insulin derivative was obtained by mixing 5.6 mL of formulation G with 2.4 mL of formulation AL and finally the volume was adjusted to 10 mL by adding water.

KI: A formulation consisting of insulin aspart and an insulin derivative was obtained by mixing 6.4 mL of formulation G with 1.6 mL of formulation AL and finally the volume was adjusted to 10 mL by adding water.

KJ: A formulation consisting of insulin aspart and an insulin derivative was obtained by mixing 7.2 mL of formulation G with 0.8 mL of formulation AL and finally the volume was adjusted to 10 mL by adding water.

KK: A formulation consisting of insulin aspart and an insulin derivative was obtained by mixing 0.8 mL of formulation G with 7.2 mL of formulation AM and finally the volume was adjusted to 10 mL by adding water.

KL: A formulation consisting of insulin aspart and an insulin derivative was obtained by mixing 1.6 mL of formulation G with 6.4 mL of formulation AM and finally the volume was adjusted to 10 mL by adding water.

KM: A formulation consisting of insulin aspart and an insulin derivative was obtained by mixing 2.4 mL of formulation G with 5.6 mL of formulation AM and finally the volume was adjusted to 10 mL by adding water.

KN: A formulation consisting of insulin aspart and an insulin derivative was obtained by mixing 3.2 mL of formulation G with 4.8 mL of formulation AM and finally the volume was adjusted to 10 mL by adding water.

KO: A formulation consisting of insulin aspart and an insulin derivative was obtained by mixing 4.0 mL of formulation G with 4.0 mL of formulation AM and finally the volume was adjusted to 10 mL by adding water.

KP: A formulation consisting of insulin aspart and an insulin derivative was obtained by mixing 4.8 mL of formulation G with 3.2 mL of formulation AM and finally the volume was adjusted to 10 mL by adding water.

KQ: A formulation consisting of insulin aspart and an insulin derivative was obtained by mixing 5.6 mL of formulation G with 2.4 mL of formulation AM and finally the volume was adjusted to 10 mL by adding water.

KR: A formulation consisting of insulin aspart and an insulin derivative was obtained by mixing 6.4 mL of formulation G with 1.6 mL of formulation AM and finally the volume was adjusted to 10 mL by adding water.

KS: A formulation consisting of insulin aspart and an insulin derivative was obtained by mixing 7.2 mL of formulation G with 0.8 mL of formulation AM and finally the volume was adjusted to 10 mL by adding water.

KT: A formulation consisting of insulin aspart and an insulin derivative was obtained by mixing 0.8 mL of formulation G with 7.2 mL of formulation AN and finally the volume was adjusted to 10 mL by adding water.

KU: A formulation consisting of insulin aspart and an insulin derivative was obtained by mixing 1.6 mL of formulation G with 6.4 mL of formulation AN and finally the volume was adjusted to 10 mL by adding water.

KV: A formulation consisting of insulin aspart and an insulin derivative was obtained by mixing 2.4 mL of formulation G with 5.6 mL of formulation AN and finally the volume was adjusted to 10 mL by adding water.

KX: A formulation consisting of insulin aspart and an insulin derivative was obtained by mixing 3.2 mL of formulation G with 4.8 mL of formulation AN and finally the volume was adjusted to 10 mL by adding water.

KY: A formulation consisting of insulin aspart and an insulin derivative was obtained by mixing 4.0 mL of formulation G with 4.0 mL of formulation AN and finally the volume was adjusted to 10 mL by adding water.

KZ: A formulation consisting of insulin aspart and an insulin derivative was obtained by mixing 4.8 mL of formulation G with 3.2 mL of formulation AN and finally the volume was adjusted to 10 mL by adding water.

LA: A formulation consisting of insulin aspart and an insulin derivative was obtained by mixing 5.6 mL of formulation G with 2.4 mL of formulation AN and finally the volume was adjusted to 10 mL by adding water.

LB: A formulation consisting of insulin aspart and an insulin derivative was obtained by mixing 6.4 mL of formulation G with 1.6 mL of formulation AN and finally the volume was adjusted to 10 mL by adding water.

LC: A formulation consisting of insulin aspart and an insulin derivative was obtained by mixing 7.2 mL of formulation G with 0.8 mL of formulation AN and finally the volume was adjusted to 10 mL by adding water.

LD: A formulation consisting of insulin aspart and an insulin derivative was obtained by mixing 0.8 mL of formulation G with 7.2 mL of formulation AO and finally the volume was adjusted to 10 mL by adding water.

LE: A formulation consisting of insulin aspart and an insulin derivative was obtained by mixing 1.6 mL of formulation G with 6.4 mL of formulation AO and finally the volume was adjusted to 10 mL by adding water.

LF: A formulation consisting of insulin aspart and an insulin derivative was obtained by mixing 2.4 mL of formulation G with 5.6 mL of formulation AO and finally the volume was adjusted to 10 mL by adding water.

LG: A formulation consisting of insulin aspart and an insulin derivative was obtained by mixing 3.2 mL of formulation G with 4.8 mL of formulation AO and finally the volume was adjusted to 10 mL by adding water.

LH: A formulation consisting of insulin aspart and an insulin derivative was obtained by mixing 4.0 mL of formulation G with 4.0 mL of formulation AO and finally the volume was adjusted to 10 mL by adding water.

LI: A formulation consisting of insulin aspart and an insulin derivative was obtained by mixing 4.8 mL of formulation G with 3.2 mL of formulation AO and finally the volume was adjusted to 10 mL by adding water.

LJ: A formulation consisting of insulin aspart and an insulin derivative was obtained by mixing 5.6 mL of formulation G with 2.4 mL of formulation AO and finally the volume was adjusted to 10 mL by adding water.

LK: A formulation consisting of insulin aspart and an insulin derivative was obtained by mixing 6.4 mL of formulation G with 1.6 mL of formulation AO and finally the volume was adjusted to 10 mL by adding water.

LL: A formulation consisting of insulin aspart and an insulin derivative was obtained by mixing 7.2 mL of formulation G with 0.8 mL of formulation AO and finally the volume was adjusted to 10 mL by adding water.

LM: A formulation consisting of insulin aspart and an insulin derivative was obtained by mixing 0.8 mL of formulation H with 7.2 mL of formulation AP and finally the volume was adjusted to 10 mL by adding water.

LN: A formulation consisting of insulin aspart and an insulin derivative was obtained by mixing 1.6 mL of formulation H with 6.4 mL of formulation AP and finally the volume was adjusted to 10 mL by adding water.

LO: A formulation consisting of insulin aspart and an insulin derivative was obtained by mixing 2.4 mL of formulation H with 5.6 mL of formulation AP and finally the volume was adjusted to 10 mL by adding water.

LP: A formulation consisting of insulin aspart and an insulin derivative was obtained by mixing 3.2 mL of formulation H with 4.8 mL of formulation AP and finally the volume was adjusted to 10 mL by adding water.

LQ: A formulation consisting of insulin aspart and an insulin derivative was obtained by mixing 4.0 mL of formulation H with 4.0 mL of formulation AP and finally the volume was adjusted to 10 mL by adding water.

LR: A formulation consisting of insulin aspart and an insulin derivative was obtained by mixing 4.8 mL of formulation H with 3.2 mL of formulation AP and finally the volume was adjusted to 10 mL by adding water.

LS: A formulation consisting of insulin aspart and an insulin derivative was obtained by mixing 5.6 mL of formulation H with 2.4 mL of formulation AP and finally the volume was adjusted to 10 mL by adding water.

LT: A formulation consisting of insulin aspart and an insulin derivative was obtained by mixing 6.4 mL of formulation H with 1.6 mL of formulation AP and finally the volume was adjusted to 10 mL by adding water.

LU: A formulation consisting of insulin aspart and an insulin derivative was obtained by mixing 7.2 mL of formulation H with 0.8 mL of formulation AP and finally the volume was adjusted to 10 mL by adding water.

LV: A formulation consisting of insulin aspart and an insulin derivative was obtained by mixing 0.8 mL of formulation H with 7.2 mL of formulation AQ and finally the volume was adjusted to 10 mL by adding water.

LX: A formulation consisting of insulin aspart and an insulin derivative was obtained by mixing 1.6 mL of formulation H with 6.4 mL of formulation AQ and finally the volume was adjusted to 10 mL by adding water.

LY: A formulation consisting of insulin aspart and an insulin derivative was obtained by mixing 2.4 mL of formulation H with 5.6 mL of formulation AQ and finally the volume was adjusted to 10 mL by adding water.

LZ: A formulation consisting of insulin aspart and an insulin derivative was obtained by mixing 3.2 mL of formulation H with 4.8 mL of formulation AQ and finally the volume was adjusted to 10 mL by adding water.

MA: A formulation consisting of insulin aspart and an insulin derivative was obtained by mixing 4.0 mL of formulation H with 4.0 mL of formulation AQ and finally the volume was adjusted to 10 mL by adding water.

MB: A formulation consisting of insulin aspart and an insulin derivative was obtained by mixing 4.8 mL of formulation H with 3.2 mL of formulation AQ and finally the volume was adjusted to 10 mL by adding water.

MC: A formulation consisting of insulin aspart and an insulin derivative was obtained by mixing 5.6 mL of formulation H with 2.4 mL of formulation AQ and finally the volume was adjusted to 10 mL by adding water.

MD: A formulation consisting of insulin aspart and an insulin derivative was obtained by mixing 6.4 mL of formulation H with 1.6 mL of formulation AQ and finally the volume was adjusted to 10 mL by adding water.

ME: A formulation consisting of insulin aspart and an insulin derivative was obtained by mixing 7.2 mL of formulation H with 0.8 mL of formulation AQ and finally the volume was adjusted to 10 mL by adding water.

MF: A formulation consisting of insulin aspart and an insulin derivative was obtained by mixing 0.8 mL of formulation H with 7.2 mL of formulation AR and finally the volume was adjusted to 10 mL by adding water.

MG: A formulation consisting of insulin aspart and an insulin derivative was obtained by mixing 1.6 mL of formulation H with 6.4 mL of formulation AR and finally the volume was adjusted to 10 mL by adding water.

MH: A formulation consisting of insulin aspart and an insulin derivative was obtained by mixing 2.4 mL of formulation H with 5.6 mL of formulation AR and finally the volume was adjusted to 10 mL by adding water.

MI: A formulation consisting of insulin aspart and an insulin derivative was obtained by mixing 3.2 mL of formulation H with 4.8 mL of formulation AR and finally the volume was adjusted to 10 mL by adding water.

MJ: A formulation consisting of insulin aspart and an insulin derivative was obtained by mixing 4.0 mL of formulation H with 4.0 mL of formulation AR and finally the volume was adjusted to 10 mL by adding water.

MK: A formulation consisting of insulin aspart and an insulin derivative was obtained by mixing 4.8 mL of formulation H with 3.2 mL of formulation AR and finally the volume was adjusted to 10 mL by adding water.

ML: A formulation consisting of insulin aspart and an insulin derivative was obtained by mixing 5.6 mL of formulation H with 2.4 mL of formulation AR and finally the volume was adjusted to 10 mL by adding water.

MM: A formulation consisting of insulin aspart and an insulin derivative was obtained by mixing 6.4 mL of formulation H with 1.6 mL of formulation AR and finally the volume was adjusted to 10 mL by adding water.

MN: A formulation consisting of insulin aspart and an insulin derivative was obtained by mixing 7.2 mL of formulation H with 0.8 mL of formulation AR and finally the volume was adjusted to 10 mL by adding water.

MO: A formulation consisting of insulin aspart and an insulin derivative was obtained by mixing 0.8 mL of formulation H with 7.2 mL of formulation AS and finally the volume was adjusted to 10 mL by adding water.

MP: A formulation consisting of insulin aspart and an insulin derivative was obtained by mixing 1.6 mL of formulation H with 6.4 mL of formulation AS and finally the volume was adjusted to 10 mL by adding water.

MQ: A formulation consisting of insulin aspart and an insulin derivative was obtained by mixing 2.4 mL of formulation H with 5.6 mL of formulation AS and finally the volume was adjusted to 10 mL by adding water.

MR: A formulation consisting of insulin aspart and an insulin derivative was obtained by mixing 3.2 mL of formulation H with 4.8 mL of formulation AS and finally the volume was adjusted to 10 mL by adding water.

MS: A formulation consisting of insulin aspart and an insulin derivative was obtained by mixing 4.0 mL of formulation H with 4.0 mL of formulation AS and finally the volume was adjusted to 10 mL by adding water.

MT: A formulation consisting of insulin aspart and an insulin derivative was obtained by mixing 4.8 mL of formulation H with 3.2 mL of formulation AS and finally the volume was adjusted to 10 mL by adding water.

MU: A formulation consisting of insulin aspart and an insulin derivative was obtained by mixing 5.6 mL of formulation H with 2.4 mL of formulation AS and finally the volume was adjusted to 10 mL by adding water.

MV: A formulation consisting of insulin aspart and an insulin derivative was obtained by mixing 6.4 mL of formulation H with 1.6 mL of formulation AS and finally the volume was adjusted to 10 mL by adding water.

MX: A formulation consisting of insulin aspart and an insulin derivative was obtained by mixing 7.2 mL of formulation H with 0.8 mL of formulation AS and finally the volume was adjusted to 10 mL by adding water.

MY: A formulation consisting of insulin aspart and an insulin derivative was obtained by mixing 0.8 mL of formulation I with 7.2 mL of formulation AT and finally the volume was adjusted to 10 mL by adding water.

MZ: A formulation consisting of insulin aspart and an insulin derivative was obtained by mixing 1.6 mL of formulation I with 6.4 mL of formulation AT and finally the volume was adjusted to 10 mL by adding water.

NA: A formulation consisting of insulin aspart and an insulin derivative was obtained by mixing 2.4 mL of formulation I with 5.6 mL of formulation AT and finally the volume was adjusted to 10 mL by adding water.

NB: A formulation consisting of insulin aspart and an insulin derivative was obtained by mixing 3.2 mL of formulation I with 4.8 mL of formulation AT and finally the volume was adjusted to 10 mL by adding water.

NC: A formulation consisting of insulin aspart and an insulin derivative was obtained by mixing 4.0 mL of formulation I with 4.0 mL of formulation AT and finally the volume was adjusted to 10 mL by adding water.

ND: A formulation consisting of insulin aspart and an insulin derivative was obtained by mixing 4.8 mL of formulation I with 3.2 mL of formulation AT and finally the volume was adjusted to 10 mL by adding water.

NE: A formulation consisting of insulin aspart and an insulin derivative was obtained by mixing 5.6 mL of formulation I with 2.4 mL of formulation AT and finally the volume was adjusted to 10 mL by adding water.

NF: A formulation consisting of insulin aspart and an insulin derivative was obtained by mixing 6.4 mL of formulation I with 1.6 mL of formulation AT and finally the volume was adjusted to 10 mL by adding water.

NG: A formulation consisting of insulin aspart and an insulin derivative was obtained by mixing 7.2 mL of formulation I with 0.8 mL of formulation AT and finally the volume was adjusted to 10 mL by adding water.

NH: A formulation consisting of insulin aspart and an insulin derivative was obtained by mixing 0.8 mL of formulation I with 7.2 mL of formulation AU and finally the volume was adjusted to 10 mL by adding water.

NI: A formulation consisting of insulin aspart and an insulin derivative was obtained by mixing 1.6 mL of formulation I with 6.4 mL of formulation AU and finally the volume was adjusted to 10 mL by adding water.

NJ: A formulation consisting of insulin aspart and an insulin derivative was obtained by mixing 2.4 mL of formulation I with 5.6 mL of formulation AU and finally the volume was adjusted to 10 mL by adding water.

NK: A formulation consisting of insulin aspart and an insulin derivative was obtained by mixing 3.2 mL of formulation I with 4.8 mL of formulation AU and finally the volume was adjusted to 10 mL by adding water.

NL: A formulation consisting of insulin aspart and an insulin derivative was obtained by mixing 4.0 mL of formulation I with 4.0 mL of formulation AU and finally the volume was adjusted to 10 mL by adding water.

NM: A formulation consisting of insulin aspart and an insulin derivative was obtained by mixing 4.8 mL of formulation I with 3.2 mL of formulation AU and finally the volume was adjusted to 10 mL by adding water.

NN: A formulation consisting of insulin aspart and an insulin derivative was obtained by mixing 5.6 mL of formulation I with 2.4 mL of formulation AU and finally the volume was adjusted to 10 mL by adding water.

NO: A formulation consisting of insulin aspart and an insulin derivative was obtained by mixing 6.4 mL of formulation I with 1.6 mL of formulation AU and finally the volume was adjusted to 10 mL by adding water.

NP: A formulation consisting of insulin aspart and an insulin derivative was obtained by mixing 7.2 mL of formulation I with 0.8 mL of formulation AU and finally the volume was adjusted to 10 mL by adding water.

NO: A formulation consisting of insulin aspart and an insulin derivative was obtained by mixing 0.8 mL of formulation I with 7.2 mL of formulation AV and finally the volume was adjusted to 10 mL by adding water.

NR: A formulation consisting of insulin aspart and an insulin derivative was obtained by mixing 1.6 mL of formulation I with 6.4 mL of formulation AV and finally the volume was adjusted to 10 mL by adding water.

NS: A formulation consisting of insulin aspart and an insulin derivative was obtained by mixing 2.4 mL of formulation I with 5.6 mL of formulation AV and finally the volume was adjusted to 10 mL by adding water.

NT: A formulation consisting of insulin aspart and an insulin derivative was obtained by mixing 3.2 mL of formulation I with 4.8 mL of formulation AV and finally the volume was adjusted to 10 mL by adding water.

NU: A formulation consisting of insulin aspart and an insulin derivative was obtained by mixing 4.0 mL of formulation I with 4.0 mL of formulation AV and finally the volume was adjusted to 10 mL by adding water.

NV: A formulation consisting of insulin aspart and an insulin derivative was obtained by mixing 4.8 mL of formulation I with 3.2 mL of formulation AV and finally the volume was adjusted to 10 mL by adding water.

NX: A formulation consisting of insulin aspart and an insulin derivative was obtained by mixing 5.6 mL of formulation I with 2.4 mL of formulation AV and finally the volume was adjusted to 10 mL by adding water.

NY: A formulation consisting of insulin aspart and an insulin derivative was obtained by mixing 6.4 mL of formulation I with 1.6 mL of formulation AV and finally the volume was adjusted to 10 mL by adding water.

NZ: A formulation consisting of insulin aspart and an insulin derivative was obtained by mixing 7.2 mL of formulation I with 0.8 mL of formulation AV and finally the volume was adjusted to 10 mL by adding water.

OA: A formulation consisting of insulin aspart and an insulin derivative was obtained by mixing 0.8 mL of formulation I with 7.2 mL of formulation AX and finally the volume was adjusted to 10 mL by adding water.

OB: A formulation consisting of insulin aspart and an insulin derivative was obtained by mixing 1.6 mL of formulation I with 6.4 mL of formulation AX and finally the volume was adjusted to 10 mL by adding water.

OC: A formulation consisting of insulin aspart and an insulin derivative was obtained by mixing 2.4 mL of formulation I with 5.6 mL of formulation AX and finally the volume was adjusted to 10 mL by adding water.

OD: A formulation consisting of insulin aspart and an insulin derivative was obtained by mixing 3.2 mL of formulation I with 4.8 mL of formulation AX and finally the volume was adjusted to 10 mL by adding water.

OE: A formulation consisting of insulin aspart and an insulin derivative was obtained by mixing 4.0 mL of formulation I with 4.0 mL of formulation AX and finally the volume was adjusted to 10 mL by adding water.

OF: A formulation consisting of insulin aspart and an insulin derivative was obtained by mixing 4.8 mL of formulation I with 3.2 mL of formulation AX and finally the volume was adjusted to 10 mL by adding water.

OG: A formulation consisting of insulin aspart and an insulin derivative was obtained by mixing 5.6 mL of formulation I with 2.4 mL of formulation AX and finally the volume was adjusted to 10 mL by adding water.

OH: A formulation consisting of insulin aspart and an insulin derivative was obtained by mixing 6.4 mL of formulation I with 1.6 mL of formulation AX and finally the volume was adjusted to 10 mL by adding water.

OI: A formulation consisting of insulin aspart and an insulin derivative was obtained by mixing 7.2 mL of formulation I with 0.8 mL of formulation AX and finally the volume was adjusted to 10 mL by adding water.

OJ: A formulation consisting of insulin aspart and an insulin derivative was obtained by mixing 0.8 mL of formulation J with 7.2 mL of formulation AY and finally the volume was adjusted to 10 mL by adding water.

OK: A formulation consisting of insulin aspart and an insulin derivative was obtained by mixing 1.6 mL of formulation J with 6.4 mL of formulation AY and finally the volume was adjusted to 10 mL by adding water.

OL: A formulation consisting of insulin aspart and an insulin derivative was obtained by mixing 2.4 mL of formulation J with 5.6 mL of formulation AY and finally the volume was adjusted to 10 mL by adding water.

OM: A formulation consisting of insulin aspart and an insulin derivative was obtained by mixing 3.2 mL of formulation J with 4.8 mL of formulation AY and finally the volume was adjusted to 10 mL by adding water.

ON: A formulation consisting of insulin aspart and an insulin derivative was obtained by mixing 4.0 mL of formulation J with 4.0 mL of formulation AY and finally the volume was adjusted to 10 mL by adding water.

OO: A formulation consisting of insulin aspart and an insulin derivative was obtained by mixing 4.8 mL of formulation J with 3.2 mL of formulation AY and finally the volume was adjusted to 10 mL by adding water.

OP: A formulation consisting of insulin aspart and an insulin derivative was obtained by mixing 5.6 mL of formulation J with 2.4 mL of formulation AY and finally the volume was adjusted to 10 mL by adding water.

OQ: A formulation consisting of insulin aspart and an insulin derivative was obtained by mixing 6.4 mL of formulation J with 1.6 mL of formulation AY and finally the volume was adjusted to 10 mL by adding water.

OR: A formulation consisting of insulin aspart and an insulin derivative was obtained by mixing 7.2 mL of formulation J with 0.8 mL of formulation AY and finally the volume was adjusted to 10 mL by adding water.

OS: A formulation consisting of insulin aspart and an insulin derivative was obtained by mixing 0.8 mL of formulation J with 7.2 mL of formulation AZ and finally the volume was adjusted to 10 mL by adding water.

OT: A formulation consisting of insulin aspart and an insulin derivative was obtained by mixing 1.6 mL of formulation J with 6.4 mL of formulation AZ and finally the volume was adjusted to 10 mL by adding water.

OU: A formulation consisting of insulin aspart and an insulin derivative was obtained by mixing 2.4 mL of formulation J with 5.6 mL of formulation AZ and finally the volume was adjusted to 10 mL by adding water.

OV: A formulation consisting of insulin aspart and an insulin derivative was obtained by mixing 3.2 mL of formulation J with 4.8 mL of formulation AZ and finally the volume was adjusted to 10 mL by adding water.

OX: A formulation consisting of insulin aspart and an insulin derivative was obtained by mixing 4.0 mL of formulation J with 4.0 mL of formulation AZ and finally the volume was adjusted to 10 mL by adding water.

OY: A formulation consisting of insulin aspart and an insulin derivative was obtained by mixing 4.8 mL of formulation J with 3.2 mL of formulation AZ and finally the volume was adjusted to 10 mL by adding water.

OZ: A formulation consisting of insulin aspart and an insulin derivative was obtained by mixing 5.6 mL of formulation J with 2.4 mL of formulation AZ and finally the volume was adjusted to 10 mL by adding water.

PA: A formulation consisting of insulin aspart and an insulin derivative was obtained by mixing 6.4 mL of formulation J with 1.6 mL of formulation AZ and finally the volume was adjusted to 10 mL by adding water.

PB: A formulation consisting of insulin aspart and an insulin derivative was obtained by mixing 7.2 mL of formulation J with 0.8 mL of formulation AZ and finally the volume was adjusted to 10 mL by adding water.

PC: A formulation consisting of insulin aspart and an insulin derivative was obtained by mixing 0.8 mL of formulation J with 7.2 mL of formulation BA and finally the volume was adjusted to 10 mL by adding water.

PD: A formulation consisting of insulin aspart and an insulin derivative was obtained by mixing 1.6 mL of formulation J with 6.4 mL of formulation BA and finally the volume was adjusted to 10 mL by adding water.

PE: A formulation consisting of insulin aspart and an insulin derivative was obtained by mixing 2.4 mL of formulation J with 5.6 mL of formulation BA and finally the volume was adjusted to 10 mL by adding water.

PF: A formulation consisting of insulin aspart and an insulin derivative was obtained by mixing 3.2 mL of formulation J with 4.8 mL of formulation BA and finally the volume was adjusted to 10 mL by adding water.

PG: A formulation consisting of insulin aspart and an insulin derivative was obtained by mixing 4.0 mL of formulation J with 4.0 mL of formulation BA and finally the volume was adjusted to 10 mL by adding water.

PH: A formulation consisting of insulin aspart and an insulin derivative was obtained by mixing 4.8 mL of formulation J with 3.2 mL of formulation BA and finally the volume was adjusted to 10 mL by adding water.

PI: A formulation consisting of insulin aspart and an insulin derivative was obtained by mixing 5.6 mL of formulation J with 2.4 mL of formulation BA and finally the volume was adjusted to 10 mL by adding water.

PJ: A formulation consisting of insulin aspart and an insulin derivative was obtained by mixing 6.4 mL of formulation J with 1.6 mL of formulation BA and finally the volume was adjusted to 10 mL by adding water.

PK: A formulation consisting of insulin aspart and an insulin derivative was obtained by mixing 7.2 mL of formulation J with 0.8 mL of formulation BA and finally the volume was adjusted to 10 mL by adding water.

PL: A formulation consisting of insulin aspart and an insulin derivative was obtained by mixing 0.8 mL of formulation J with 7.2 mL of formulation BB and finally the volume was adjusted to 10 mL by adding water.

PM: A formulation consisting of insulin aspart and an insulin derivative was obtained by mixing 1.6 mL of formulation J with 6.4 mL of formulation BB and finally the volume was adjusted to 10 mL by adding water.

PN: A formulation consisting of insulin aspart and an insulin derivative was obtained by mixing 2.4 mL of formulation J with 5.6 mL of formulation BB and finally the volume was adjusted to 10 mL by adding water.

PO: A formulation consisting of insulin aspart and an insulin derivative was obtained by mixing 3.2 mL of formulation J with 4.8 mL of formulation BB and finally the volume was adjusted to 10 mL by adding water.

PP: A formulation consisting of insulin aspart and an insulin derivative was obtained by mixing 4.0 mL of formulation J with 4.0 mL of formulation BB and finally the volume was adjusted to 10 mL by adding water.

PQ: A formulation consisting of insulin aspart and an insulin derivative was obtained by mixing 4.8 mL of formulation J with 3.2 mL of formulation BB and finally the volume was adjusted to 10 mL by adding water.

PR: A formulation consisting of insulin aspart and an insulin derivative was obtained by mixing 5.6 mL of formulation J with 2.4 mL of formulation BB and finally the volume was adjusted to 10 mL by adding water.

PS: A formulation consisting of insulin aspart and an insulin derivative was obtained by mixing 6.4 mL of formulation J with 1.6 mL of formulation BB and finally the volume was adjusted to 10 mL by adding water.

PT: A formulation consisting of insulin aspart and an insulin derivative was obtained by mixing 7.2 mL of formulation J with 0.8 mL of formulation BB and finally the volume was adjusted to 10 mL by adding water.

PU: A formulation consisting of insulin aspart and an insulin derivative was obtained by mixing 0.8 mL of formulation K with 7.2 mL of formulation BC and finally the volume was adjusted to 10 mL by adding water.

PV: A formulation consisting of insulin aspart and an insulin derivative was obtained by mixing 1.6 mL of formulation K with 6.4 mL of formulation BC and finally the volume was adjusted to 10 mL by adding water.

PX: A formulation consisting of insulin aspart and an insulin derivative was obtained by mixing 2.4 mL of formulation K with 5.6 mL of formulation BC and finally the volume was adjusted to 10 mL by adding water.

PY: A formulation consisting of insulin aspart and an insulin derivative was obtained by mixing 3.2 mL of formulation K with 4.8 mL of formulation BC and finally the volume was adjusted to 10 mL by adding water.

PZ: A formulation consisting of insulin aspart and an insulin derivative was obtained by mixing 4.0 mL of formulation K with 4.0 mL of formulation BC and finally the volume was adjusted to 10 mL by adding water.

QA: A formulation consisting of insulin aspart and an insulin derivative was obtained by mixing 4.8 mL of formulation K with 3.2 mL of formulation BC and finally the volume was adjusted to 10 mL by adding water.

QB: A formulation consisting of insulin aspart and an insulin derivative was obtained by mixing 5.6 mL of formulation K with 2.4 mL of formulation BC and finally the volume was adjusted to 10 mL by adding water.

QC: A formulation consisting of insulin aspart and an insulin derivative was obtained by mixing 6.4 mL of formulation K with 1.6 mL of formulation BC and finally the volume was adjusted to 10 mL by adding water.

QD: A formulation consisting of insulin aspart and an insulin derivative was obtained by mixing 7.2 mL of formulation K with 0.8 mL of formulation BC and finally the volume was adjusted to 10 mL by adding water.

QE: A formulation consisting of insulin aspart and an insulin derivative was obtained by mixing 0.8 mL of formulation K with 7.2 mL of formulation BD and finally the volume was adjusted to 10 mL by adding water.

QF: A formulation consisting of insulin aspart and an insulin derivative was obtained by mixing 1.6 mL of formulation K with 6.4 mL of formulation BD and finally the volume was adjusted to 10 mL by adding water.

QG: A formulation consisting of insulin aspart and an insulin derivative was obtained by mixing 2.4 mL of formulation K with 5.6 mL of formulation BD and finally the volume was adjusted to 10 mL by adding water.

QH: A formulation consisting of insulin aspart and an insulin derivative was obtained by mixing 3.2 mL of formulation K with 4.8 mL of formulation BD and finally the volume was adjusted to 10 mL by adding water.

QI: A formulation consisting of insulin aspart and an insulin derivative was obtained by mixing 4.0 mL of formulation K with 4.0 mL of formulation BD and finally the volume was adjusted to 10 mL by adding water.

QJ: A formulation consisting of insulin aspart and an insulin derivative was obtained by mixing 4.8 mL of formulation K with 3.2 mL of formulation BD and finally the volume was adjusted to 10 mL by adding water.

QK: A formulation consisting of insulin aspart and an insulin derivative was obtained by mixing 5.6 mL of formulation K with 2.4 mL of formulation BD and finally the volume was adjusted to 10 mL by adding water.

QL: A formulation consisting of insulin aspart and an insulin derivative was obtained by mixing 6.4 mL of formulation K with 1.6 mL of formulation BD and finally the volume was adjusted to 10 mL by adding water.

QM: A formulation consisting of insulin aspart and an insulin derivative was obtained by mixing 7.2 mL of formulation K with 0.8 mL of formulation BD and finally the volume was adjusted to 10 mL by adding water.

QN: A formulation consisting of insulin aspart and an insulin derivative was obtained by mixing 0.8 mL of formulation K with 7.2 mL of formulation BE and finally the volume was adjusted to 10 mL by adding water.

QO: A formulation consisting of insulin aspart and an insulin derivative was obtained by mixing 1.6 mL of formulation K with 6.4 mL of formulation BE and finally the volume was adjusted to 10 mL by adding water.

QP: A formulation consisting of insulin aspart and an insulin derivative was obtained by mixing 2.4 mL of formulation K with 5.6 mL of formulation BE and finally the volume was adjusted to 10 mL by adding water.

QQ: A formulation consisting of insulin aspart and an insulin derivative was obtained by mixing 3.2 mL of formulation K with 4.8 mL of formulation BE and finally the volume was adjusted to 10 mL by adding water.

QR: A formulation consisting of insulin aspart and an insulin derivative was obtained by mixing 4.0 mL of formulation K with 4.0 mL of formulation BE and finally the volume was adjusted to 10 mL by adding water.

QS: A formulation consisting of insulin aspart and an insulin derivative was obtained by mixing 4.8 mL of formulation K with 3.2 mL of formulation BE and finally the volume was adjusted to 10 mL by adding water.

QT: A formulation consisting of insulin aspart and an insulin derivative was obtained by mixing 5.6 mL of formulation K with 2.4 mL of formulation BE and finally the volume was adjusted to 10 mL by adding water.

QU: A formulation consisting of insulin aspart and an insulin derivative was obtained by mixing 6.4 mL of formulation K with 1.6 mL of formulation BE and finally the volume was adjusted to 10 mL by adding water.

QV: A formulation consisting of insulin aspart and an insulin derivative was obtained by mixing 7.2 mL of formulation K with 0.8 mL of formulation BE and finally the volume was adjusted to 10 mL by adding water.

QX: A formulation consisting of insulin aspart and an insulin derivative was obtained by mixing 0.8 mL of formulation K with 7.2 mL of formulation BF and finally the volume was adjusted to 10 mL by adding water.

QY: A formulation consisting of insulin aspart and an insulin derivative was obtained by mixing 1.6 mL of formulation K with 6.4 mL of formulation BF and finally the volume was adjusted to 10 mL by adding water.

QZ: A formulation consisting of insulin aspart and an insulin derivative was obtained by mixing 2.4 mL of formulation K with 5.6 mL of formulation BF and finally the volume was adjusted to 10 mL by adding water.

RA: A formulation consisting of insulin aspart and an insulin derivative was obtained by mixing 3.2 mL of formulation K with 4.8 mL of formulation BF and finally the volume was adjusted to 10 mL by adding water.

RB: A formulation consisting of insulin aspart and an insulin derivative was obtained by mixing 4.0 mL of formulation K with 4.0 mL of formulation BF and finally the volume was adjusted to 10 mL by adding water.

RC: A formulation consisting of insulin aspart and an insulin derivative was obtained by mixing 4.8 mL of formulation K with 3.2 mL of formulation BF and finally the volume was adjusted to 10 mL by adding water.

RD: A formulation consisting of insulin aspart and an insulin derivative was obtained by mixing 5.6 mL of formulation K with 2.4 mL of formulation BF and finally the volume was adjusted to 10 mL by adding water.

RE: A formulation consisting of insulin aspart and an insulin derivative was obtained by mixing 6.4 mL of formulation K with 1.6 mL of formulation BF and finally the volume was adjusted to 10 mL by adding water.

RF: A formulation consisting of insulin aspart and an insulin derivative was obtained by mixing 7.2 mL of formulation K with 0.8 mL of formulation BF and finally the volume was adjusted to 10 mL by adding water.

RG: A formulation consisting of insulin aspart and an insulin derivative was obtained by mixing 0.8 mL of formulation L with 7.2 mL of formulation BG and finally the volume was adjusted to 10 mL by adding water.

RH: A formulation consisting of insulin aspart and an insulin derivative was obtained by mixing 1.6 mL of formulation L with 6.4 mL of formulation BG and finally the volume was adjusted to 10 mL by adding water.

RI: A formulation consisting of insulin aspart and an insulin derivative was obtained by mixing 2.4 mL of formulation L with 5.6 mL of formulation BG and finally the volume was adjusted to 10 mL by adding water.

RJ: A formulation consisting of insulin aspart and an insulin derivative was obtained by mixing 3.2 mL of formulation L with 4.8 mL of formulation BG and finally the volume was adjusted to 10 mL by adding water.

RK: A formulation consisting of insulin aspart and an insulin derivative was obtained by mixing 4.0 mL of formulation L with 4.0 mL of formulation BG and finally the volume was adjusted to 10 mL by adding water.

RL: A formulation consisting of insulin aspart and an insulin derivative was obtained by mixing 4.8 mL of formulation L with 3.2 mL of formulation BG and finally the volume was adjusted to 10 mL by adding water.

RM: A formulation consisting of insulin aspart and an insulin derivative was obtained by mixing 5.6 mL of formulation L with 2.4 mL of formulation BG and finally the volume was adjusted to 10 mL by adding water.

RN: A formulation consisting of insulin aspart and an insulin derivative was obtained by mixing 6.4 mL of formulation L with 1.6 mL of formulation BG and finally the volume was adjusted to 10 mL by adding water.

RO: A formulation consisting of insulin aspart and an insulin derivative was obtained by mixing 7.2 mL of formulation L with 0.8 mL of formulation BG and finally the volume was adjusted to 10 mL by adding water.

RP: A formulation consisting of insulin aspart and an insulin derivative was obtained by mixing 0.8 mL of formulation L with 7.2 mL of formulation BH and finally the volume was adjusted to 10 mL by adding water.

RQ: A formulation consisting of insulin aspart and an insulin derivative was obtained by mixing 1.6 mL of formulation L with 6.4 mL of formulation BH and finally the volume was adjusted to 10 mL by adding water.

RR: A formulation consisting of insulin aspart and an insulin derivative was obtained by mixing 2.4 mL of formulation L with 5.6 mL of formulation BH and finally the volume was adjusted to 10 mL by adding water.

RS: A formulation consisting of insulin aspart and an insulin derivative was obtained by mixing 3.2 mL of formulation L with 4.8 mL of formulation BH and finally the volume was adjusted to 10 mL by adding water.

RT: A formulation consisting of insulin aspart and an insulin derivative was obtained by mixing 4.0 mL of formulation L with 4.0 mL of formulation BH and finally the volume was adjusted to 10 mL by adding water.

RU: A formulation consisting of insulin aspart and an insulin derivative was obtained by mixing 4.8 mL of formulation L with 3.2 mL of formulation BH and finally the volume was adjusted to 10 mL by adding water.

RV: A formulation consisting of insulin aspart and an insulin derivative was obtained by mixing 5.6 mL of formulation L with 2.4 mL of formulation BH and finally the volume was adjusted to 10 mL by adding water.

RX: A formulation consisting of insulin aspart and an insulin derivative was obtained by mixing 6.4 mL of formulation L with 1.6 mL of formulation BH and finally the volume was adjusted to 10 mL by adding water.

RY: A formulation consisting of insulin aspart and an insulin derivative was obtained by mixing 7.2 mL of formulation L with 0.8 mL of formulation BH and finally the volume was adjusted to 10 mL by adding water.

RZ: A formulation consisting of insulin aspart and an insulin derivative was obtained by mixing 0.8 mL of formulation L with 7.2 mL of formulation BI and finally the volume was adjusted to 10 mL by adding water.

SA: A formulation consisting of insulin aspart and an insulin derivative was obtained by mixing 1.6 mL of formulation L with 6.4 mL of formulation BI and finally the volume was adjusted to 10 mL by adding water.

SB: A formulation consisting of insulin aspart and an insulin derivative was obtained by mixing 2.4 mL of formulation L with 5.6 mL of formulation BI and finally the volume was adjusted to 10 mL by adding water.

SC: A formulation consisting of insulin aspart and an insulin derivative was obtained by mixing 3.2 mL of formulation L with 4.8 mL of formulation BI and finally the volume was adjusted to 10 mL by adding water.

SD: A formulation consisting of insulin aspart and an insulin derivative was obtained by mixing 4.0 mL of formulation L with 4.0 mL of formulation BI and finally the volume was adjusted to 10 mL by adding water.

SE: A formulation consisting of insulin aspart and an insulin derivative was obtained by mixing 4.8 mL of formulation L with 3.2 mL of formulation BI and finally the volume was adjusted to 10 mL by adding water.

SF: A formulation consisting of insulin aspart and an insulin derivative was obtained by mixing 5.6 mL of formulation L with 2.4 mL of formulation BI and finally the volume was adjusted to 10 mL by adding water.

SG: A formulation consisting of insulin aspart and an insulin derivative was obtained by mixing 6.4 mL of formulation L with 1.6 mL of formulation BI and finally the volume was adjusted to 10 mL by adding water.

SH: A formulation consisting of insulin aspart and an insulin derivative was obtained by mixing 7.2 mL of formulation L with 0.8 mL of formulation BI and finally the volume was adjusted to 10 mL by adding water.

SI: A formulation consisting of insulin aspart and an insulin derivative was obtained by mixing 0.8 mL of formulation L with 7.2 mL of formulation BJ and finally the volume was adjusted to 10 mL by adding water.

SJ: A formulation consisting of insulin aspart and an insulin derivative was obtained by mixing 1.6 mL of formulation L with 6.4 mL of formulation BJ and finally the volume was adjusted to 10 mL by adding water.

SK: A formulation consisting of insulin aspart and an insulin derivative was obtained by mixing 2.4 mL of formulation L with 5.6 mL of formulation BJ and finally the volume was adjusted to 10 mL by adding water.

SL: A formulation consisting of insulin aspart and an insulin derivative was obtained by mixing 3.2 mL of formulation L with 4.8 mL of formulation BJ and finally the volume was adjusted to 10 mL by adding water.

SM: A formulation consisting of insulin aspart and an insulin derivative was obtained by mixing 4.0 mL of formulation L with 4.0 mL of formulation BJ and finally the volume was adjusted to 10 mL by adding water.

SN: A formulation consisting of insulin aspart and an insulin derivative was obtained by mixing 4.8 mL of formulation L with 3.2 mL of formulation BJ and finally the volume was adjusted to 10 mL by adding water.

SO: A formulation consisting of insulin aspart and an insulin derivative was obtained by mixing 5.6 mL of formulation L with 2.4 mL of formulation BJ and finally the volume was adjusted to 10 mL by adding water.

SP: A formulation consisting of insulin aspart and an insulin derivative was obtained by mixing 6.4 mL of formulation L with 1.6 mL of formulation BJ and finally the volume was adjusted to 10 mL by adding water.

SQ: A formulation consisting of insulin aspart and an insulin derivative was obtained by mixing 7.2 mL of formulation L with 0.8 mL of formulation BJ and finally the volume was adjusted to 10 mL by adding water.

Pharmacological Methods

Assay (I)

Insulin Receptor Binding of the Insulin Derivatives of the Invention

The affinity of the insulin analogues of the invention for the human insulin receptor was determined by a SPA assay (Scintillation Proximity Assay) microtiterplate antibody capture assay. SPA-PVT antibody-binding beads, anti-mouse reagent (Amersham Biosciences, Cat No. PRNQ0017) were mixed with 25 ml of binding buffer (100 mM HEPES pH 7.8; 100 mM sodium chloride, 10 mM $MgSO_4$, 0.025% Tween-20). Reagent mix for a single Packard Optiplate (Packard No. 6005190) is composed of 2.4 µl of a 1:5000 diluted purified recombinant human insulin receptor—exon 11, an amount of a stock solution of A14 Tyr[$^{125}$I]-human insulin corresponding to 5000 cpm per 100 µl of reagent mix, 12 µl of a 1:1000 dilution of F12 antibody, 3 ml of SPA-beads and binding buffer to a total of 12 ml. A total of 100 µl was then added and a dilution series is made from appropriate samples. To the dilution series was then added 100 µl of reagent mix and the samples were incubated for 16 hours while gently shaken. The phases were the then separated by centrifugation for 1 min and the plates counted in a Topcounter. The binding data were fitted using the nonlinear regression algorithm in the GraphPad Prism 2.01 (GraphPad Software, San Diego, Calif.).

Assay (II)
Potency of the Insulin Derivatives of the Invention Relative to Human Insulin Sprague Dawley male rats weighing 238-383 g on the experimental day are used for the clamp experiment. The rats has free access to feed under controlled ambient conditions and fast overnight (from 3 μm) prior to the clamp experiment.
Experimental Protocol The rats are acclimatized in the animal facilities for at least 1 week prior to the surgical procedure. Approximately 1 week prior to the clamp experiment Tygon catheters are inserted under halothane anaesthesia into the jugular vein (for infusion) and the carotid artery (for blood sampling) and exteriorised and fixed on the back of the neck. The rats are given Streptocilin vet. (Boehringer Ingelheim; 0.15 ml/rat, i.m.) post-surgically and placed in an animal care unit (25° C.) during the recovery period. In order to obtain analgesia, Anorphin (0.06 mg/rat, s.c.) is administered during anaesthesia and Rimadyl (1.5 mg/kg, s.c.) is administered after full recovery from the anaesthesia (2-3 h) and again once daily for 2 days.

The clamp technique employed is adapted from (1). At 7 am on the experimental day overnight fasted (from 3 pm the previous day) rats are weighed and connected to the sampling syringes and infusion system (Harvard 22 Basic pumps, Harvard, and Perfectum Hypodermic glass syringe, Aldrich) and then placed into individual clamp cages where they rest for ca. 45 min before start of experiment. The rats are able to move freely on their usual bedding during the entire experiment and had free access to drinking water. After a 30 min basal period during which plasma glucose levels were measured at 10 min intervals, the insulin derivative to be tested and human insulin (one dose level per rat, n=6-7 per dose level) were infused (i.v.) at a constant rate for 300 min. Plasma glucose levels are measured at 10 min intervals throughout and infusion of 20% aqueous glucose is adjusted accordingly in order to maintain euglyceamia. Samples of re-suspended erythrocytes were pooled from each rat and returned in about ½ ml volumes via the carotid catheter.

On each experimental day, samples of the solutions of the individual insulin derivatives to be tested and the human insulin solution are taken before and at the end of the clamp experiments and the concentrations of the peptides were confirmed by HPLC. Plasma concentrations of rat insulin and C-peptide as well as of the insulin derivative to be tested and human insulin are measured at relevant time points before and at the end of the studies. Rats are killed at the end of experiment using a pentobarbital overdose.

Test Compounds and Doses:
Insulins to be tested are diluted from a stock solution containing 97 μM of the insulin derivative in 5 mM phosphate pH 7.7. The final concentration in the solution ready for use is 0.45 μM of the insulin derivative, 5 mM of phosphate, 100 mM of sodium chloride, 0.007% of polysorbate 20. The pH was 7.7 and the i.v. infusion rate was 15 and 20 pmol·min$^{-1}$·kg$^{-1}$.

A stock solution of human insulin that is used as reference compound was formulated in a similar medium and infused i.v. at 6, 15 or 30 pmol·min$^{-1}$·kg$^{-1}$.

Both stock solutions are stored at −20° C. and thawed overnight at 4° C. before use. The solutions are gently turned upside down several times 15 min before they are transferred to the infusion syringes.
Assay (III)
Determination in Pigs of $T_{50\%}$ of the Insulin Derivatives of the Invention $T_{50\%}$ is the time when 50% of an injected amount of the A14 Tyr[$^{125}$I] labelled derivative of an insulin to be tested has disappeared from the injection site as measured with an external γ-counter.

The principles of laboratory animal care are followed, Specific pathogen-free LYYD, non-diabetic female pigs, crossbreed of Danish Landrace, Yorkshire and Duroc, are used (Holmenlund, Haarloev, Denmark) for pharmacokinetic and pharmacodynamic studies. The pigs are conscious, 4-5 months of age and weighing 70-95 kg. The animals fast overnight for 18 h before the experiment.

Formulated preparations of insulin derivatives labelled in Tyr$^{A14}$ with $^{125}$I are injected sc. in pigs as previously described (Ribel, U., Jørgensen, K, Brange, J, and Henriksen, U. The pig as a model for subcutaneous insulin absorption in man. Serrano-Rios, M and Lefèbvre, P. J. 891-896. 1985. Amsterdam; New York; Oxford, Elsevier Science Publishers. 1985 (Conference Proceeding)).

At the beginning of the experiments a dose of 60 nmol of the insulin derivative according to the invention (test compound) and a dose of 60 nmol of insulin detemir (both $^{125}$I labelled in Tyr A14) are injected at two separate sites in the neck of each pig.

The disappearance of the radioactive label from the site of sc. injection is monitored using a modification of the traditional external gamma-counting method (Ribel, U. Subcutaneous absorption of insulin analogues. Berger, M. and Gries, F. A. 70-77 (1993). Stuttgart; New York, Georg Thime Verlag (Conference Proceeding)). With this modified method it is possible to measure continuously the disappearance of radioactivity from a subcutaneous depot for several days using cordless portable device (Scancys Laboratorieteknik, Værløse, DK-3500, Denmark). The measurements are performed at 1-min intervals, and the counted values are corrected for background activity.

The invention claimed is:
1. An insulin derivative having a formula

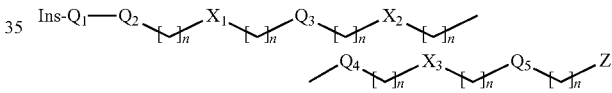

wherein Ins is a parent insulin moiety and $Q_1$-$Q_2$-$[CH_2]_n$—$X_1$—$[CH_2]_n$-$Q_3$-$[CH_2]_n$—$X_2$—$[CH_2]_n$-$Q_4$-$[CH_2]_n$—$X_3$—$[CH_2]_n$-$Q_5$-$[CH_2]_n$—Z is a substituent and where the Ins is attached to the substituent via an amide bond between the α-amino group of the N-terminal amino acid residue of the B chain of Ins or an ε-amino group of a Lys residue present in the A or B chain of Ins and a CO group in $Q_1$ or $Q_2$ of the substituent;

$Q_1$ is selected from the group consisting of:
  an amino acid residue, which residue forms, with its carboxylic acid group, an amide group together with the α-amino group of the N-terminal amino acid residue of the B chain of Ins or together with the ε-amino group of a Lys residue present in the A or B chain of Ins,
  a chain composed of two, three or four α-amino acid residues as specified above linked together via amide bonds, which chain is linked via an amide bond to the α-amino group of the N-terminal amino acid residue of the B chain of Ins or to the ε-amino group of a Lys residue present in the A or B chain of Ins, and
  a bond $Q_2$ is selected from the group consisting of:

—CO—$(CH_2)_2$—NH—$(CH_2)_2$—,

—CO—$CH_2$—NH—$CH_2$—,

—CO—$(CH_2)_p$—$NR^1$—$(CH_2)_{p'}$—, and

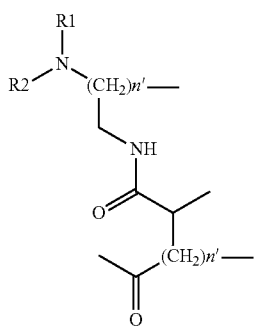

where n'=1-6, where $R^1$ and $R^2$, independently of each other can be H, —$CH_3$ or —$(CH_2)_{1-6}$—$CH_3$, and where p and p' independently of each other can be 1-6;

$Q_3$ is —$(CH_2)_m$— where m is an integer in the range of 6 to 32;

$X_1$ is selected from the group consisting of:
O,
—C=O, and
$NCOR^1$, where $R^1$ can be H, —$CH_3$ or —$(CH_2)_{1-6}$— $CH_3$, and

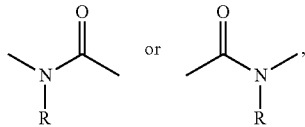

where R is hydrogen, $C_{1-3}$-alkyl, $C_{2-3}$-alkenyl or $C_{2-3}$-alkynyl;

$Q_4$, $Q_5$, $X_2$ and $X_3$ are bonds and all n are zero; and

Z is —COOH and any $Zn^{2+}$ complex thereof.

2. The insulin derivative according to claim 1, wherein $Q_1$ is a bond.

3. The insulin derivative according to claim 1, wherein $X_1$ is

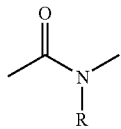

where R is hydrogen.

4. The insulin derivative according to claim 1, wherein $Q_3$ is —$(CH_2)_m$— where m is 12, 13, 14, 15 or 16.

5. The insulin derivative according to claim 1, wherein the substituent is attached to the ε-amino group of a Lys residue present in the A or B chain of the parent insulin.

6. A pharmaceutical composition for the treatment of diabetes in a patient in need of such treatment, comprising a therapeutically effective amount of the insulin derivative of claim 1.

7. The pharmaceutical composition according to claim 6, wherein the composition comprises pharmaceutically acceptable excipients.

8. The pharmaceutical composition according to claim 6, wherein the composition comprises an insulin analogue which has a rapid onset of action.

9. A method of treating diabetes in a patient in need of such a treatment by the use of a therapeutically effective amount of an insulin derivative having a formula

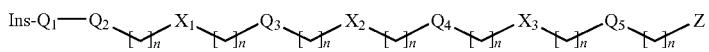

wherein Ins is a parent insulin moiety and $Q_1$-$Q_2$-$[CH_2]_n$—$X_1$—$[CH_2]_n$-$Q_3$-$[CH_2]_n$—$X_2$—$[CH_2]_n$-$Q_4$-$[CH_2]_n$—$X_3$—$[CH_2]_n$-$Q_5$-$[CH_2]_n$—Z is a substituent and where the Ins is attached to the substituent via an amide bond between the α-amino group of the N-terminal amino acid residue of the B chain of Ins or an ε-amino group of a Lys residue present in the A or B chain of Ins and a CO group in $Q_1$ or $Q_2$ of the substituent;

$Q_1$ is selected from the group consisting of:
an amino acid residue, which residue forms, with its carboxylic acid group, an amide group together with the α-amino group of the N-terminal amino acid residue of the B chain of Ins or together with the ε-amino group of a Lys residue present in the A or B chain of Ins, a chain composed of two, three or four α-amino acid residues as specified above linked together via amide bonds, which chain is linked via an amide bond to the α-amino group of the N-terminal amino acid residue of the B chain of Ins or to the ε-amino group of a Lys residue present in the A or B chain of Ins, and a bond $Q_2$ is selected from the group consisting of:

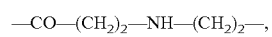

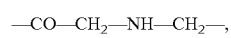

, and

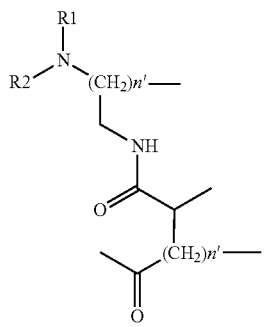

where n'=1-6, where $R^1$ and $R^2$, independently of each other can be H, —$CH_3$ or —$(CH_2)_{1-6}$—$CH_3$, and where p and p' independently of each other can be 1-6;

$Q_3$ is —$(CH_2)_m$— where m is an integer in the range of 6 to 32;

$X_1$ is selected from the group consisting of:
O,
—C=O, and
$NCOR^1$, where $R^1$ can be H, —$CH_3$ or —$(CH_2)_{1-6}$— $CH_3$, and

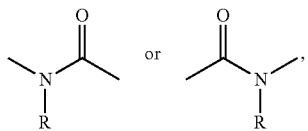

where R is hydrogen, $C_{1-3}$-alkyl, $C_{2-3}$-alkenyl or $C_{2-3}$-alkynyl;

$Q_4$, $Q_5$, $X_2$ and $X_3$ are bonds and all n are zero; and

Z is —COOH and any $Zn^{2+}$ complex thereof.

10. The method according to claim 9 for pulmonary treatment of diabetes.

11. The insulin derivative of claim 1, wherein the substituent is attached to the ε-amino group of the Lys residue in position B29 present in the B chain of the parent insulin.

12. The insulin derivative of claim 1, wherein the parent insulin is an insulin analogue.

13. The insulin derivative of claim 1, wherein the amino acid residue at position B30 of the parent insulin is Lys or has been deleted.

14. The insulin derivative of claim 1, wherein the substituent is attached to the ε-amino group of the Lys residue in position B29 in desB30 human insulin.

15. The insulin derivative of claim 1, wherein the parent insulin is selected from the group consisting of AspB28 human insulin, GlyA21 human insulin, GlyA21desB30 human insulin, GlyA21ArgB31ArgB32 human insulin, LysB28ProB29 human insulin, ThrB29LysB30 human insulin, and LysB3GluB29 human insulin.

16. The insulin derivative of claim 1, further comprising 2-10 zinc ions per six molecules of insulin derivative bound to form a zinc complex with the insulin derivative.

17. The pharmaceutical composition of claim 8, wherein the rapid acting insulin analogue is selected from the group consisting of AspB28 human insulin; LysB28ProB29 human insulin and LysB3GluB29 human insulin.

* * * * *